United States Patent [19]

Ito et al.

[11] Patent Number: 5,597,848
[45] Date of Patent: Jan. 28, 1997

[54] BENZENESULFONAMIDE DERIVATIVES AND USE THEREOF

[75] Inventors: Yasuo Ito, Katsuyama; Hideo Kato, Fukui; Shingo Yasuda, Katsuyama; Nobuo Ogawa, Katsuyama; Shunichiro Sakurai, Katsuyama; Tomio Suzuki, Fukui-ken, all of Japan

[73] Assignee: Hokuriku Seiyaku Co., Ltd., Katsuyama, Japan

[21] Appl. No.: 397,068

[22] PCT Filed: Sep. 29, 1993

[86] PCT No.: PCT/JP93/01382

§ 371 Date: Mar. 16, 1995

§ 102(e) Date: Mar. 16, 1995

[87] PCT Pub. No.: WO94/07848

PCT Pub. Date: Apr. 14, 1994

[30] Foreign Application Priority Data

Oct. 1, 1992 [JP] Japan .................. 4-284938
Jun. 11, 1993 [JP] Japan .................. 5-165041

[51] Int. Cl.$^6$ .................................. A61K 31/24
[52] U.S. Cl. .................. 514/539; 514/562; 560/12; 562/427; 562/430
[58] Field of Search .............. 560/12; 562/427, 562/430; 514/539, 562; 424/451, 464, 489

[56] References Cited

U.S. PATENT DOCUMENTS 4,258,058  3/1981  Witte et al. .
4,443,477  4/1984  Witte et al. .
4,948,809  8/1990  Witte et al. .
4,981,873  1/1991  Witte et al. .
5,140,038  8/1992  Witte et al. .

FOREIGN PATENT DOCUMENTS 56-100757  8/1981  Japan .
62-84054   4/1987  Japan .
2-53762    2/1990  Japan .
2-160761   6/1990  Japan .

Primary Examiner—Samuel Barts
Attorney, Agent, or Firm—Greenblum & Bernstein, P.L.C.

[57] ABSTRACT

A benzenesulfonamide derivative represented by the following general formula:

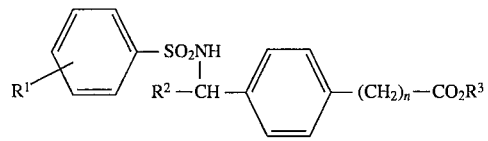

wherein $R^1$ represents a hydrogen atom, a lower alkyl group, a lower alkoxy group or a halogen atom; $R^2$ represents a $C_1$–$C_{10}$ straight- or branched-chain alkyl group, a $C_3$–$C_8$ cycloalkyl group which may be substituted with one or more $C_1$–$C_6$ alkyl groups on its ring, a $C_1$–$C_6$ alkyl group substituted with one or more $C_3$–$C_8$ cycloalkyl groups, 1-adamantylmethyl group, 2-norbornylmethyl group, or a $C_1$–$C_6$ alkyl group substituted with one or more phenyl groups whose benzene ring may have one or more substituents; $R^3$ represents a hydrogen atom or a lower alkyl group; and n is an integer of from 2 to 4, and a pharmacologically acceptable salt thereof. The present compounds have thromboxane $A_2$ antagonistic activity, leucotriene antagonistic activity and the like and useful as a platelet aggregation inhibitor, antithrombotic agent, antiasthmatic agent and antiallergic agent.

11 Claims, No Drawings

BENZENESULFONAMIDE DERIVATIVES AND USE THEREOF

This application is a 371 of PCT/JP93/01382 filed Sep. 29, 1993 and published as WO94/07848 Apr. 14, 1994.

TECHNICAL FIELD

The present invention relates to benzenesulfonamide derivatives and their pharmacologically acceptable salts having thromboxane $A_2$ antagonistic activity, leucotriene antagonistic activity and the like which are useful as platelet aggregation inhibitors, antithrombotic agents, antiasthmatic agents and antiallergic agents, and to uses thereof.

BACKGROUND ART

For example, the U.S. Pat. No. 4,258,058 discloses Sulotroban represented by the following formula and its derivatives:

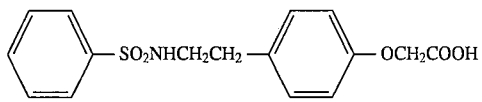

and the U.S. Pat. No. 4,443,477 discloses Daltroban represented by the following formula and its derivatives:

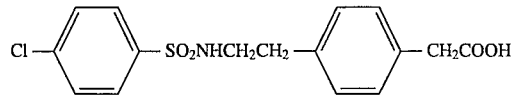

as benzenesulfonamide derivatives having thromboxane $A_2$ antagonistic activity. However, compounds structurally similar to the compounds of the present invention have never been known so far.

Thromboxane $A_2$ is a potent physiologically active substance which is biosynthesized from arachidonic acid in living bodies. The substance has platelet aggregation activity and contracting activity on smooth muscles such as bronchi and coronary arteries. Although the substance is rather important in living bodies, it is considered that its excessive production may cause various disorders such as thrombosis and asthma. Leucotriene is also a potent physiologically active substance biosynthesized from arachidonic acid. This substance induces various pharmacological effects such as contraction of respiratory tract smooth muscle, hyper-secretion of respiratory tract and hyper-permeation of blood vessels, and is considered to be significantly involved in pathopoiesis of asthma and allergic inflammation.

For these reasons, drugs having thromboxane $A_2$ antagonistic activity are expected to be useful as preventive and therapeutic agents for diseases associated with thromboxane $A_2$ such as, for example, ischemic heart diseases such as angina pectoris and myocardial infarction, cerebrovascular diseases, thrombosis, and asthma. Drugs having leucotriene antagonistic activity are also expected to be useful as preventive and therapeutic agents for diseases associated with leucotriene such as, for example, asthma and allergic inflammation. Although several thromboxane $A_2$ antagonists and leucotriene antagonists have been under clinical trials, they are not commercially available at present. Accordingly, further researches have been desired.

An object of the present invention is thus to provide medicaments having thromboxane $A_2$ antagonistic activity and leucotriene antagonistic activity and useful as drugs for preventive and therapeutic treatments for ischemic heart diseases such as angina pectoris and myocardial infarction, cerebrovascular diseases, thrombosis, and asthma, or useful as drugs for preventive and therapeutic treatments for asthma and allergic inflammation.

The inventors of the present invention conducted various studies under these circumstances and, as a result, found that the novel benzenesulfonamide derivatives of the present invention have inhibitory activities against thromboxane $A_2$ synthetase in addition to thromboxane $A_2$ antagonistic activities and leucotriene $D_4$ antagonistic activities. The inventors also found that they are highly useful as platelet aggregation inhibitors, antithrombotic agents, antiasthmatic agents and antiallergic agents. The present invention was achieved on the basis of these findings.

DISCLOSURE OF THE INVENTION

According to the present invention, there are provided novel benzenesulfonamide derivatives represented by the following general Formula (I):

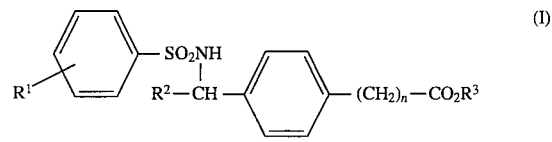

wherein $R^1$ represents a hydrogen atom, a lower alkyl group, a lower alkoxy group or a halogen atom; $R^2$ represents a $C_1$–$C_{10}$ straight- or branched-chain alkyl group, a $C_3$–$C_8$ cycloalkyl group which may be substituted with one or more $C_1$–$C_6$ alkyl groups on its ring, a $C_1$–$C_6$ alkyl group substituted with one or more $C_3$–$C_8$ cycloalkyl groups, 1-adamantylmethyl group, 2-norbornylmethyl group, or a $C_1$–$C_6$ alkyl group substituted with one or more phenyl groups whose benzene ring may have one or more substituents; $R^3$ represents a hydrogen atom or a lower alkyl group; and n is an integer of from 2 to 4, and pharmacologically acceptable salts thereof.

According to the present invention, there are also provided platelet aggregation inhibitors or antithrombotic agents, antiasthmatic agents, and antiallergic agents comprising one or more of the aforementioned benzenesulfonamide derivatives or pharmacologically acceptable salts thereof as active ingredients.

BEST MODE FOR CARRYING OUT THE INVENTION

According to a preferred embodiment of the present invention, there are provided compounds of the above-described general Formula (I) and their pharmacologically acceptable salts and the uses thereof, wherein $R^1$ represents a halogen atom; $R^2$ represents a $C_4$–$C_8$ straight- or branched-chain alkyl group or a $C_1$–$C_2$ alkyl group substituted with one or more phenyl groups whose benzene ring may have one or more substituents; $R^3$ represents a hydrogen atom or a lower alkyl group; and n is 3.

In addition, according to a particularly preferred embodiment of the present invention, there are provided compounds of the above-described general Formula (I) and their pharmacologically acceptable salts and the uses thereof, wherein $R^1$ represents a halogen atom; $R^2$ represents a $C_4$–$C_8$ straight- or branched-chain alkyl group, or benzyl group or phenethyl group which may be substituted with one or more halogen atoms or lower alkyl groups; $R^3$ represents a hydrogen atom or a lower alkyl group; and n is 3.

In the aforementioned general Formula (I), examples of the lower alkyl group represented by $R^1$ and $R^3$ include, for example, methyl group, ethyl group, n-propyl group, isopropyl group, n-butyl group, isobutyl group, sec-butyl group, and tert-butyl group. Examples of the lower alkoxy group represented by $R^1$ include, for example, methoxy group, ethoxy group, n-propoxy group, isopropoxy group, n-butoxy group, isobutoxy group, sec-butoxy group, and tert-butoxy group. As the halogen atom, fluorine atom, chlorine atom, bromine atom or iodine atom may be used.

Examples of the straight- or branched-chain $C_1$–$C_{10}$ alkyl group represented by $R^2$ include, for example, methyl group, ethyl group, n-propyl group, isopropyl group, n-butyl group, isobutyl group, sec-butyl group, tert-butyl group, n-pentyl group, isopentyl group, neopentyl group, tert-pentyl group, n-hexyl group, isohexyl group, 3,3-dimetylbutyl group, n-heptyl group, 5-methylhexyl group, 4,4-dimethylpentyl group, n-octyl group, 5,5-dimethylhexyl group, n-nonyl group, and n-decyl group. Examples of the $C_3$–$C_8$ cycloalkyl group which may be substituted with one or more $C_1$–$C_6$ alkyl groups on its ring include, for example, cyclopropyl group, cyclobutyl group, cyclopentyl group, 2-methylcyclopentyl group, 3-methylcyclopentyl group, cyclohexyl group, 4-methylcyclohexyl group, 4-ethylcyclohexyl group, 4-propylcyclohexyl group, 4-butylcyclohexyl group, 4-pentylcyclohexyl group, 4-hexylcyclohexyl group, 2-methylcyclohexyl group, 3-methylcyclohexyl group, cycloheptyl group, and cyclooctyl group. Examples of the $C_1$–$C_6$ alkyl group substituted with one ore more $C_3$–$C_8$ cycloalkyl groups include, for example, cyclopropylmethyl group, cyclobutylmethyl group, cyclopentylmethyl group, 2-cyclopentylethyl group, cyclohexylmethyl group, 2-cyclohexylethyl group, 3-cyclohexylpropyl group, 4-cyclohexylbutyl group, 5-cyclohexylpentyl group, 6-cyclohexylhexyl group, cycloheptylmethyl group and cyclooctylmethyl group. In the $C_1$–$C_6$ alkyl group substituted with one or more phenyl groups whose benzene ring may have one or more substituents, examples of the substituents which may substitute on the benzene ring include, for example, alkyl groups such as methyl group, ethyl group, n-propyl group, isopropyl group, n-butyl group, isobutyl group, sec-butyl group, tert-butyl group, n-pentyl group, n-hexyl group, n-heptyl group, and n-octyl group; alkoxy groups such as methoxy group, ethoxy group, n-propoxy group, isopropoxy group, n-butoxy group, isobutoxy group, sec-butoxy group, tert-butoxy group, n-pentyloxy group, n-hexyloxy group, n-heptyloxy group, and n-octyloxy group; and halogen atoms such as fluorine atom, chlorine atom, bromine atom, and iodine atom. Examples of the $C_1$–$C_6$ alkyl group substituted with one ore more phenyl groups include, for example, benzyl group, phenethyl group, 3-phenylpropyl group, 4-phenylbutyl group, 5-phenylpentyl group and 6-phenylhexyl group.

Specific examples of the compounds according to the present invention include the following compounds. However, the present invention is not limited to these examples.

(1) methyl 4-[4-[1-(4-chlorophenylsulfonylamino)ethyl]phenyl]butyrate
(2) 4-[4-[1-(4-chlorophenylsulfonylamino)ethyl]phenyl]butyric acid
(3) methyl 4-[4-[1-(4-chlorophenylsulfonylamino)propyl]phenyl]butyrate
(4) 4-[4-[1-(4-chlorophenylsulfonylamino)propyl]phenyl]butyric acid
(5) methyl 4-[4-[1-(4-chlorophenylsulfonylamino)butyl]phenyl]butyrate
(6) 4-[4-[1-(4-chlorophenylsulfonylamino)butyl]phenyl]butyric acid
(7) methyl 4-[4-[1-(4-chlorophenylsulfonylamino)pentyl]phenyl]butyrate
(8) 4-[4-[1-(4-chlorophenylsulfonylamino)pentyl]phenyl]butyric acid
(9) methyl 4-[4-[1-(4-chlorophenylsulfonylamino)hexyl]phenyl]butyrate
(10) ethyl 4-[4-[1-(4-chlorophenylsulfonylamino)hexyl]phenyl]butyrate
(11) 4-[4-[1-(4-chlorophenylsulfonylamino)hexyl]phenyl]butyric acid
(12) methyl 4-[4-[1-(4-chlorophenylsulfonylamino)heptyl]phenyl]butyrate
(13) 4-[4-[1-(4-chlorophenylsulfonylamino)heptyl]phenyl]butyric acid
(14) methyl 4-[4-[1-(4-chlorophenylsulfonylamino)octyl]phenyl]butyrate
(15) 4-[4-[1-(4-chlorophenylsulfonylamino)octyl]phenyl]butyric acid
(16) methyl 4-[4-[1-(4-chlorophenylsulfonylamino)nonyl]phenyl]butyrate
(17) 4-[4-[1-(4-chlorophenylsulfonylamino)nonyl]phenyl]butyric acid
(18) methyl 4-[4-[1-(4-chlorophenylsulfonylamino)decyl]phenyl]butyrate
(19) 4-[4-[1-(4-chlorophenylsulfonylamino)decyl]phenyl]butyric acid
(20) methyl 4-[4-[1-(4-chlorophenylsulfonylamino)-2-methylpropyl]phenyl]butyrate
(21) 4-[4-[1-(4-chlorophenylsulfonylamino)-2-methylpropyl]phenyl]butyric acid
(22) methyl 4-[4-[1-(4-chlorophenylsulfonylamino)-3-methylbutyl]phenyl]butyrate
(23) 4-[4-[1-(4-chlorophenylsulfonylamino)-3-methylbutyl]phenyl]butyric acid
(24) methyl 4-[4-[1-(4-chlorophenylsulfonylamino)-4-methylpentyl]phenyl]butyrate
(25) 4-[4-[1-(4-chlorophenylsulfonylamino)-4-methylpentyl]phenyl]butyric acid
(26) methyl 4-[4-[1-(4-chlorophenylsulfonylamino)-3,3-dimethylbutyl]phenyl]butyrate
(27) 4-[4-[1-(4-chlorophenylsulfonylamino)-3,3-dimethylbutyl]phenyl]butyric acid
(28) methyl 4-[4-[(4-chlorophenylsulfonylamino)cyclopropylmethyl]phenyl]butyrate
(29) 4-[4-[(4-chlorophenylsulfonylamino)cyclopropylmethyl]phenyl]butyric acid
(30) methyl 3-[4-[(4-chlorophenylsulfonylamino)cyclopentylmethyl]phenyl]propionate
(31) 3-[4-[(4-chlorophenylsulfonylamino)cyclopentylmethyl]phenyl]propionic acid
(32) methyl 4-[4-[(4-chlorophenylsulfonylamino)cyclopentylmethyl]phenyl]butyrate
(33) ethyl 4-[4-[(4-chlorophenylsulfonylamino)cyclopentylmethyl]phenyl]butyrate
(34) 4-[4-[(4-chlorophenylsulfonylamino)cyclopentylmethyl]phenyl]butyric acid
(35) methyl 5-[4-[(4-chlorophenylsulfonylamino)cyclopentylmethyl]phenyl]valerate
(36) 5-[4-[(4-chlorophenylsulfonylamino)cyclopentylmethyl]phenyl]valeric acid
(37) methyl 4-[4-[cyclopentyl(phenylsulfonylamino)methyl]phenyl]butyrate
(38) 4-[4-[cyclopentyl(phenylsulfonylamino)methyl]phenyl]butyric acid
(39) methyl 4-[4-[cyclopentyl(4-fluorophenylsulfonylamino)methyl]phenyl]butyrate
(40) 4-[4-[cyclopentyl(4-fluorophenylsulfonylamino)methyl]phenyl]butyric acid

(41) methyl 4-[4-[(4-bromophenylsulfonylamino)cyclopentylmethyl]phenyl]butyrate
(42) 4-[4-[(4-bromophenylsulfonylamino)cyclopentylmethyl]phenyl]butyric acid
(43) methyl 4-[4-[cyclopentyl(p-tolylsulfonylamino)methyl]phenyl]butyrate
(44) 4-[4-[cyclopentyl(p-tolylsulfonylamino)methyl]phenyl]butyric acid
(45) methyl 4-[4-[cyclopentyl(4-methoxyphenylsulfonylamino)methyl]phenyl]butyrate
(46) 4-[4-[cyclopentyl(4-methoxyphenylsulfonylamino)methyl]phenyl]butyric acid
(47) methyl 3-[4-[(4-chlorophenylsulfonylamino)cyclohexylmethyl]phenyl]propionate
(48) 3-[4-[(4-chlorophenylsulfonylamino)cyclohexylmethyl]phenyl]propionic acid
(49) methyl 4-[4-[(4-chlorophenylsulfonylamino)cyclohexylmethyl]phenyl]butyrate
(50) 4-[4-[(4-chlorophenylsulfonylamino)cyclohexylmethyl]phenyl]butyric acid
(51) methyl 5-[4-[(4-chlorophenylsulfonylamino)cyclohexylmethyl]phenyl]valerate
(52) 5-[4-[(4-chlorophenylsulfonylamino)cyclohexylmethyl]phenyl]valeric acid
(53) methyl 4-[4-[(4-chlorophenylsulfonylamino)cycloheptylmethyl]phenyl]butyrate
(54) 4-[4-[(4-chlorophenylsulfonylamino)cycloheptylmethyl]phenyl]butyric acid
(55) methyl trans-4-[4-[(4-chlorophenylsulfonylamino)(4-methylcyclohexyl)methyl]phenyl]butyrate
(56) trans-4-[4-[(4-chlorophenylsulfonylamino)(4-methylcyclohexyl)methyl]phenyl]butyric acid
(57) methyl trans-4-[4-[(4-chlorophenylsulfonylamino)(4-pentylcyclohexyl)methyl]phenyl]butyrate
(58) trans-4-[4-[(4-chlorophenylsulfonylamino)(4-pentylcyclohexyl)methyl]phenyl]butyric acid
(59) methyl trans-4-[4-[(4-chlorophenylsulfonylamino)(4-hexylcyclohexyl)methyl]phenyl]butyrate
(60) trans-4-[4-[(4-chlorophenylsulfonylamino)(4-hexylcyclohexyl)methyl]phenyl]butyric acid
(61) methyl 4-[4-[1-(4-chlorophenylsulfonylamino)-2-cyclopropylethyl]phenyl]butyrate
(62) 4-[4-[1-(4-chlorophenylsulfonylamino)-2-cyclopropylethyl]phenyl]butyric acid
(63) methyl 4-[4-[1-(4-chlorophenylsulfonylamino)-2-cyclopentylethyl]phenyl]butyrate
(64) 4-[4-[1-(4-chlorophenylsulfonylamino)-2-cyclopentylethyl]phenyl]butyric acid
(65) methyl 4-[4-[1-(4-chlorophenylsulfonylamino)-2-cyclohexylethyl]phenyl]butyrate
(66) 4-[4-[1-(4-chlorophenylsulfonylamino)-2-cyclohexylethyl]phenyl]butyric acid
(67) methyl 4-[4-[1-(4-chlorophenylsulfonylamino)-3-cyclohexylpropyl]phenyl]butyrate
(68) 4-[4-[1-(4-chlorophenylsulfonylamino)-3-cyclohexylpropyl]phenyl]butyric acid
(69) methyl 4-[4-[1-(4-chlorophenylsulfonylamino)-4-cyclohexylbutyl]phenyl]butyrate
(70) 4-[4-[1-(4-chlorophenylsulfonylamino)-4-cyclohexylbutyl]phenyl]butyric acid
(71) methyl 4-[4-[1-(4-chlorophenylsulfonylamino)-5-cyclohexylpentyl]phenyl]butyrate
(72) 4-[4-[1-(4-chlorophenylsulfonylamino)-5-cyclohexylpentyl]phenyl]butyric acid
(73) methyl 4-[4-[1-(4-chlorophenylsulfonylamino)-6-cyclohexylhexyl]phenyl]butyrate
(74) 4-[4-[1-(4-chlorophenylsulfonylamino)-6-cyclohexylhexyl]phenyl]butyric acid
(75) methyl 4-[4-[1-(4-chlorophenylsulfonylamino)-7-cyclohexylheptyl]phenyl]butyrate
(76) 4-[4-[1-(4-chlorophenylsulfonylamino)-7-cyclohexylheptyl]phenyl]butyric acid
(77) methyl 4-[4-[1-(4-chlorophenylsulfonylamino)-2-cycloheptylethyl]phenyl]butyrate
(78) 4-[4-[1-(4-chlorophenylsulfonylamino)-2-cycloheptylethyl]phenyl]butyric acid
(79) methyl 4-[4-[2-(1-adamantyl)-1-(4-chlorophenylsulfonylamino)ethyl]phenyl]butyrate
(80) 4-[4-[2-(1-adamantyl)-1-(4-chlorophenylsulfonylamino)ethyl]phenyl]butyric acid
(81) methyl 4-[4-[1-(4-chlorophenylsulfonylamino)-2-(2-norbornyl)ethyl]phenyl]butyrate
(82) 4-[4-[1-(4-chlorophenylsulfonylamino)-2-(2-norbornyl)ethyl]phenyl]butyric acid
(83) methyl 3-[4-[1-(4-chlorophenylsulfonylamino)-2-phenylethyl]phenyl]propionate
(84) 3-[4-[1-(4-chlorophenylsulfonylamino)-2-phenylethyl]phenyl]propionic acid
(85) methyl 4-[4-[2-phenyl-1-(phenylsulfonylamino)ethyl]phenyl]butyrate
(86) 4-[4-[2-phenyl-1-(phenylsulfonylamino)ethyl]phenyl]butyric acid
(87) methyl 4-[4-[1-(4-fluorophenylsulfonylamino)-2-phenylethyl]phenyl]butyrate
(88) 4-[4-[1-(4-fluorophenylsulfonylamino)-2-phenylethyl]phenyl]butyric acid
(89) methyl 4-[4-[1-(4-chlorophenylsulfonylamino)-2-phenylethyl]phenyl]butyrate
(90) ethyl 4-[4-[1-(4-chlorophenylsulfonylamino)-2-phenylethyl]phenyl]butyrate
(91) 4-[4-[1-(4-chlorophenylsulfonylamino)-2-phenylethyl]phenyl]butyric acid
(92) methyl 4-[4-[1-(3-chlorophenylsulfonylamino)-2-phenylethyl]phenyl]butyrate
(93) 4-[4-[1-(3-chlorophenylsulfonylamino)-2-phenylethyl]phenyl]butyric acid
(94) methyl 4-[4-[1-(2-chlorophenylsulfonylamino)-2-phenylethyl]phenyl]butyrate
(95) 4-[4-[1-(2-chlorophenylsulfonylamino)-2-phenylethyl]phenyl]butyric acid
(96) methyl 4-[4-[1-(4-bromophenylsulfonylamino)-2-phenylethyl]phenyl]butyrate
(97) 4-[4-[1-(4-bromophenylsulfonylamino)-2-phenylethyl]phenyl]butyric acid
(98) methyl 4-[4-[1-(p-tolylsulfonylamino)-2-phenylethyl]phenyl]butyrate
(99) 4-[4-[1-(p-tolylsulfonylamino)-2-phenylethyl]phenyl]butyric acid
(100) methyl 4-[4-[1-(4-methoxyphenylsulfonylamino)-2-phenylethyl]phenyl]butyrate
(101) 4-[4-[1-(4-methoxyphenylsulfonylamino)-2-phenylethyl]phenyl]butyric acid
(102) methyl 5-[4-[1-(4-chlorophenylsulfonylamino)-2-phenylethyl]phenyl]valerate
(103) 5-[4-[1-(4-chlorophenylsulfonylamino)-2-phenylethyl]phenyl]valeric acid
(104) methyl 4-[4-[1-(4-chlorophenylsulfonylamino)-2-(2-fluorophenyl)ethyl]phenyl]butyrate
(105) 4-[4-[1-(4-chlorophenylsulfonylamino)-2-(2-fluorophenyl)ethyl]phenyl]butyric acid
(106) methyl 4-[4-[1-(4-chlorophenylsulfonylamino)-2-(3-fluorophenyl)ethyl]phenyl]butyrate
(107) 4-[4-[1-(4-chlorophenylsulfonylamino)-2-(3-fluorophenyl)ethyl]phenyl]butyric acid
(108) methyl 4-[4-[1-(4-chlorophenylsulfonylamino)-2-(4-fluorophenyl)ethyl]phenyl]butyrate (109) 4-[4-[1-(4-chlorophenylsulfonylamino)-2-(4-fluorophenyl)ethyl]phenyl]butyric acid
(110) methyl 4-[4-[2-(4-chlorophenyl)-1-(4-chlorophenylsulfonylamino)ethyl]phenyl]butyrate
(111) 4-[4-[2-(4-chlorophenyl)-1-(4-chlorophenylsulfonylamino)ethyl]phenyl]butyric acid
(112) methyl 4-[4-[1-(4-chlorophenylsulfonylamino)-2-(p-tolyl)ethyl]phenyl]butyrate
(113) 4-[4-[1-(4-chlorophenylsulfonylamino)-2-(p-tolyl)ethyl]phenyl]butyric acid
(114) methyl 4-[4-[1-(4-chlorophenylsulfonylamino)-2-(4-methoxyphenyl)ethyl]phenyl]butyrate
(115) 4-[4-[1-(4-chlorophenylsulfonylamino)-2-(4-methoxyphenyl)ethyl]phenyl]butyric acid
(116) methyl 4-[4-[1-(4-chlorophenylsulfonylamino)-3-phenylpropyl]phenyl]butyrate
(117) 4-[4-[1-(4-chlorophenylsulfonylamino)-3-phenylpropyl]phenyl]butyric acid
(118) methyl 4-[4-[1-(4-chlorophenylsulfonylamino)-4-phenylbutyl]phenyl]butyrate
(119) 4-[4-[1-(4-chlorophenylsulfonylamino)-4-phenylbutyl]phenyl]butyric acid
(120) methyl 4-[4-[1-(4-chlorophenylsulfonylamino)-5-phenylpentyl]phenyl]butyrate
(121) 4-[4-[1-(4-chlorophenylsulfonylamino)-5-phenylpentyl]phenyl]butyric acid
(122) methyl 4-[4-[1-(4-chlorophenylsulfonylamino)-6-phenylhexyl]phenyl]butyrate
(123) 4-[4-[1-(4-chlorophenylsulfonylamino)-6-phenylhexyl]phenyl]butyric acid
(124) methyl 4-[4-[1-(4-chlorophenylsulfonylamino)-7-phenylheptyl]phenyl]butyrate
(125) 4-[4-[1-(4-chlorophenylsulfonylamino)-7-phenylheptyl]phenyl]butyric acid
(126) methyl 4-[4-[3-(4-butylphenyl)-1-(4-chlorophenylsulfonylamino)propyl]phenyl]butyrate
(127) 4-[4-[3-(4-butylphenyl)-1-(4-chlorophenylsulfonylamino)propyl]phenyl]butyric acid
(128) methyl 4-[4-[1-(4-chlorophenylsulfonylamino)-3-(4-pentylphenyl)propyl]phenyl]butyrate
(129) 4-[4-[1-(4-chlorophenylsulfonylamino)-3-(4-pentylphenyl)propyl]phenyl]butyric acid
(130) methyl 4-[4-[1-(4-chlorophenylsulfonylamino)-3-(4-hexylphenyl)propyl]phenyl]butyrate
(131) 4-[4-[1-(4-chlorophenylsulfonylamino)-3-(4-hexylphenyl)propyl]phenyl]butyric acid
(132) methyl 4-[4-[1-(4-chlorophenylsulfonylamino)-3-(4-heptylphenyl)propyl]phenyl]butyrate
(133) 4-[4-[1-(4-chlorophenylsulfonylamino)-3-(4-heptylphenyl)propyl]phenyl]butyric acid
(134) methyl 4-[4-[3-(4-butoxyphenyl)-1-(4-chlorophenylsulfonylamino)propyl]phenyl]butyrate
(135) 4-[4-[3-(4-butoxyphenyl)-1-(4-chlorophenylsulfonylamino)propyl]phenyl]butyric acid
(136) methyl 4-[4-[1-(4-chlorophenylsulfonylamino)-3-(4-pentyloxyphenyl)propyl]phenyl]butyrate
(137) 4-[4-[1-(4-chlorophenylsulfonylamino)-3-(4-pentyloxyphenyl)propyl]phenyl]butyric acid
(138) methyl 4-[4-[1-(4-chlorophenylsulfonylamino)-3-(4-hexyloxyphenyl)propyl]phenyl]butyrate
(139) 4-[4-[1-(4-chlorophenylsulfonylamino)-3-(4-hexyloxyphenyl)propyl]phenyl]butyric acid
(140) methyl 4-[4-[1-(4-chlorophenylsulfonylamino)-3-(o-tolyl)propyl]phenyl]butyrate
(141) 4-[4-[1-(4-chlorophenylsulfonylamino)-3-(o-tolyl)propyl]phenyl]butyric acid
(142) methyl 4-[4-[1-(4-chlorophenylsulfonylamino)-3-(m-tolyl)propyl]phenyl]butyrate
(143) 4-[4-[1-(4-chlorophenylsulfonylamino)-3-(m-tolyl)propyl]phenyl]butyric acid
(144) methyl 4-[4-[1-(4-chlorophenylsulfonylamino)-3-(p-tolyl)propyl]phenyl]butyrate
(145) 4-[4-[1-(4-chlorophenylsulfonylamino)-3-(p-tolyl)propyl]phenyl]butyric acid
(146) methyl 4-[4-[3-(4-cholorophenyl)-1-(4-chlorophenylsulfonylamino)propyl]phenyl]butyrate
(147) 4-[4-[3-(4-cholorophenyl)-1-(4-chlorophenylsulfonylamino)propyl]phenyl]butyric acid
(148) methyl 4-[4-[1-(4-chlorophenylsulfonylamino)-3-(4-fluorophenyl)propyl]phenyl]butyrate
(149) 4-[4-[1-(4-chlorophenylsulfonylamino)-3-(4-fluorophenyl)propyl]phenyl]butyric acid
(150) methyl 4-[4-[1-(4-chlorophenylsulfonylamino)-3-(4-methoxyphenyl)propyl]phenyl]butyrate
(151) 4-[4-[1-(4-chlorophenylsulfonylamino)-3-(4-methoxyphenyl)propyl]phenyl]butyric acid
(152) (+)-4-[4-[1-(4-chlorophenylsulfonylamino)-2-methylpropyl]phenyl]butyric acid
(153) (−)-4-[4-[1-(4-chlorophenylsulfonylamino)-2-methylpropyl]phenyl]butyric acid
(154) (+)-4-[4-[(4-chlorophenylsulfonylamino)cyclopentylmethyl]phenyl]butyric acid
(155) (−)-4-[4-[(4-chlorophenylsulfonylamino)cyclopentylmethyl]phenyl]butyric acid
(156) (+)-4-[4-[(4-chlorophenylsulfonylamino)cyclohexylmethyl]phenyl]butyric acid
(157) (−)-4-[4-[(4-chlorophenylsulfonylamino)cyclohexylmethyl]phenyl]butyric acid
(158) (+)-4-[4-[1-(4-chlorophenylsulfonylamino)-2-phenylethyl]phenyl]butyric acid
(159) (−)-4-[4-[1-(4-chlorophenylsulfonylamino)-2-phenylethyl]phenyl]butyric acid
(160) methyl 5-[4-[1-(4-chlorophenylsulfonylamino)pentyl]phenyl]valerate
(161) 5-[4-[1-(4-chlorophenylsulfonylamino)pentyl]phenyl]valeric acid
(162) methyl 4-[4-[1-(phenylsulfonylamino)hexyl]phenyl]butyrate
(163) 4-[4-[1-(phenylsulfonylamino)hexyl]phenyl]butyric acid
(164) methyl 4-[4-[1-(4-bromophenylsulfonylamino)hexyl]phenyl]butyrate
(165) 4-[4-[1-(4-bromophenylsulfonylamino)hexyl]phenyl]butyric acid
(166) methyl 4-[4-[1-(4-fluorophenylsulfonylamino)hexyl]phenyl]butyrate
(167) 4-[4-[1-(4-fluorophenylsulfonylamino)hexyl]phenyl]butyric acid
(168) methyl 4-[4-[1-(p-tolylsulfonylamino)hexyl]phenyl]butyrate
(169) 4-[4-[1-(p-tolylsulfonylamino)hexyl]phenyl]butyric acid
(170) methyl 4-[4-[1-(4-methoxyphenylsulfonylamino)hexyl]phenyl]butyrate
(171) 4-[4-[1-(4-methoxyphenylsulfonylamino)hexyl]phenyl]butyric acid
(172) methyl 5-[4-[1-(4-chlorophenylsulfonylamino)hexyl]phenyl]valerate
(173) 5-[4-[1-(4-chlorophenylsulfonylamino)hexyl]phenyl]valeric acid
(174) methyl 5-[4-[1-(4-chlorophenylsulfonylamino)-4-methylpentyl]phenyl]valerate
(175) 5-[4-[1-(4-chlorophenylsulfonylamino)-4-methylpentyl]phenyl]valeric acid
(176) methyl 4-[4-[5-methyl-1-(phenylsulfonylamino)hexyl]phenyl]butyrate (177) 4-[4-[5-methyl-1-(phenylsulfonylamino)hexyl]phenyl]butyric acid
(178) methyl 4-[4-[1-(4-chlorophenylsulfonylamino)-5-methylhexyl]phenyl]butyrate
(179) 4-[4-[1-(4-chlorophenylsulfonylamino)-5-methylhexyl]phenyl]butyric acid
(180) methyl 4-[4-[1-(4-bromophenylsulfonylamino)-5-methylhexyl]phenyl]butyrate
(181) 4-[4-[1-(4-bromophenylsulfonylamino)-5-methylhexyl]phenyl]butyric acid
(182) methyl 4-[4-[1-(4-fluorophenylsulfonylamino)-5-methylhexyl]phenyl]butyrate
(183) 4-[4-[1-(4-fluorophenylsulfonylamino)-5-methylhexyl]phenyl]butyric acid
(184) methyl 5-[4-[1-(4-chlorophenylsulfonylamino)-5-methylhexyl]phenyl]valerate
(185) 5-[4-[1-(4-chlorophenylsulfonylamino)-5-methylhexyl]phenyl]valeric acid
(186) methyl 4-[4-[1-(4-chlorophenylsulfonylamino)-6-methylheptyl]phenyl]butyrate
(187) 4-[4-[1-(4-chlorophenylsulfonylamino)-6-methylheptyl]phenyl]butyric acid
(188) methyl 4-[4-[1-(4-chlorophenylsulfonylamino)-4,4-dimethylpentyl]phenyl]butyrate
(189) 4-[4-[1-(4-chlorophenylsulfonylamino)-4,4-dimethylpentyl]phenyl]butyric acid
(190) methyl 5-[4-[1-(4-chlorophenylsulfonylamino)-4,4-dimethylpentyl]phenyl]valerate
(191) 5-[4-[1-(4-chlorophenylsulfonylamino)-4,4-dimethylpentyl]phenyl]valeric acid
(192) methyl 4-[4-[5,5-dimethyl-1-(phenylsulfonylamino)hexyl]phenyl]butyrate
(193) 4-[4-[5,5-dimethyl-1-(phenylsulfonylamino)hexyl]phenyl]butyric acid
(194) methyl 4-[4-[1-(4-chlorophenylsulfonylamino)-5,5-dimethylhexyl]phenyl]butyrate
(195) 4-[4-[1-(4-chlorophenylsulfonylamino)-5,5-dimethylhexyl]phenyl]butyric acid
(196) methyl 4-[4-[1-(4-bromophenylsulfonylamino)-5,5-dimethylhexyl]phenyl]butyrate
(197) 4-[4-[1-(4-bromophenylsulfonylamino)-5,5-dimethylhexyl]phenyl]butyric acid
(198) methyl 4-[4-[5,5-dimethyl-1-(4-fluorophenylsulfonylamino)hexyl]phenyl]butyrate
(199) 4-[4-[5,5-dimethyl-1-(4-fluorophenylsulfonylamino)hexyl]phenyl]butyric acid
(200) methyl 5-[4-[1-(4-chlorophenylsulfonylamino)-5,5-dimethylhexyl]phenyl]valerate
(201) 5-[4-[1-(4-chlorophenylsulfonylamino)-5,5-dimethylhexyl]phenyl]valeric acid
(202) methyl 4-[4-[1-(4-chlorophenylsulfonylamino)-6,6-dimethylheptyl]phenyl]butyrate
(203) 4-[4-[1-(4-chlorophenylsulfonylamino)-6,6-dimethylheptyl]phenyl]butyric acid
(204) methyl 4-[4-[1-(4-chlorophenylsulfonylamino)-3-cyclopentylpropyl]phenyl]butyrate
(205) 4-[4-[1-(4-chlorophenylsulfonylamino)-3-cyclopentylpropyl]phenyl]butyric acid
(206) methyl 5-[4-[1-(4-chlorophenylsulfonylamino)-2-cyclohexylethyl]phenyl]valerate
(207) 5-[4-[1-(4-chlorophenylsulfonylamino)-2-cyclohexylethyl]phenyl]valeric acid
(208) methyl 4-[4-[1-(4-chlorophenylsulfonylamino)-3-(3-fluorophenyl)propyl]phenyl]butyrate
(209) 4-[4-[1-(4-chlorophenylsulfonylamino)-3-(3-fluorophenyl)propyl]phenyl]butyric acid
(210) (+)-4-[4-[1-(4-chlorophenylsulfonylamino)hexyl]phenyl]butyric acid
(211) (−)-4-[4-[1-(4-chlorophenylsulfonylamino)hexyl]phenyl]butyric acid
(212) methyl 4-[4-[1-(4-fluorophenylsulfonylamino)pentyl]phenyl]butyrate
(213) 4-[4-[1-(4-fluorophenylsulfonylamino)pentyl]phenyl]butyric acid
(214) methyl 4-[4-[1-(4-bromophenylsulfonylamino)pentyl]phenyl]butyrate
(215) 4-[4-[1-(4-bromophenylsulfonylamino)pentyl]phenyl]butyric acid
(216) methyl 4-[4-[1-(4-fluorophenylsulfonylamino)heptyl]phenyl]butyrate
(217) 4-[4-[1-(4-fluorophenylsulfonylamino)heptyl]phenyl]butyric acid
(218) methyl 4-[4-[1-(4-bromophenylsulfonylamino)heptyl]phenyl]butyrate
(219) 4-[4-[1-(4-bromophenylsulfonylamino)heptyl]phenyl]butyric acid
(220) methyl 4-[4-[1-(4-fluorophenylsulfonylamino)-4-methylpentyl]phenyl]butyrate
(221) 4-[4-[1-(4-fluorophenylsulfonylamino)-4-methylpentyl]phenyl]butyric acid
(222) methyl 4-[4-[1-(4-bromophenylsulfonylamino)-4-methylpentyl]phenyl]butyrate
(223) 4-[4-[1-(4-bromophenylsulfonylamino)-4-methylpentyl]phenyl]butyric acid
(224) methyl 4-[4-[1-(4-fluorophenylsulfonylamino)-6-methylheptyl]phenyl]butyrate
(225) 4-[4-[1-(4-fluorophenylsulfonylamino)-6-methylheptyl]phenyl]butyric acid
(226) methyl 4-[4-[1-(4-bromophenylsulfonylamino)-6-methylheptyl]phenyl]butyrate
(227) 4-[4-[1-(4-bromophenylsulfonylamino)-6-methylheptyl]phenyl]butyric acid
(228) methyl 4-[4-[1-(4-fluorophenylsulfonylamino)-4,4-dimethylpentyl]phenyl]butyrate
(229) 4-[4-[1-(4-fluorophenylsulfonylamino)-4,4-dimethylpentyl]phenyl]butyric acid
(230) methyl 4-[4-[1-(4-bromophenylsulfonylamino)-4,4-dimethylpentyl]phenyl]butyrate
(231) 4-[4-[1-(4-bromophenylsulfonylamino)-4,4-dimethylpentyl]phenyl]butyric acid
(232) methyl 4-[4-[1-(4-fluorophenylsulfonylamino)-6,6-dimethylheptyl]phenyl]butyrate
(233) 4-[4-[1-(4-fluorophenylsulfonylamino)-6,6-dimethylheptyl]phenyl]butyric acid
(234) methyl 4-[4-[1-(4-bromophenylsulfonylamino)-6,6-dimethylheptyl]phenyl]butyrate
(235) 4-[4-[1-(4-bromophenylsulfonylamino)-6,6-dimethylheptyl]phenyl]butyric acid
(236) methyl 4-[4-[1-(4-bromophenylsulfonylamino)-2-(4-fluorophenyl)ethyl]phenyl]butyrate
(237) 4-[4-[1-(4-bromophenylsulfonylamino)-2-(4-fluorophenyl)ethyl]phenyl]butyric acid
(238) methyl 4-[4-[1-(4-bromophenylsulfonylamino)-2-(3-fluorophenyl)ethyl]phenyl]butyrate
(239) 4-[4-[1-(4-bromophenylsulfonylamino)-2-(3-fluorophenyl)ethyl]phenyl]butyric acid
(240) methyl 4-[4-[2-(4-chlorophenyl)-1-(4-fluorophenylsulfonylamino)ethyl]phenyl]butyrate
(241) 4-[4-[2-(4-chlorophenyl)-1-(4-fluorophenylsulfonylamino)ethyl]phenyl]butyric acid
(242) methyl 4-[4-[2-(4-chlorophenyl)-1-(4-bromophenylsulfonylamino)ethyl]phenyl]butyrate
(243) 4-[4-[2-(4-chlorophenyl)-1-(4-bromophenylsulfonylamino)ethyl]phenyl]butyric acid
(244) methyl 4-[4-[2-(4-bromophenyl)-1-(4-chlorophenylsulfonylamino)ethyl]phenyl]butyrate (245) 4-[4-[2-(4-bromophenyl)-1-(4-chlorophenylsulfonylamino)ethyl]phenyl]butyric acid
(246) methyl 4-[4-[1-(4-fluorophenylsulfonylamino)-2-(p-tolyl)ethyl]phenyl]butyrate
(247) 4-[4-[1-(4-fluorophenylsulfonylamino)-2-(p-tolyl)ethyl]phenyl]butyric acid
(248) methyl 4-[4-[1-(4-bromophenylsulfonylamino)-2-(p-tolyl)ethyl]phenyl]butyrate
(249) 4-[4-[1-(4-bromophenylsulfonylamino)-2-(p-tolyl)ethyl]phenyl]butyric acid
(250) methyl 4-[4-[1-(4-fluorophenylsulfonylamino)-3-phenylpropyl]phenyl]butyrate
(251) 4-[4-[1-(4-fluorophenylsulfonylamino)-3-phenylpropyl]phenyl]butyric acid
(252) methyl 4-[4-[1-(4-bromophenylsulfonylamino)-3-phenylpropyl]phenyl]butyrate
(253) 4-[4-[1-(4-bromophenylsulfonylamino)-3-phenylpropyl]phenyl]butyric acid Among these compounds, preferred compounds are Compound Nos. 7–13, 24, 25, 87–91, 96, 97, 106–113, 116, 117, 164–167, 178, 179, 186–189, 194, 195, 202, and 203. Particularly preferred compounds are Compound Nos. 8, 11, 91, 97, 107, 111, 113, 165, 167, 179, and 187.

Among the aforementioned compounds of the present invention represented by general Formula (I), the compounds wherein $R^3$ is a hydrogen atom may optionally be converted into pharmacologically acceptable salts, and the resulting salts may further be converted into free acids.

Examples of the pharmaceutically acceptable salts of the aforementioned compounds of the present invention represented by the general Formula (I) include alkali addition salts. Examples include inorganic alkali salts such as sodium, potassium, calcium, and ammonium salts or salts of organic bases such as trimethylamine, triethylamine, pyrrolidine, piperidine, piperazine, and N-methylmorpholine.

The compounds of the present invention represented by the above-described Formula (I) may exist as optical isomers or stereoisomers due to asymmetric carbon atoms. These isomers as well as their mixtures fall within the scope of the present invention.

The novel benzenesulfonamide derivatives of the present invention represented by the above-described general Formula (I) may be prepared by the methods set out below. However, processes for preparing the compounds are not limited to these methods.

According to the first embodiment of the methods for preparing the compounds of the present invention, the compounds represented by the above-described general Formula (I) can be prepared by reacting an amine derivative represented by the following general Formula (II):

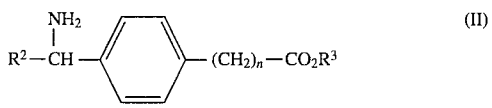

wherein $R^2$, $R^3$ and n are the same as those set out above with a sulfonyl chloride derivative represented by the following general Formula (III):

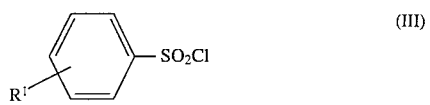

wherein $R^1$ is the same as that set out above, in a solvent in the presence of a base, and optionally hydrolyzing its ester group.

Any solvents may be used to react the compounds of the general Formula (II) with the compounds of the general Formula (III) so far that they do not affect the reaction. Examples include etheric solvents such as diethyl ether, tetrahydrofuran and 1,4-dioxane; halogenated hydrocarbonic solvents such as chloroform, methylene chloride and 1,2-dichloroethane; aromatic hydrocarbonic solvents such as benzene and toluene; aprotic polar solvents such as acetonitrile, N,N-dimethylformamide and dimethyl sulfoxide.

Examples of the base used for the reaction include, for example, organic bases such as triethylamine, diisopropylethylamine, 1,8-diazabicyclo[5.4.0]-7-undecene and pyridine, and inorganic bases such as sodium carbonate, potassium carbonate, sodium hydrogen carbonate and potassium hydrogen carbonate. The reaction may be carried out at a temperature of from 0° C. to the reflux temperature of a solvent. In addition, the hydrolysis reaction of the ester may be carried out by using a base or an acid in an aqueous solvent.

The solvent used for the reaction may be water alone. However, it is preferable to use water mixed with a solvent such as methanol, ethanol, n-propanol, isopropanol, n-butanol, acetone, tetrahydrofuran and 1,4-dioxane.

Examples of the base used for this reaction include sodium hydroxide, potassium hydroxide, sodium carbonate and potassium carbonate, and examples of the acid include hydrochloric acid, hydrobromic acid and sulfuric acid. The reaction may be carried out at a temperature of from 0° C. to the reflux temperature of a solvent.

The amine derivatives represented by the above-described general Formula (II) used as starting materials in the present process for preparation are novel compounds and may be prepared, for example, according to the following processes. The details are shown as References in Examples.

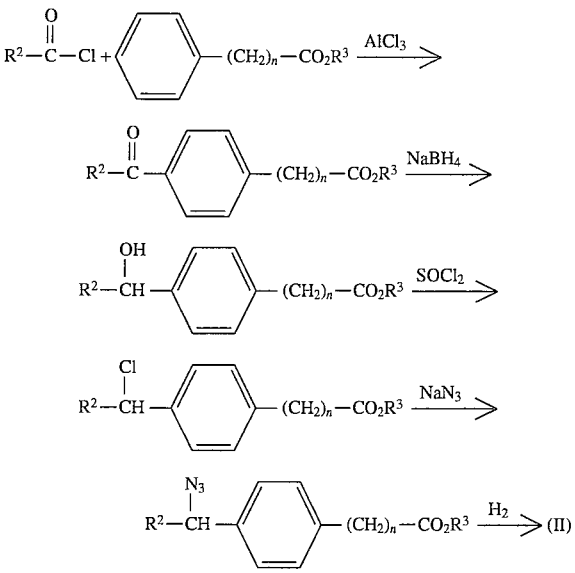

(In the above scheme, , $R^2$, $R^3$ and n are the same as those set out above.)

According to the second embodiment for preparing the compounds of the present invention, the compounds represented by the above-described general Formula (I) wherein $R^3$ is a hydrogen atom can be converted to their (+)- or (−)-optical isomers by treating racemates with optically active bases to form their salts and subjecting the salts to fractional crystallizations.

For example, quinidine, hydroquinidine, quinine, brucine, cinchonidine, cinchonine, ephedrine, (S)-(−)-1-phenylethylamine, (R)-(+)-1-phenylethylamine, (R)-(−)-2-amino-1-butanol, (S)-(+)-2-amino-1-butanol, (1R,2S)-(−)-2-amino-1,2-diphenylethanol, (1S,2R)-(+)-2-amino-1,2-diphenylethanol, (−)-cis-2-benzylaminocyclohexanemethanol, (+)-cis-2-benzylaminocyclohexanemethanol, (R)-(+)-1-(p-tolyl)ethylamine, (S)-(−)-1-(p-tolyl)ethylamine, (S)-(+)-α-methyl-4-nitrobenzylamine, (R)-(−)-α-methyl-4-nitrobenzylamine, (S)-(−)-1-(1-naphthyl)ethylamine, (R)-(+)-1-(1-naphthyl) ethylamine, L-phenylalaninol, L-(+)-lysine, L-(+)-arginine may be used as the optically active base used for the present preparation method.

Examples of the solvent used for the optical resolution include, for example, water; lower alcoholic solvents such as methanol, ethanol and isopropanol; halogenated hydrocarbonic solvents such as chloroform, dichloromethane, dichloroethane and carbon tetrachloride; ketone solvents such as acetone and methyl ethyl ketone; etheric solvents such as ether, diisopropyl ether and dioxane; aromatic hydrocarbonic solvents such as benzene, toluene and xylene; saturated hydrocarbonic solvents such as hexane, pentane and cyclohexane; nitrile solvents such as acetonitrile; ester solvents such as ethyl acetate and ethyl formate; amide solvents such as N,N-dimethylformamide and N,N-dimethylacetamide; organic solvents such as dimethyl sulfoxide and nitromethane; and mixtures thereof. The treatment with the optically active base may be carried out at from 0° C. to a temperature under slight heating.

Pharmaceutical compositions comprising as an active ingredient the novel benzenesulfonamide derivatives represented by the above-described general Formula (I) or pharmaceutically acceptable salts thereof thus prepared may be manufactured in the forms of orally administrable formulations such as capsules, tablets, subtilized granules, granules, powders and syrups, or injections for administrations to patients. These pharmaceutical compositions may be prepared in a conventional manner by adding pharmacologically and pharmaceutically acceptable additives. More specifically, for orally administrable formulations, pharmaceutical ingredients such as, for example, excipients such as lactose, D-mannitol, corn starch and crystalline cellulose; disintegrators such as carboxymethylcellulose and calcium carboxymethylcellulose; binders such as hydroxypropylcellulose, hydroxypropylmethylcellulose and polyvinylpyrrolidone; lubricants such as magnesium stearate and talc; and coating agents such as hydroxypropylmethylcellulose, saccharose and titanium oxide may be used. For injections, solubilizers or dissolving agents for preparing formulations in the form of aqueous compositions or compositions dissolved upon use such as distilled water for injections, physiological saline and propylene glycol; pH adjusting agents such as inorganic or organic acids and bases; isotonic agents such as sodium chloride, glucose and glycerin; and stabilizers may be used.

Dose of the compounds of the present invention for a patient to be treated may generally be about from 1 to 1,000 mg for oral administration and about from 1 to 500 mg for parenteral administration per day for an adult patient, which may depend on the conditions of the patient.

Pharmacological Action

As examples of excellent pharmacological actions exhibited by the compounds of the present invention, each of test results relating to thromboxane $A_2$ antagonistic effect, inhibitory effect on broncho-constriction, inhibitory effect on thromboxane $A_2$ synthetase, and leukotriene $D_4$ antagonistic effect will be set out below.

Daltroban was used as a reference drug.

Experiment 1: Thromboxane $A_2$ antagonistic effect

Blood was collected from the abdominal aorta of guinea-pigs (about 400 g wt.) into 1/10 volume of 3.8% sodium citrate, and then platelet-rich plasma (PRP: $6 \times 10^5$ cells/μl) was obtained by centrifugation. A cuvette was filled with PRP 190 μl and set in an aggregometer (Hema Tracer I; Niko Bioscience). Incubation was carried out for 2 min. at 37° C. after the addition of 1 μl of dimethyl sulfoxide solution of test compounds. To the PRP, 10 μl of U-46619 (Cayman), a thromboxane $A_2$/prostaglandin $H_2$ receptor agonist and potent platelet aggregation inducer, was added at the final concentration of 2 μg/ml, and platelet aggregation was measured by an aggregometer. $IC_{50}$ values (concentrations which produced 50% inhibition against platelet aggregation) are shown in Table 1.

TABLE 1

Thromboxane $A_2$ receptor antagonistic effect

| Test compound | $IC_{50}$ (μM) | Test compound | $IC_{50}$ (μM) |
| --- | --- | --- | --- |
| Example 62 | 0.050 | Example 89 | 0.032 |
| Example 64 | 0.16 | Example 90 | 0.32 |
| Example 66 | 0.32 | Example 91 | 0.32 |
| Example 67 | 0.40 | Example 92 | 0.32 |
| Example 69 | 0.20 | Example 93 | 0.32 |
| Example 70 | 0.32 | Example 94 | 0.063 |
| Example 71 | 0.40 | Example 95 | 0.16 |
| Example 72 | 0.32 | Example 96 | 0.63 |
| Example 73 | 0.25 | Example 97 | 0.32 |
| Example 74 | 0.32 | Example 98 | 0.32 |
| Example 75 | 0.32 | Example 99 | 0.32 |
| Example 78 | 0.32 | Example 100 | 0.79 |
| Example 79 | 0.32 | Example 107 | 0.25 |
| Example 80 | 1.0 | Example 108 | 0.50 |
| Example 82 | 0.40 | Example 113 | 0.40 |
| Example 85 | 0.40 | Example 114 | 0.32 |
| Example 86 | 0.25 | Example 115 | 0.32 |
| Example 87 | 0.32 | Example 116 | 0.50 |
| Example 88 | 0.32 | Reference compound | 2.0 |

The compounds of the present invention exhibited higher antagonistic effect on thromboxane $A_2$ receptor compared to the reference compound.

Experiment 2: Inhibitory effect on broncho-constriction induced by U-46619

Airway resistance was evaluated according to the method of Konzett-Roessler [Naunyn-Schmiedberg's Arch. Exp. Path. Pharmak., Vol. 195, 71 (1940)]. Male hartley guinea-pigs (about 400 g wt.) were anesthetized with urethane (1.5 g/kg, i.p.) and ventilated by an artificial respirator (Model 683; Harvard). At that time, overflowed air volume above the pressure of about 12 cm $H_2O$ was measured by using a sensor (Model 7020; Ugo basile) and the value was used as an index of broncho-constriction. 0.3 mg/kg (5 ml/kg) of test compounds suspended in 5% gum Arabic was administered orally to Guinea-pigs fasted beforehand for 24 hr. After 2 hrs, U-46619 (4 μg/kg; Cayman) was administered through the cervical vein, and then maximal response was measured. Inhibitory rates compared to the reference group were calculated based on the response rate normalized by the complete closure as 100%. The results are shown in Table 2.

TABLE 2

Inhibitory effect on broncho-constriction induced by U-46619

| Test compound | Inhibition rate (%) | Test compound | Inhibition rate (%) |
| --- | --- | --- | --- |
| Example 66 | 85 | Example 97 | 88 |
| Example 67 | 86 | Example 98 | 84 |
| Example 79 | 55 | Reference compound | 18 |
| Example 96 | 89 | | |

The compounds of the present invention exhibited higher inhibitory effects on the broncho-constriction induced by U-46619 compared to the reference compound.

Experiment 3: Inhibitory effect on thromboxane $A_2$ synthetase

100 μg/ml (285 μl) of the commercially available human platelet membrane fraction (RAN) as a source of thromboxane $A_2$ synthetase, dimethyl sulfoxide solution of test compounds (10 μl) and 100 μg/ml (5 μl) of prostaglandin $H_2$ (Cayman) were mixed and reaction was carried out for 3 min at 25° C. Amount of thromboxane $B_2$, a stable metabolite derived from thromboxane $A_2$ produced, was measured by RIA method ($TXB_2$ quantification kit; NEN). Concentrations which produce 50% inhibition of the enzyme activity ($IC_{50}$ values) are shown in Table 3.

TABLE 3

Inhibitory effect on thromboxane $A_2$ synthetase

| Test compound | $IC_{50}$ (μM) | Test compound | $IC_{50}$ (μM) |
|---|---|---|---|
| Example 62 | 4.0 | Example 73 | 1.6 |
| Example 63 | 2.0 | Example 74 | 3.2 |
| Example 69 | 2.0 | Reference compound | 40 |

The compounds of the present invention exhibited higher inhibitory effects on thromboxane $A_2$ synthetase compared to the reference compound.

Experiment 4: Leukotriene $D_4$ antagonistic effect

According to an ordinary method, tracheas were isolated from male Hartley guinea-pigs, and ring specimens of approximately 2 cm length were prepared. These specimens were suspended isotonically in organ baths that contained Krebs solution at 37° C. under a resting tension of 0.5 g. After repeated contractions with acetylcholine ($1 \times 10^{-6}$M; Ovisot for injection, Daiichi Seiyaku), and the first concentration-response curves was obtained by cummulative applications of leukotriene $D_4$ (ULTRA FINE) into the organ baths. After treatments with test compounds at adequate concentrations for 30 min, the second concentration-response curves were obtained in the same manner as first applications. $pK_B$ values were calculated using these two concentration-response curves according to the method of Schild [Pharmacological Review, Vol. 9, 242 (1957)]. Indomethacin ($3 \times 10^{-6}$M; Sigma) was added beforehand to the organ bath to eliminate possible affections by thromboxane $A_2$ and prostaglandin produced by stimulus of leukotriene $D_4$ [Japan J. Pharmacol., Vol. 60, 227 (1992)]. The results are shown in Table 4.

TABLE 4

Leukotriene $D_4$ antagonistic effect

| Test compound | $pK_B$ | Test compound | $pK_B$ |
|---|---|---|---|
| Example 66 | 6.1 | Example 96 | 6.0 |
| Example 67 | 6.7 | Example 97 | 5.9 |
| Example 71 | 6.7 | Example 98 | 6.4 |
| Example 74 | 6.3 | Example 99 | 6.9 |
| Example 75 | 6.4 | Example 102 | 6.7 |
| Example 76 | 6.7 | Example 106 | 6.9 |
| Example 77 | 6.2 | Example 107 | 7.0 |
| Example 78 | 6.0 | Example 108 | 6.8 |
| Example 79 | 7.0 | Example 113 | 7.4 |
| Example 80 | 6.9 | Example 116 | 6.7 |
| Example 84 | 6.7 | Example 117 | 6.6 |
| Example 85 | 6.8 | Reference compound | <4 |
| Example 95 | 6.3 | | |

The reference compound was inactive in leukotriene $D_4$ antagonistic effect. On the other hand, the compounds of the present invention exhibited excellent leukotriene $D_4$ antagonistic effects.

Experiment 5: Inhibitory effect on broncho-constriction induced by leukotriene $D_4$ Airway resistance was evaluated according to the method of Konzett-Roessler [Naunyn-Schmiedberg's Arch. Exp. Path. Pharmak., Vol. 195, 71 (1940)]. After male Hartley guinea-pig fasted beforehand for 24 hr were anesthetized with urethane, overflowed air volume was measured under artificial ventilation as an index of broncho-constriction. 30 mg/kg (5 ml/kg) of test compounds suspended in 5% gum Arabic were administered orally to the rats. Leukotriene $D_4$ (1 μg/kg; ULTRA FINE) was administered through the cervical vein after 2 hr, and then values were measured at 2 min after the time when responses became maximum. Inhibitory rates compared to the control group were calculated based on the response rate normalized by the overflowed volume at complete closure as 100% broncho-constriction state. The results are shown in Table 5. Indomethacin (2 mg/kg, i.v.) and propranolol (1 mg/kg, i.v.) were administered at 10 min and 5 min before the administration of leukotriene $D_4$, respectively.

TABLE 5

Inhibitory effect on broncho-constriction induced by leukotriene $D_4$

| Test compound | Inhibition rate (%) | Test compound | Inhibition rate (%) |
|---|---|---|---|
| Example 66 | 81 | Example 102 | 50 |
| Example 67 | 80 | Example 104 | 83 |
| Example 71 | 68 | Example 105 | 82 |
| Example 80 | 60 | Example 106 | 58 |
| Example 96 | 43 | Example 107 | 83 |
| Example 97 | 56 | Example 108 | 82 |
| Example 98 | 57 | Reference compound | $\leq 0$ |
| Example 99 | 64 | | |

The reference compound exhibit no inhibitory effect on broncho-constriction induced by leukotriene $D_4$. On the other hand, the compounds of the present invention exhibited potent inhibitory effects on leukotriene $D_4$-induced bronchoconstriction.

EXAMPLES

The present invention will be further illustrated by the following References and Examples. However, the present invention is not limited to any specific details described in these examples.

Reference Example 1

Methyl 4-[4-(Phenylacetyl)phenyl]butyrate

To a solution of 25.0 g of methyl 4-phenylbutyrate in 100 ml of carbon disulfide, 37.3 g of anhydrous aluminium chloride was added and then a solution of 43.3 g of phenylacetyl chloride in 25 ml of carbon disulfide was added dropwise, and the mixture was stirred at room temperature for 3 hours. The reaction mixture was poured into ice-water and extracted with methylene chloride. The methylene chloride layer was washed with aqueous potassium carbonate solution, dried, and then the solvent was removed. The residue was purified by column chromatography on silica gel (methylene chloride:n-hexane=2:1→methylene chloride) to afford 27.3 g of colorless crystals. Recrystallization from isopropyl ether gave colorless flakes, mp 54°~54.5° C.

Analysis for $C_{19}H_{20}O_3$

Calculated C, 77.00; H, 6.80 Found C, 77.03; H, 6.80

Reference Example 2

Methyl 3-[4-(Phenylacetyl)phenyl]propionate

To a solution of 1.00 g of methyl 3-phenylpropionate in 6 ml of carbon disulfide, 1.62 g of anhydrous aluminium chloride was added under ice-cooling, and then 0.94 g of phenylacetyl chloride was added dropwise and stirring was continued at room temperature for 6 hours. The reaction mixture was poured into ice-water and extracted with methylene chloride. The methylene chloride layer was washed successively with water, aqueous potassium carbonate solution and water, dried, and then the solvent was removed under reduced pressure. The residue was purified by column chromatography on silica gel (methylene chloride:n-hexane=2:1) to afford 1.05 g of colorless crystals. Recrystallization from isopropyl ether gave colorless flakes, mp 77°~78° C.

Analysis for $C_{18}H_{18}O_3$

Calculated C, 76.57; H, 6.43 Found C, 76.59; H, 6.47

Reference Example 3

Methyl 5-[4-(Phenylacetyl)phenyl]valerate

To a solution of 5.12 g of methyl 5-phenylvalerate in 25 ml of carbon disulfide, 7.10 g of anhydrous aluminium chloride was added under ice-cooling, and then 4.11 g of phenylacetyl chloride was added dropwise and stirring was continued at room temperature for 6 hours. The reaction mixture was poured into ice-water and extracted with methylene chloride. The methylene chloride layer was washed successively with water, aqueous potassium carbonate solution and water, dried, and then the solvent was removed under reduced pressure. The residue was purified by column chromatography on silica gel (methylene chloride:n-hexane=2:1) to afford 5.45 g of colorless crystals. Recrystallization from isopropyl ether gave colorless flakes, mp 53.5°~54° C.

Analysis for $C_{20}H_{22}O_3$

Calculated C, 77.39; H, 7.14 Found C, 77.68; H, 7.24

The compounds of Reference Examples 4 through 42 shown in Tables 6 to 12 were obtained in the same manner as described in Reference Examples 1 to 3.

TABLE 6

| Reference Example No. | Compound | Appearance | mp | Analysis (upper:Calculated) (lower:Found) |
|---|---|---|---|---|
| 4 | Methyl 4-[4-[(2-Fluorophenyl)acetyl]phenyl]butyrate | colorless needles (i-Pr$_2$O) | 53~54° C. | $C_{19}H_{19}FO_3$<br>C, 72.60; H, 6.09<br>C, 72.59; H, 6.07 |
| 5 | Methyl 4-[4-[(3-Fluorophenyl)acetyl]phenyl]butyrate | colorless flakes (i-Pr$_2$O) | 49~51° C. | $C_{19}H_{19}FO_3$<br>C, 72.60; H, 6.09<br>C, 72.72; H, 6.06 |
| 6 | Methyl 4-[4-[(4-Fluorophenyl)acetyl]phenyl]butyrate | colorless needles (i-Pr$_2$O) | 84~86° C. | $C_{19}H_{19}FO_3$<br>C, 72.60; H, 6.09<br>C, 72.62; H, 6.19 |
| 7 | Methyl 4-[4-[(4-Chlorophenyl)acetyl]phenyl]butyrate | colorless needles (i-Pr$_2$O) | 103~105° C. | $C_{19}H_{19}ClO_3$<br>C, 68.98; H, 5.79<br>C, 69.13; H, 5.88 |
| 8 | Methyl 4-[4-[(p-Tolyl)acetyl]phenyl]butyrate | colorless flakes (i-Pr$_2$O) | 62.5~63° C. | $C_{20}H_{22}O_3$<br>C, 77.39; H, 7.14<br>C, 77.37; H, 7.36 |
| 9 | Methyl 4-(4-Decanoylphenyl)butyrate | colorless needles (n-Hexane) | 47.5~48.5° C. | $C_{21}H_{32}O_3$<br>C, 75.86; H, 9.70<br>C, 75.83; H, 9.98 |
| 10 | Methyl 4-[4-(6-Cyclohexylhexanoyl)phenyl]butyrate | colorless crystals (MeOH) | 42.5~44° C. | $C_{23}H_{34}O_3$<br>C, 77.05; H, 9.56<br>C, 77.04; H, 9.72 |

TABLE 7

| Reference Example No. | Compound Appearance | IR ν (liq) cm$^{-1}$ | NMR δ (CDCl$_3$) |
|---|---|---|---|
| 11 | Methyl 4-(4-Acetylphenyl)butyrate<br>pale brown oil | 1738, 1684 | 1.98(2H, qn, J=7.5Hz), 2.34(2H, t, J=7.5Hz), 2.59(3H, s), 2.72(2H, t, J=7.5Hz), 3.67(3H, s), 7.27(2H, d, J=8Hz), 7.89(2H, d, J=8Hz) |
| 12 | Methyl 4-(4-Propionylphenyl)butyrate<br>pale yellow oil | 1738, 1688 | 1.22(3H, t, J=7.5Hz), 1.98(2H, qn, J=7.5Hz), 2.34(2H, t, J=7.5Hz), 2.71(2H, t, J=7.5Hz), 2.98(2H, q, J=7.5Hz), 3.67(3H, s), 7.26(2H, d, J=8.5Hz), 7.89(2H, |

TABLE 7-continued

| Reference Example No. | Compound Appearance | IR ν (liq) cm⁻¹ | NMR δ (CDCl₃) |
|---|---|---|---|
| 13 | Methyl 4-(4-Butyryl-phenyl)butyrate colorless oil bp 148~151° C. (2 mmHg) | 1738, 1686 | d, J=8.5Hz) 1.00(3H, t, J=7.5Hz), 1.77(2H, sex, J=7.5Hz), 1.98(2H, qn, J=7.5Hz), 2.34(2H, t, J=7.5Hz), 2.71(2H, t, J=7.5Hz), 2.92(2H, t, J=7.5Hz), 3.67(3H, s), 7.26(2H, d, J=8Hz), 7.89(2H, d, J=8Hz) |
| 14 | Methyl 4-(4-Pentanoyl-phenyl)butyrate pale reddish brown oil | 1738, 1686 | 0.95(3H, t, J=7.5Hz), 1.41(2H, sex, J=7.5Hz), 1.72(2H, qn, J=7.5Hz), 1.98(2H, qn, J=7.5Hz), 2.34(2H, t, J=7.5Hz), 2.71(2H, t, J=7.5Hz), 2.94(2H, t, J=7.5Hz), 3.67(3H, s), 7.26(2H, d, J=8Hz), 7.89(2H, d, J=8Hz) |
| 15 | Methyl 4-(4-Hexanoyl-phenyl)butyrate colorless oil | 1738, 1684 | 0.91(3H, t, J=7Hz), 1.32–1.41(4H, m), 1.69–1.78(2H, m), 1.98(2H, qn, J=7.5Hz), 2.34(2H, t, J=7.5Hz), 2.71(2H, t, J=7.5Hz), 2.93(2H, t, J=7.5Hz), 3.67(3H, s), 7.26(2H, d, J=8Hz), 7.89(2H, d, J=8Hz) |
| 16 | Methyl 4-(4-Isovaleryl-phenyl)butyrate colorless oil | 1738, 1684 | 0.99(6H, d, J=7Hz), 1.98(2H, qn, J=7.5Hz), 2.28–2.32(1H, m), 2.34(2H, t, J=7.5Hz), 2.71(2H, t, J=7.5Hz), 2.81(2H, d, J=7Hz), 3.67(3H, s), 7.26(2H, d, J=8Hz), 7.88(2H, d, J=8Hz) |
| 17 | Methyl 4-[4-(4-Methyl-pentanoyl)phenyl]butyrate colorless oil | 1738, 1686 | 0.95(6H, d, J=6Hz), 1.60–1.69(3H, m), 1.98(2H, qn, J=7.5Hz), 2.34(2H, t, J=7.5Hz), 2.71(2H, t, J=7.5Hz), 2.94(2H, t, J=7.5Hz), 3.67(3H, s), 7.27(2H, d, J=8Hz), 7.89(2H, d, J=8Hz) |

TABLE 8

| Reference Example No. | Compound Appearance | IR ν (liq) cm⁻¹ | NMR δ (CDCl₃) |
|---|---|---|---|
| 18 | Methyl 4-[4-(3,3-Dimethyl-butyryl)phenyl]butyrate colorless oil | 1738, 1688, 1674 | 1.06(9H, s), 1.98(2H, qn, J=7.5Hz), 2.34(2H, t, J=7.5Hz), 2.71(2H, t, J=7.5Hz), 2.83(2H, s), 3.67(3H, s), 7.25(2H, d, J=8Hz), 7.87(2H, d, J=8Hz) |
| 19 | Methyl 4-[4-(Cyclopentyl-carbonyl)phenyl]butyrate yellow oil | 1738, 1680 | 1.61–1.77(4H, m), 1.88–1.93(4H, m), 1.98(2H, qn, J=7.5Hz), 2.34(2H, t, J=7.5Hz), 2.71(2H, t, J=7.5Hz), 3.67(3H, s), 3.69(1H, qn, J=8Hz), 7.26(2H, d, J=8Hz), 7.90(2H, d, J=8Hz) |
| 20 | Methyl 4-[4-(Cyclohexyl-carbonyl)phenyl]butyrate colorless oil | 1738, 1682 | 1.22–1.32(1H, m), 1.34–1.54(4H, m), 1.70–1.76(1H, m), 1.81–1.91(4H, m), 1.98(2H, qn, J=7.5Hz), 2.34(2H, t, J=7.5Hz), 2.71(2H, t, J=7.5Hz), 3.20–3.28(1H, m), 3.67(3H, s), 7.26(2H, d, J=8Hz), 7.87(2H, d, J=8Hz) |
| 21 | Methyl 4-[4-(Cycloheptyl-carbonyl)phenyl]butyrate pale brown oil | 1738, 1682 | 1.50–1.75(8H, m), 1.75–1.84(2H, m), 1.87–1.95(2H, m), 1.98(2H, qn, J=7.5Hz), 2.34(2H, t, J=7.5Hz), 2.71(2H, t, J=7.5Hz), 3.37–3.45(1H, m), 3.67(3H, s), 7.26(2H, d, J=8Hz), 7.86(2H, d, J=8Hz) |
| 22 | Methyl 4-[4-(Cyclopentyl-acetyl)phenyl]butyrate colorless oil | 1738, 1684 | 1.16–1.22(2H, m), 1.54–1.58(2H, m), 1.63–1.66(2H, m), 1.86–1.91(2H, m), 1.98(2H, qn, J=7.5Hz), 2.32–2.41(1H, m), 2.34(2H, t, J=7.5Hz), 2.71(2H, t, J=7.5Hz), 2.96(2H, d, J=7Hz), 3.67(3H, s), 7.26(2H, d, J=8Hz), 7.88(2H, d, J=8Hz) |
| 23 | Methyl 4-[4-(Cyclohexyl-acetyl)phenyl]butyrate pale brown oil | 1740, 1684 | 0.97–1.05(2H, m), 1.15–1.20(1H, m), 1.25–1.33(2H, m), 1.56–1.77(5H, m), 1.93–2.02(1H, m), 1.98(2H, qn, J=7.5Hz), 2.34(2H, t, J=7.5Hz), 2.71(2H, t, J=7.5Hz), 2.79(2H, d, J=7Hz), 3.67(3H, |

TABLE 8-continued

| Reference Example No. | Compound Appearance | IR ν (liq) cm$^{-1}$ | NMR δ (CDCl$_3$) |
|---|---|---|---|
| | | | s), 7.26(2H, d, J=8.5Hz), 7.87(2H, d, J=8.5Hz) |

TABLE 9

| Reference Example No. | Compound Appearance | IR ν (liq) cm$^{-1}$ | NMR δ (CDCl$_3$) |
|---|---|---|---|
| 24 | Methyl 4-[4-(3-Cyclohexyl-propionyl)phenyl]butyrate colorless oil | 1738, 1686 | 0.90–0.99(2H, m), 1.11–1.40(4H, m), 1.58–1.81(7H, m), 1.98(2H, qn, J=7.5Hz), 2.34(2H, t, J=7.5Hz), 2.71(2H, t, J=7.5Hz), 2.95(2H, t, J=7.5Hz), 3.67(3H, s), 7.26(2H, d, J=8Hz), 7.88(2H, d, J=8Hz) |
| 25 | Methyl 4-[4-(4-Cyclohexyl-butyryl)phenyl]butyrate pale yellow oil | 1738, 1686 | 0.85–0.95(2H, m), 1.10–1.30(6H, m), 1.02–1.77(7H, m), 1.98(2H, qn, J=7.5Hz), 2.34(2H, t, J=7.5Hz), 2.71(2H, t, J=7.5Hz), 2.91(2H, t, J=7.5Hz), 3.67(3H, s), 7.26(2H, d, J=8Hz), 7.88(2H, d, J=8Hz) |
| 26 | Methyl 4-[4-(5-Cyclohexyl-pentanoyl)phenyl]butyrate colorless needles (MeOH) mp 50.5~51.5° C. | (KBr) 1738, 1674 | 0.82–0.90(2H, m), 1.09–1.25(6H, m), 1.35–1.41(2H, m), 1.62–1.73(7H, m), 1.98(2H, qn, J=7.5Hz), 2.34(2H, t, J=7.5Hz), 2.71(2H, t, J=7.5Hz), 2.93(2H, t, J=7.5Hz), 3.67(3H, s), 7.26(2H, d, J=8.5Hz), 7.88(2H, d, J=8.5Hz) |
| 27 | Methyl trans-4-[4-(4-Methylcyclohexyl-carbonyl)phenyl]butyrate colorless oil | 1738, 1682 | 0.93(3H, d, J=7Hz), 1.02–1.12(2H, m), 1.36–1.48(1H, m), 1.48–1.58(2H, m), 1.79–1.86(2H, m), 1.86–1.92(2H, m), 1.98(2H, qn, J=7.5Hz), 2.34(2H, t, J=7.5Hz), 2.71(2H, t, J=7.5Hz), 3.17(1H, tt, J=12, 3Hz), 3.67(3H, s), 7.26(2H, d, J=8Hz), 7.87(2H, d, J=8Hz) |
| 28 | Methyl trans-4-[4-(4-Pentylcyclohexyl-carbonyl)phenyl]butyrate colorless needles (MeOH) mp 62~63° C. | (KBr) 1734, 1668 | 0.89(3H, t, J=7Hz), 0.99–1.09(2H, m), 1.18–1.35(9H, m), 1.45–1.56(2H, m), 1.84–1.94(4H, m), 1.98(2H, qn, J=7.5Hz), 2.34(2H, t, J=7.5Hz), 2.71(2H, t, J=7.5Hz), 3.19(1H, tt, J=12, 3Hz), 3.67(3H, s), 7.26(2H, d, J=8.5Hz), 7.87(2H, d, J=8.5Hz) |
| 29 | Methyl 4-[4-[(1-Adamantyl)-acetyl]phenyl]butyrate pale yellow oil | 1738, 1672 | 1.63–1.70(12H, m), 1.94–1.95(3H, m), 1.98(2H, qn, J=7.5Hz), 2.34(2H, t, J=7.5Hz), 2.69(3H, s), 2.71(2H, t, J=7.5Hz), 3.67(3H, s), 7.25(2H, d, J=8Hz), 7.87(2, H, d, J=8Hz) |

TABLE 10

| Reference Example No. | Compound Appearance | IR ν (liq) cm$^{-1}$ | NMR δ (CDCl$_3$) |
|---|---|---|---|
| 30 | Methyl 4-[4-[(2-Norbornyl)-acetyl]phenyl]butyrate pale brown oil | 1738, 1684 | 1.07–1.59(8H, m), 1.98(2H, qn, J=7.5Hz), 2.01–2.08(2H, m), 2.23(1H, s), 2.34(2H, t, J=7.5Hz), 2.71(2H, t, J=7.5Hz), 2.76(1H, dd, J=16, 7Hz), 2.94(1H, dd, J=16, 7Hz), 3.67(3H, s), 7.26(2H, d, J=8Hz), 7.87(2H, d, J=8Hz) |
| 31 | Methyl 5-(4-Pentanoyl-phenyl)valerate colorless oil | 1738, 1684 | 0.95(3H, t, J=7.5Hz), 1.41(2H, sex, J=7.5Hz), 1.64–1.75(6H, m), 2.30–2.38(2H, m), 2.64–2.73(2H, m), 2.94(2H, t, J=7.5Hz), 3.67(3H, s), 7.25(2H, d, J=8Hz), 7.88(2H, d, J=8Hz) |

TABLE 10-continued

| Reference Example No. | Compound Appearance | IR ν (liq) cm⁻¹ | NMR δ (CDCl₃) |
|---|---|---|---|
| 32 | Methyl 5-(4-Hexanoyl-phenyl)valerate colorless oil | 1740, 1684 | 0.91(3H, t, J=7Hz), 1.32–1.40(4H, m), 1.62–1.77(6H, m), 2.31–2.36(2H, m), 2.62–2.73(2H, m), 2.93(2H, t, J=7.5Hz), 3.66(3H, s), 7.25(2H, d, J=8Hz), 7.88(2H, d, J=8Hz) |
| 33 | Methyl 5-[4-(Cyclohexyl-acetyl)phenyl]valerate pale brown oil | 1738, 1684 | 0.96–1.05(2H, m), 1.11–1.22(1H, m), 1.23–1.34(2H, m), 1.60–1.80(9H, m), 1.92–2.02(1H, m), 2.30–2.38(2H, m), 2.65–2.72(2H, m), 2.79(2H, d, J=6.5Hz), 3.67(3H, s), 7.25(2H, d, J=8.5Hz), 7.87(2H, d, J=8.5Hz) |
| 34 | Methyl 4-(4-Heptanoyl-phenyl)butyrate pale yellow oil | 1738, 1686 | 0.89(3H, t, J=7.5Hz), 1.28–1.42(6H, m), 1.72(2H, qn, J=7.5Hz), 1.98(2H, qn, J=7.5Hz), 2.34(2H, t, J=7.5Hz), 2.71(2H, t, J=7.5Hz), 2.93(2H, t, J=7.5Hz), 3.67(3H, s), 7.26(2H, d, J=8Hz), 7.89(2H, d, J=8Hz) |
| 35 | Methyl 4-(4-Octanoyl-phenyl)butyrate colorless needles (n-Hexane) mp 43–44.5° C. | 1738, 1684 | 0.88(3H, t, J=7Hz), 1.24–1.42(8H, m), 1.73(2H, qn, J=7.5Hz), 1.98(2H, qn, J=7.5Hz), 2.34(2H, t, J=7.5Hz), 2.71(2H, t, J=7.5Hz), 2.93(2H, t, J=7.5Hz), 3.67(3H, s), 7.26(2H, d, J=8Hz), 7.88(2H, d, J=8Hz) |

TABLE 11

| Reference Example No. | Compound Appearance | IR ν (liq) cm⁻¹ | NMR δ (CDCl₃) |
|---|---|---|---|
| 36 | Methyl 4-(4-Nonanoyl-phenyl)butyrate colorless needles (n-Hexane) mp 35–35.5° C. | 1744, 1688 | 0.88(3H, t, J=7Hz), 1.23–1.42(10H, m), 1.72(2H, qn, J=7.5Hz), 1.98(2H, qn, J=7.5Hz), 2.34(2H, t, J=7.5Hz), 2.71(2H, t, J=7.5Hz), 2.93(2H, t, J=7.5Hz), 3.67(3H, s), 7.26(2H, d, J=8Hz), 7.88(2H, d, J=8Hz) |
| 37 | Methyl 4-[4-(5-Methyl-hexanoyl)phenyl]butyrate pale brown oil | 1740, 1684 | 0.90(6H, d, J=6Hz), 1.24–1.28(2H, m), 1.55–1.64(1H, m), 1.73(2H, qn, J=7.5Hz), 1.98(2H, qn, J=7.5Hz), 2.34(2H, t, J=7.5Hz), 2.71(2H, t, J=7.5Hz), 2.92(2H, t, J=7.5Hz), 3.67(3H, s), 7.26(2H, d, J=8Hz), 7.88(2H, d, J=8Hz) |
| 38 | Methyl 4-[4-(6-Methyl-heptanoyl)phenyl]butyrate colorless oil | 1740, 1684 | 0.87(6H, d, J=6Hz), 1.18–1.26(2H, m), 1.33–1.41(2H, m), 1.48–1.60(1H, m), 1.71(2H, qn, J=7.5Hz), 1.98(2H, qn, J=7.5Hz), 2.34(2H, t, J=7.5Hz), 2.71(2H, t, J=7.5Hz), 2.94(2H, t, J=7.5Hz), 3.67(3H, s), 7.26(2H, d, J=8.5Hz), 7.89(2H, d, J=8.5Hz) |
| 39 | Methyl 4-[4-(4,4-Dimethyl-pentanoyl)phenyl]butyrate colorless oil | 1738, 1684 | 0.96(9H, s), 1.62–1.65(2H, m), 1.98(2H, qn, J=7.5Hz), 2.34(2H, t, J=7.5Hz), 2.71(2H, t, J=7.5Hz), 2.89–2.93(2H, m), 3.67(3H, s), 7.27(2H, d, J=8Hz), 7.89(2H, d, J=8Hz) |
| 40 | Methyl 4-[4-(5,5-Dimethyl-hexanoyl)phenyl]butyrate colorless oil | 1740, 1686 | 0.90(9H, s), 1.24–1.27(2H, m), 1.67–1.74(2H, m), 1.98(2H, qn, J=7.5Hz), 2.34(2H, t, J=7.5Hz), 2.71(2H, t, J=7.5Hz), 2.91(2H, t, J=7.5Hz), 3.67(3H, s), 7.26(2H, d, J=8.5Hz), 7.88(2H, d, J=8.5Hz) |
| 41 | Methyl 4-[4-(6,6-Dimethyl-heptanoyl)phenyl]butyrate colorless oil | 1742, 1686 | 0.87(9H, s), 1.20–1.28(2H, m), 1.31–1.37(2H, m), 1.70(2H, qn, J=7.5Hz), 1.98(2H, qn, J=7.5Hz), 2.34(2H, t, J=7.5Hz), 2.71(2H, t, J=7.5Hz), 2.95(2H, t, J=7.5Hz), 3.67(3H, s), 7.27(2H, d, J=8Hz), 7.89(2H, d, J=8Hz) |

TABLE 12

| Reference Example No. | Compound Appearance | I R ν (liq) cm$^{-1}$ | NMR δ (CDCl$_3$) |
|---|---|---|---|
| 42 | Methyl 4-[4-(3-Cyclopentyl-propionyl)phenyl]butyrate pale orange oil | 1742, 1680 | 1.10–1.20(2H, m), 1.50–1.55(2H, m), 1.55–1.65(2H, m), 1.74(2H, q, J=7.5Hz), 1.70–1.85(3H, m), 1.98(2H, qn, J=7.5Hz), 2.34(2H, t, J=7.5Hz), 2.71(2H, t, J=7.5Hz), 2.95(2H, t, J=7.5Hz), 3.67(3H, s), 7.26(2H, d, J=8Hz), 7.89(2H, d, J=8Hz) |

Reference Example 43

4-(4-Cinnamoylphenyl)butyric Acid

To a solution of 0.40 g of sodium hydroxide in 6 ml of water, a solution of 1.00 g of methyl 4-(4-acetylphenyl)butyrate in 2 ml of methanol was added under ice-cooling. Then, a solution of 0.48 g of benzaldehyde in 2 ml of methanol was added dropwise and stirring was continued at room temperature for 3 hours. The reaction mixture was diluted with water and acidified with dilute hydrochloric acid. Precipitated crystals were collected by filtration, washed successively with water and n-hexane to yield 0.94 g of colorless crystals. Recrystallization from 80% aqueous methanol gave colorless needles, mp 111°–112° C.

Analysis for $C_{19}H_{18}O_3$

Calculated C, 77.53; H, 6.16 Found C, 77.54; H, 6.22

The compounds of Reference Examples 44 through 50 shown in Table 13 were obtained in the same manner as described in Reference Example 43.

Reference Example 51

Methyl 4-(4-Cinnamoylphenyl)butyrate

To a solution of 10.00 g of 4-(4-cinnamoylphenyl)butyric acid in 50 ml of methanol, 0.25 ml of sulfuric acid was added, and the mixture was refluxed for 1 hour. The solvent was removed under reduced pressure, and then the residue was added with water and extracted with ether. The ether layer was washed with water and dried, and then the solvent was removed under reduced pressure. The residue was purified by column chromatography on silica gel (methylene chloride:n-hexane=3:2) to yield 8.94 g of pale yellow crystals. Recrystallization from n-hexane gave pale yellow needles, mp 43°–44° C.

Analysis for $C_{20}H_{20}O_3$

Calculated C, 77.90; H, 6.54 Found C, 78.10; H, 6.65

The compounds of Reference Examples 52 through 58 shown in Table 14 were obtained in the same manner as described in Reference Example 51.

TABLE 13

| Reference Example No. | Compound | Appearance | mp | Analysis (upper:Calculated) (lower:Found |
|---|---|---|---|---|
| 44 | 4-[4-(4-Methyl-cinnamoyl)phenyl]-butyric Acid | pale yellow plates (MeOH) | 148.5–150.5° C. | $C_{20}H_{20}O_3$ C, 77.90; H, 6.54 C, 77.94; H, 6.48 |
| 45 | 4-[4-(4-Butyl-cinnamoyl)phenyl]-butyric Acid | colorless flakes (i-Pr$_2$O) | 108–109° C. | $C_{23}H_{26}O_3$ C, 78.83; H, 7.48 C, 78.70; H, 7.60 |
| 46 | 4-[4-(4-Butoxy-cinnamoyl)phenyl]-butyric Acid | pale yellow needles (MeOH) | 105.5–107.5° C. | $C_{23}H_{26}O_4$ C, 75.38; H, 7.15 C, 75.29; H, 7.22 |
| 47 | 4-[4-(4-Chloro-cinnamoyl)phenyl]-butyric Acid | pale yellow needles (MeOH) | 159–161° C. | $C_{19}H_{17}ClO_3$ C, 69.41; H, 5.21 C, 69.42; H, 4.94 |
| 48 | 4-[4-(4-Fluoro-cinnamoyl)phenyl]-butyric Acid | pale yellow flakes (MeOH) | 126–129.5° C. | $C_{19}H_{17}FO_3$ C, 73.06; H, 5.49 C, 72.98; H, 5.25 |
| 49 | 4-[4-(3-Fluoro-cinnamoyl)phenyl]-butyric Acid | pale yellow plates (AcOEt-i-Pr$_2$O) | 104–106° C. | $C_{19}H_{17}FO_3$ C, 73.06; H, 5.49 C, 72.95; H, 5.33 |
| 50 | 4-[4-(1-Oxo-5-phenyl-pentan-2, 4-dien-1-yl)-phenyl]butyric Acid | pale yellow needles (AcOEt) | 141–143.5° C. | $C_{21}H_{20}O_3$ C, 78.73; H, 6.29 C, 78.54; H, 6.29 |

TABLE 14

| Reference Example No. | Compound | Appearance | mp | Analysis (upper:Calculated) (lower:Found) |
|---|---|---|---|---|
| 52 | Methyl 4-[4-(4-Methyl-cinnamoyl)phenyl]-butyrate | pale yellow flakes (AcOEt) | 102.5~104° C. | $C_{21}H_{22}O_3$<br>C, 78.23; H, 6.88<br>C, 78.27; H, 7.00 |
| 53 | Methyl 4-[4-(4-Butyl-cinnamoyl)phenyl]-butyrate | pale yellow needles (i-Pr$_2$O-n-Hexane) | 57~58° C. | $C_{24}H_{28}O_3$<br>C, 79.09; H, 7.74<br>C, 79.17; H, 8.03 |
| 54 | Methyl 4-[4-(4-Butoxy-cinnamoyl)phenyl]-butyrate | pale yellow needles (i-Pr$_2$O) | 70~71.5° C. | $C_{24}H_{28}O_4$<br>C, 75.76; H, 7.42<br>C, 75.82; H, 7.63 |
| 55 | Methyl 4-[4-(4-Chloro-cinnamoyl)phenyl]-butyrate | pale yellow flakes (AcOEt) | 116~118° C. | $C_{20}H_{19}ClO_3$<br>C, 70.07; H, 5.59<br>C, 70.04; H, 5.57 |
| 56 | Methyl 4-[4-(4-Fluoro-cinnamoyl)phenyl]-butyrate | pale yellow plates (MeOH) | 100.5~101.5° C. | $C_{20}H_{19}FO_3$<br>C, 73.60; H, 5.87<br>C, 73.74; H, 5.91 |
| 57 | Methyl 4-[4-(3-Fluoro-cinnamoyl)phenyl]-butyrate | pale yellow plates (i-Pr$_2$O) | 54~54.5° C. | $C_{20}H_{19}FO_3$<br>C, 73.60; H, 5.87<br>C, 73.65; H, 5.89 |
| 58 | Methyl 4-[4-(1-Oxo-5-phenylpentan-2,4-dien-1-yl)phenyl]butyrate | pale yellow flakes (MeOH) | 81~82.5° C. | $C_{22}H_{22}O_3$<br>C, 79.02; H, 6.63<br>C, 79.02; H, 6.75 |

Reference Example 59

Methyl 4-[4-(3-Phenylpropionyl)phenyl]butyrate

To a solution of 3.89 g of methyl 4-(4-cinnamoylphenyl) butyrate in 50 ml of methanol, 0.25 g of 10% palladium on carbon was added, and hydrogenation was carried out at an ordinary temperature and under ordinary pressure for 5 hours. The catalyst was filtered off and the filtrate was concentrated under reduced pressure to give 3.87 g of pale brown oil.

IR spectrum ν (liq) cm$^{-1}$: 1738, 1684

Mass spectrum m/z: 310 (M$^+$)

NMR spectrum δ (CDCl$_3$) ppm: 1.97(2H,qn,J=7.5 Hz), 2.33(2H,t,J=7.5 Hz), 2.70(2H,t,J=7.5 Hz), 3.06(2H,t,J=8 Hz), 3.28(2H,t,J=8 Hz), 3.67(3H,s), 7.15–7.32(7H,m), 7.89(2H,d,J=8 Hz)

The compounds of Reference Examples 60 and 61 shown in Tables 15 and 16 were obtained in the same manner as described in Reference Example 59.

TABLE 15

| Reference Example No. | Compound | Appearance | mp | Analysis (upper:Calculated) (lower:Found) |
|---|---|---|---|---|
| 60 | Methyl 4-[4-[3-(4-Butoxyphenyl)-propionyl]phenyl]-butyrate | pale yellow needles (MeOH) | 59~60° C. | $C_{24}H_{30}O_4$<br>C, 75.36; H, 7.91<br>C, 75.23; H, 8.13 |

TABLE 16

| Reference Example No. | Compound Appearance | IR ν (liq) cm$^{-1}$ | NMR δ (CDCl$_3$) |
|---|---|---|---|
| 61 | Methyl 4-[4-(5-Phenyl-valeryl)phenyl]butyrate colorless oil | 1738, 1684 | 1.68–1.83(4H, m), 1.97(2H, qn, J=7.5Hz), 2.34(2H, t, J=7.5Hz), 2.67(2H, t, J=7.5Hz), 2.71(2H, t, J=7.5Hz), 2.96(2H, t, J=7.5Hz), 3.67(3H, s), 7.14–7.30(7H, m), 7.87(2H, d, J=8.5Hz) |

Reference Example 62

Methyl 4-(4-Ethoxycarbonylacetylphenyl)butyrate

To a solution of 20.0 g of methyl 4-phenylbutyrate in 100 ml of carbon disulfide, 44.9 g of anhydrous aluminium chloride was added under ice-cooling, and then 16.9 g of ethyl malonyl chloride was added dropwise. After being heated under reflux for 1.5 hours, the reaction mixture was poured into ice-water and then extracted with ether. After the ether layer was washed successively with water, aqueous potassium carbonate solution and water and then dried, the solvent was removed under reduced pressure. The residue was purified by column chromatography on silica gel (methylene chloride) to yield 20.2 g of a pale yellow oil.

IR spectrum ν (liq) cm$^{-1}$: 1738, 1688

Mass spectrum m/z: 292 (M$^+$)

NMR spectrum δ (CDCl$_3$) ppm: 1.26(3H,t,J=7.5 Hz), 1.98(2H,qn,J=7.5 Hz), 2.34(2H,t,J=7.5 Hz), 2.72(2H,t,J=7.5 Hz), 3.67(3H,s), 3.96(2H,s), 4.21(2H,q,J=7.5 Hz), 7.29(2H, d,J=8.5 Hz), 7.87(2H,d,J=8.5 Hz)

Reference Example 63

Methyl 4-[4-[α-Ethoxycarbonyl-α-(2-phenylethyl)]acetylphenyl]butyrate 0.92 g of 60% sodium hydride was added to 10 ml of dry N,N-dimethylformamide under ice-cooling, and then a solution of 6.70 g of methyl 4-(4-ethoxycarbonylacetylphenyl-)butylate in 16 ml of dry N,N-dimethylformamide was added dropwise and stirring was contiuned at room temperature for 10 minutes. To the reaction mixture, a solution of 4.24 g of β-bromoethylbenzene in 13 ml of N,N-dimethylformamide was added dropwise at room temperature, and then stirring was continued at 100° C. under heating for 1 hour. After being cooled, the reaction mixture was poured into dilute hydrochloric acid and then extracted with ether. The ether layer was washed with water and dried, and the solvent was removed under reduced pressure. The residue was purified by column chromatography on silica gel (methylene chloride:n-hexane=3:1→5:1) to yield 3.88 g of colorless oil.

IR spectrum ν (liq) cm$^{-1}$: 1738, 1686

Mass spectrum m/z: 396 (M$^+$)

NMR spectrum δ (CDCl$_3$) ppm: 1.18(3H,t,J=7.5 Hz), 1.97(2H,qn,J=7.5 Hz), 2.26–2.39(2H,m), 2.34(2H,t,J=7.5 Hz), 2.63–2.74(2H,m), 2.70(2H,t,J=7.5 Hz), 3.67(3H,s), 4.16(2H,q,J=7.5 Hz), 4.26(1H,t,J=7.5 Hz), 7.15–7.31(1H, m), 7.81(2H,d,J=8.5 Hz)

The compound of Reference Example 64 was obtained in the same manner as described in Reference Example 63.

Reference Example 64

Ethyl 6-Phenyl-2-[4-(3-methoxycarbonylpropyl)benzoyl]hexanoate

Appearance colorless viscous oil

IR spectrum ν (liq) cm$^{-1}$: 1738, 1686

Mass spectrum m/z: 424 (M$^+$)

NMR spectrum δ (CDCl$_3$) ppm: 1.16(3H,t,J=7.5 Hz), 1.40(2H,qn,J=7.5 Hz), 1.62–1.70(2H,m), 1.94–2.07(4H,m), 2.34(2H,t,J=7.5 Hz), 2.60(2H,t,J=7.5 Hz), 2.72(2H,t,J=7.5 Hz), 3.67(3H,s), 4.13(2H,qd,J=7.5,2 Hz), 4.24(2H,t,J=7 Hz), 7.13–7.19(4H,m), 7.24–7.29(3H,m), 7.90(2H,d,J=8 Hz)

Reference Example 65

4-[4-(4-Phenylbutyryl)phenyl]butyric Acid

A mixture of 1.90 g of methyl 4-[4-(α-ethoxycarbonyl-α-(2-phenylethyl)]acetylphenyl butyrate, 29 ml of sulfuric acid, 9.5 ml of acetic acid and 5.7 ml of water was refluxed for 17 hours. After being cooled, the reaction mixture was added with water and extracted with methylene chloride. The methylene chloride layer was washed with water and dried, and the solvent was removed under reduced pressure. The residue was purified by column chromatography on silica gel (methylene chloride:ethyl acetate=2:1) to yield 0.82 g of colorless crystals. Recrystallization from ethyl acetate gave colorless flakes, mp 111°~111.5° C.

Analysis for C$_{20}$H$_{22}$O$_3$

Calculated C, 77.39; H, 7.14 Found C, 77.53 ; H, 7.31

The compound of Reference Example 66 was obtained in the same manner as described in Reference Example 65.

Reference Example 66

4-[4-(6-Phenylhexanoyl)phenyl]butyric Acid

Appearance colorless needles (AcOEt)

mp 86°~89° C.

Analysis for C$_{22}$H$_{26}$O$_3$

Calculated C, 78.07; H, 7.74 Found C, 78.07; H, 7.99

Reference Example 67

Methyl 4-[4-(4-phenylbutyryl)phenyl]butyrate

To a suspension of 2.10 g of 4-[4-(4-phenylbutyryl)phenyl]butyric acid in 15 ml of methanol, 0.1 ml of sulfuric acid was added, and the mixture was heated under reflux for 4 hours. After the reaction solution was removed under reduced pressure, the residue was dissolved in ethyl acetate and then washed successively with water, aqueous potassium carbonate and water. After the ethyl acetate layer was dried, the solvent was removed under reduced pressure. The residue was washed with isopropyl ether to yield 1.87 g of colorless crystals. Recrystallization from methanol gave colorless flakes, mp 61°–62° C.

Analysis for C$_{21}$H$_{24}$O$_3$

Calculated C, 77.75; H, 7.46 Found C, 77.62; H, 7.32

The compound of Reference Example 68 was obtained in the same manner as described in Reference Example 67.

Reference Example 68

Methyl 4-[4-(6-Phenylhexanoyl)phenyl]butyrate

Appearance colorless flakes (MeOH)

mp 45.5°~46.5° C.

Analysis for C$_{23}$H$_{28}$O$_3$

Calculated C, 78.38; H, 8.01 Found C, 78.24; H, 7.92

Reference Example 69

Methyl 4-[4-(1-Hydroxy-2-phenylethyl)phenyl]butyrate

To a suspension of 20.0 g of methyl 4-[4-(phenylacetyl)phenyl]butyrate in 200 ml of methanol, 2.52 g of sodium borohydride was added portionwise under ice-cooling, and stirring was continued for 1 hour. After the reaction solvent was removed under reduced pressure, the residue was added with water and then extracted with ether. After the ether layer was washed with water and dried, the solvent was removed to yield 20.3 g of pale yellow oil.

IR spectrum ν (liq) cm$^{-1}$: 3464, 1738

Mass spectrum m/z: 298 (M$^+$)

NMR spectrum δ (CDCl₃) ppm: 1.95(2H,qn,J=7.5 Hz), 2.33(2H,t,J=7.5 Hz), 2.65(2H,t,J=7.5 Hz), 2.98(1H,dd,J=14, 8.5 Hz), 3.03(1H,dd,J=14,5 Hz), 3.67(3H,s), 4.87(1H,dd,J=8.5,5 Hz), 7.15–7.30(9H,m)

The compounds of Reference Examples 70 through 115 shown in Tables 17 to 26 were obtained in the same manner as described in Reference Example 69.

TABLE 17

| Reference Example No. | Compound | Appearance | mp | Analysis (upper: Calculated) (lower: Found) |
|---|---|---|---|---|
| 70 | Methyl 3-[4-(1-Hydroxy-2-phenylethyl)phenyl]-propionate | colorless flakes (i-Pr₂O) | 38~39.5° C. | C₁₈H₂₀O₃ C, 76.03; H, 7.09 C, 76.05; H, 7.38 |
| 71 | Methyl 4-[4-[2-(4-Chlorophenyl)-1-hydroxyethyl]phenyl]-butyrate | colorless needles (i-Pr₂O-n-Hexane) | 45~46.5° C. | C₁₉H₂₁ClO₃ C, 68.57; H, 6.36 C, 68.73; H, 6.63 |
| 72 | Methyl 5-[4-(1-Hydroxy-2-phenylethyl)phenyl]-valerate | colorless columns (i-Pr₂O) | 46.5~47.5° C. | C₂₀H₂₄O₃ C, 76.89; H, 7.74 C, 77.04; H, 8.01 |

TABLE 18

| Reference Example No. | Compound Appearance | IR ν (liq) cm⁻¹ | NMR δ (CDCl₃) |
|---|---|---|---|
| 73 | Methyl 4-(4-[2-(2-Fluorophenyl)-1-hydroxyethyl]-phenyl]butyrate pale brown oil | 3464, 1738 | 1.91(1H, d, J=3Hz), 1.95(2H, qn, J=7.5Hz, 2.32(2H, t, J=7.5Hz), 2.65(2H, t, J=7.5Hz), 3.01(1H, dd, J=13.5, 8.5Hz), 3.09(1H, dd, J=13.5, 5Hz), 3.67 (3H, s), 4.93(1H, m), 7.01–7.08(2H, m), 7.15(2H, d, J=8.5Hz), 7.16–7.24(2H, m), 7.29(2H, d, J=8.5Hz) |
| 74 | Methyl 4-[4-[2-(3-Fluorophenyl)-1-hydroxyethyl]-phenyl]butyrate pale brown oil | 3464, 1738 | 1.90(1H, d, J=3Hz), 1.95(2H, qn, J=7.5Hz), 2.33(2H, t, J=7.5Hz), 2.65(2H, t, J=7.5Hz), 3.00(2H, d, J=6.5Hz), 3.67 (3H, s), 4.87(1H, td, J=6.5, 3Hz), 6.88–6.95(2H, m), 6.96(1H, d, J=7.5Hz), 7.16(2H, d, J=8Hz), 7.22–7.28(1H, m), 7.26(2H, d, J=8Hz) |

TABLE 19

| Reference Example No. | Compound Appearance | IR ν (liq) cm⁻¹ | NMR δ (CDCl₃) |
|---|---|---|---|
| 75 | Methyl 4-[4-[2-(4-Fluorophenyl)-1-hydroxyethyl]-phenyl]butyrate pale brown oil | 3464, 1738 | 1.79(1H, brs), 1.95(2H, qn, J=7.5Hz), 2.32(2H, t, J=7.5Hz), 2.65(2H, t, J=7.5Hz), 2.98(2H, d, J=6.5Hz), 3.67(3H, s), 4.83(1H, t, J=6.5Hz), 6.96(2H, t, J=8.5Hz), 7.12(2H, dd, J=8.5, 5.5Hz), 7.15(2H, d, J=8Hz), 7.24(2H, d, J=8Hz) |
| 76 | Methyl 4-[4-[1-Hydroxy-2-(p-tolyl)ethyl]phenyl]-butyrate pale yellow oil | 3464, 1738 | 1.95(2H, qn, J=7.5Hz), 2.32(3H, s), 2.33 (2H, t, J=7.5Hz), 2.65(2H, t, J=7.5Hz), 2.92(1H, dd, J=14, 8.5Hz), 3.00 (1H, dd, J=14, 5Hz), 3.67(3H, s), 4.84 (1H, dd, J=8.5, 5Hz), 7.09(2H, d, J=8.5Hz), 7.11(2H, d, J=8.5Hz), 7.16(2H, d, J=8Hz), 7.24(2H, d, J=8Hz) |
| 77 | Methyl 4-[4-(1-Hydroxyethyl)phenyl]butyrate pale yellow oil | 3432, 1738 | 1.49(3H, d, J=6.5Hz), 1.69(1H, brs), 1.95(2H, qn, J=7.5Hz), 2.33(2H, t, J=7.5Hz), 2.64(2H, t, J=7.5Hz), 3.67(3H, s), 4.88(1H, q, J=6.5Hz), 7.16(2H, d, J=8.5Hz), 7.30(2H, d, J=8.5Hz) |
| 78 | Methyl 4-[4-(1-Hydroxypropyl)phenyl]butyrate pale yellow oil | 3460, 1738 | 0.92(3H, t, J=7.5Hz), 1.67–1.85(3H, m), 1.95(2H, qn, J=7.5Hz), 2.33(2H, t, J=7.5Hz), 2.64(2H, t, J=7.5Hz), 3.66 (3H, s), 4.57(1H, t, J=7Hz), 7.16(2H, d, J=8Hz), 7.26(2H, d, J=8Hz) |
| 79 | Methyl 4-(4-(1-Hydroxybutyl)phenyl]butyrate | 3432, 1738 | 0.93(3H, t, J=7.5Hz), 1.26–1.36(1H, m), 1.38–1.48(1H, m), 1.63–1.71(1H, |

TABLE 19-continued

| Reference Example No. | Compound Appearance | IR ν (liq) cm⁻¹ | NMR δ (CDCl₃) |
|---|---|---|---|
| | colorless oil | | m), 1.74–1.83(2H, m), 1.95(2H, qn, J= 7.5Hz), 2.33(2H, t, J=7.5Hz), 2.64(2H, t, J=7.5Hz), 3.67(3H, s), 4.63–4.67 (1H, m), 7.15(2H, d, J=8.5Hz), 7.26 (2H, d, J=8.5Hz) |
| 80 | Methyl 4-[4-(1-Hydroxy-pentyl)phenyl]butyrate colorless oil | 3432, 1738 | 0.89(3H, t, J=7Hz), 1.20–1.45(2H, m), 1.34(2H, qn, J=7Hz), 1.65–1.75(1H, m), 1.76–1.85(1H, m), 1.77(1H, d, J=3Hz), 1.95(2H, qn, J=7.5Hz), 2.33(2H, t, J=7.5Hz), 2.64(2H, t, J=7.5Hz), 3.67 (3H, s), 4.61–4.66(1H, m), 7.16(2H, d, J=8Hz), 7.26(2H, d, J=8Hz) |

| Reference Example No. | Compound Appearance | IR ν (liq) cm⁻¹ | NMR δ (CDCl₃) |
|---|---|---|---|
| 81 | Methyl 4-[4-(1-Hydroxy-hexyl)phenyl]butyrate colorless oil | 3432, 1738 | 0.87(3H, t, J=7Hz), 1.20–1.37(5H, m), 1.36–1.45(1H, m), 1.66–1.74(1H, m), 1.75–1.84(1H, m), 1.75(1H, d, J=3.5Hz), 1.95(2H, qn, J=7.5Hz), 2.33(2H, t, J=7.5Hz), 2.64(2H, t, J=7.5Hz), 3.67 (3H, s), 4.60–4.67(1H, m), 7.16(2H, d, J=8Hz), 7.26(2H, d, J=8Hz) |
| 82 | Methyl 4-[4-(1-Hydroxy-decyl)phenyl]butyrate pale yellow oil | 3424, 1742 | 0.87(3H, t, J=7Hz), 1.20–1.36(13H, m), 1.38–1.42(1H, m), 1.66–1.72(1H, m), ), 1.75(1H, d, J=4Hz), 1.76–1.82(1H, m), 1.95(2H, qn, J=7.5Hz), 2.33(2H, t, J=7.5Hz), 2.64(2H, t, J=7.5Hz), 3.67 (3H, s), 4.61–4.65(1H, m), 7.15(2H, d, J=8Hz), 7.26(2H, d, J=8Hz) |
| 83 | Methyl 4-[4-(1-Hydroxy-3-methylbutyl)phenyl]-butyrate colorless oil | 3432, 1738 | 0.94(3H, d, J=6.5Hz), 0.95(3H, d, J=6.5Hz), 1.47–1.53(1H, m), 1.66–1.76 (2H, m), 1.71(1H, d, J=3Hz), 1.95(2H, qn, J=7.5Hz), 2.33(2H, t, J=7.5Hz), 2.64 (2H, t, J=7.5Hz), 3.67(3H, s), 4.70– 4.73(1H, m), 7.16(2H, d, J=8Hz), 7.27 (2H, d, J=8Hz) |
| 84 | Methyl 4-[4-(1-Hydroxy-4-methylpentyl)phenyl]-butyrate colorless oil | 3432, 1738 | 0.87(3H, d, J=6.5Hz), 0.88(3H, d, J=6.5Hz), 1.10–1.17(1H, m), 1.29–1.36 (1H, m), 1.50–1.60(1H, m), 1.66–1.74 (1H, m), 1.76(1H, d, J=3Hz), 1.77–1.83 (1H, m), 1.95(2H, qn, J=7.5Hz), 2.33 (2H, t, J=7.5Hz), 2.64(2H, t, J=7.5Hz), 3.67(3H, s), 4.59–4.62(1H, m), 7.16 (2H, d, J=8Hz), 7.26(2H, d, J=8Hz) |
| 85 | Methyl 4-[4-(3, 3-Dimethyl-1-hydroxybutyl)phenyl]-butyrate colorless oil | 3464, 1738 | 0.99(9H, s), 1.56(1H, s), 1.62(1H, dd, J=14, 4Hz), 1.75(1H, dd, J=14, 8.5Hz), 1.95(2H, qn, J=7.5Hz), 2.32(2H, t, J=7.5Hz), 2.64(2H, t, J=7.5Hz), 3.67 (3H, s), 4.80(1H, dt, J=8.5, 4Hz), 7.15 (2H, d, J=8Hz), 7.26(2H, d, J=8Hz) |

TABLE 21

| Reference Example No. | Compound Appearance | IR ν (liq) cm⁻¹ | NMR δ (CDCl₃) |
|---|---|---|---|
| 86 | Methyl 4-[4-(Cyclopentyl-hydroxymethyl)phenyl]-butyrate pale yellow oil | 3464, 1738 | 1.12–1.16(1H, m), 1.36–1.66(6H, m), 1.87–1.91(1H, m), 1.70(1H, s), 1.95 (2H, qn, J=7.5Hz), 2.21(2H, sex, J=8.5Hz), 2.33(2H, t, J=7.5Hz), 2.64(2H, t, J=7.5Hz), 3.67(3H, s), 4.37(1H, d, J= 8.5Hz), 7.14(2H, d, J=8Hz), 7.26(2H, |

TABLE 21-continued

| Reference Example No. | Compound Appearance | IR ν (liq) cm⁻¹ | NMR δ (CDCl₃) |
|---|---|---|---|
| 87 | Methyl 4-[4-(Cyclohexyl-hydroxymethyl)phenyl]-butyrate<br>colorless oil | 3516, 1738 | 0.86–0.96(1H, m), 0.99–1.30(4H, m), 1.33–1.40(1H, m), 1.54–1.80(5H, m), 1.90–2.02(1H, m), 1.95(2H, qn, J=7.5Hz), 2.33(2H, t, J=7.5Hz), 2.64(2H, t, J=7.5Hz), 3.67(3H, s), 4.33(1H, d, J=7.5Hz), 7.14(2H, d, J=8Hz), 7.21(2H, d, J=8Hz) |
| 88 | Methyl 4-[4-(Cycloheptyl-hydroxymethyl)phenyl]-butyrate<br>pale brown oil | 3464, 1740 | 1.10–1.19(1H, m), 1.29–1.93(13H, m), 1.95(2H, qn, J=7.5Hz), 2.33(2H, t, J=7.5Hz), 2.64(2H, t, J=7.5Hz), 3.66(3H, s), 4.43(1H, d, J=6.5Hz), 7.14(2H, d, J=8Hz), 7.23(2H, d, J=8Hz) |
| 89 | Methyl 4-[4-(2-Cyclopentyl-1-hydroxyethyl)phenyl]-butyrate<br>colorless oil | 3440, 1742 | 1.08–1.20(2H, m), 1.46–1.54(2H, m), 1.56–1.64(2H, m), 1.66–1.72(1H, m), 1.74(1H, s), 1.77–1.88(4H, m), 1.95(2H, qn, J=7.5Hz), 2.33(2H, t, J=7.5Hz), )2.64(2H, t, J=7.5Hz), 3.66(3H, s), 4.67(1H, t, J=7Hz), 7.15(2H, d, J=8Hz), 7.27(2H, d, J=8Hz) |
| 90 | Methyl 4-[4-(2-Cyclohexyl-1-hydroxyethyl)phenyl]-butyrate<br>colorless oil | 3448, 1742 | 0.88–1.02(2H, m), 1.11–1.29(3H, m), 1.37–1.46(1H, m), 1.48–1.54(1H, m), 1.62–1.84(6H, m), 1.68(1H, s), 1.95(2H, qn, J=7.5Hz), 2.33(2H, t, J=7.5Hz), 2.64(2H, t, J=7.5Hz), 3.66(3H, s), 4.76(1H, dd, J=9, 5Hz), 7.15(2H, d, J=8Hz), 7.26(2H, d, J=8Hz) |
| 91 | Methyl 4-[4-(3-Cyclohexyl-1-hydroxypropyl)phenyl]-butyrate<br>pale brown oil | 3460, 1740 | 0.80–0.90(2H, m), 1.08–1.27(5H, m), 1.27–1.37(1H, m), 1.58–1.84(7H, m), 1.79(1H, d, J=3.5Hz), 1.95(2H, qn, J=7.5Hz), 2.33(2H, t, J=7.5Hz), 2.64(2H, t, J=7.5-Hz), 3.66(3H, s), 4.57–4.63(1H, m), 7.15(2H, d, J=8Hz), 7.25(2H, d, J=8Hz) |

TABLE 22

| Reference Example No. | Compound Appearance | IR ν (liq) cm⁻¹ | NMR (CDCl₃) |
|---|---|---|---|
| 92 | Methyl 4-[4-(4-Cyclohexyl-1-hydroxybutyl)phenyl]-butyrate<br>pale yellow oil | 3432, 1740 | 0.80–0.90(2H, m), 1.08–1.33(7H, m), 1.38–1.48(1H, m), 1.60–1.70(6H, m), 1.73–1.81(1H, m), 1.77(1H, s), 1.95(2H, qn, J=7.5Hz), 2.33(2H, t, J=7.5Hz), 2.64(2H, t, J=7.5Hz), 3.67(3H, s), 4.63(1H, t, J=6Hz), 7.15(2H, d, J=8Hz), 7.26(2H, d, J=8Hz) 87(2H, m), 1.08–1.43(10H, m) |
| 93 | Methyl 4-[4-(5-Cyclohexyl-1-hydroxypentyl)phenyl]-butyrate<br>pale yellow oil | 3444, 1742 | 0.80–0.87(2H, m), 1.08–1.43(10H,m), 1.60–1.72(6H, m), 1.75–1.82(1H, m), 1.82(1H, s), 1.95(2H, qn, J=7.5Hz), 2.33(2H, t, J=7.5Hz), 2.64(2H, t, J=7.5Hz), 3.66(3H, s), 4.62(1H, m), 7.15(2H, d, J=8Hz), 7.25(2H, d, J=8Hz) |
| 94 | Methyl 4-[4-(6-Cyclohexyl-1-hydroxyhexyl)phenyl]-butyrate<br>colorless oil | 3460, 1738 | 0.78–0.90(2H, m), 1.08–1.46(12H, m), 1.60–1.85(7H, m), 1.76(1H, d, J=3Hz), 1.95(2H, qn, J=7.5Hz), 2.33(2H, t, J=7.5Hz), 2.64(2H, t, J=7.5Hz), 3.66(3H, s), 4.60–4.65(1H, m), 7.16(2H, d, J=8Hz), 7.26(2H, d, J=8Hz) |
| 95 | Methyl trans-4-[4-(Hydroxy(4-methylcyclo-hexyl)methyl]phenyl]-butyrate<br>colorless oil | 3464, 1738 | 0.78–1.12(4H, m), 0.85(3H, d, J=6Hz), 1.21–1.39(1H, m), 1.50–1.66(2H, m), 1.70–1.76(1H, m), 1.78(1H, d, J=3Hz), 1.95(2H, qn, J=7.5Hz), 1.98–2.04(1H, m), 2.33(2H, t, J=7.5Hz), 2.64(2H, t, J=7.5Hz), 3.67(3H, s), 4.32(1H, dd, J=7.5, 3Hz), 7.14(2H, d, J=8.5Hz), 7.21(2H, d, J=8.5Hz) |
| 96 | Methyl trans-4-[4- | (KBr) | 0.78–1.32(13H, m), 0.87(3H, t, J=7Hz), |

TABLE 22-continued

| Reference Example No. | Compound Appearance | IR ν (liq) cm$^{-1}$ | NMR (CDCl$_3$) |
|---|---|---|---|
| | [Hydroxy(4-pentylcyclohexyl)methyl]phenyl]butyrate colorless amorphous solid | 3436, 1738 | 1.36–1.40(1H, m), 1.52–1.60(1H, m), 1.65–1.71(1H, m), 1.76–1.82(2H, m), 1.95(2H, qn, J=7.5Hz), 1.98–2.05 (1H, m), 2.33(2H, t, J=7.5Hz), 2.64(2H, t, J=7.5Hz), 3.67(3H, s), 4.32(1H, dd, J=7, 2.5Hz), 7.14(2H, d, J=8Hz), 7.21 21(2H, d, J=8Hz) |
| 97 | Methyl 4-[4-[2-(1-Adamantyl)-1-hydroxyethyl]phenyl]butyrate colorless oil | 3448, 1740 | 1.58–1.72(14H, m), 1.92–1.98(5H, m), 2.33(2H, t, J=7.5Hz), 2.64(2H, t, J=7.5Hz), 3.67(3H, s), 4.87(1H, in), 7.14 4(2H, d, J=8Hz), 7.25(2H, d, J=8Hz) |

| Reference Example No. | Compound Appearance | IR ν (liq) cm$^{-1}$ | NMR (CDCl$_3$) |
|---|---|---|---|
| 98 | Methyl 4-[4-1-Hydroxy-2-(2-norbornyl)ethyl]phenyl]butyrate pale yellow oil | 3432, 1738 | 1.05–1.16(4H, m), 1.30–1.32(1H, m), 1.40–1.52(4H, m), 1.62–1.70(3H, m), 1.92–1.98(3H, m), 2.19(1H, s), 2.32 (2H, t, J=7.5Hz), 2.64(2H, t, J=7.5Hz), 3.69(3H, s), 4.64(1H, m), 7.16(2H, d, J=8Hz), 7.25(2H, d, J=8Hz) |
| 99 | Methyl 4-[4-(1-Hydroxy-3-phenylpropyl)phenyl]butyrate colorless oil | 3436, 1738 | 1.71(1H, brs), 1.95(2H, qn, J=7.5Hz), 1.98–2.06(1H, m), 2.09–2.17(1H, m), 2.33(2H, t, J=7.5Hz), 2.64(2H, t, J=7.5Hz), 2.64–2.70(1H, m), 2.75(1H, ddd, J=14, 9.5, 6Hz), 3.66(3H, s), 4.66 (1H, dd, J=8.5, 5Hz), 7.17–7.21(5H, m), 7.25–7.30(4H, m) |
| 100 | Methyl 5-[4-(1-Hydroxypentyl)phenyl]valerate colorless oil | 3464, 1740 | 0.89(3H, t, J=7Hz), 1.19–1.45(4H, m), 1.54–1.84(6H, m), 1.76(1H, d, J=3.5Hz), 2.33(2H, t, J=7Hz), 2.62(2H, t, J=7.5Hz), 3.66(3H, s), 4.60–4.66(1H, m), 7.15(2H, d, J=8.5Hz), 7.25(2H, d, J=8.5Hz) |
| 101 | Methyl 5-[4-(1-Hydroxyhexyl)phenyl]valerate colorless oil | 3464, 1740 | 0.84–0.89(3H, m), 1.20–1.37(5H, m), 1.37–1.48(1H, m), 1.60–1.83(6H, m), 1.76(1H, d, J=3.5Hz), 2.33(2H, t, J=7Hz), 2.62(2H, t, J=7Hz), 3.66(3H, s), 4.60–4.66(1H, m), 7.15(2H, d, J=8.5Hz), 7.25(2H, d, J=8.5Hz) |
| 102 | Methyl 5-[4-(2-Cyclohexyl-1-hydroxyethyl)phenyl]valerate pale brown oil | 3456, 1738 | 0.88–1.02(2H, m), 1.10–1.29(3H, m), 1.36–1.46(1H, m), 1.47–1.54(1H, m), 1.58–1.84(10H, m), 1.72(1H, d, J=3Hz), 2.33(2H, t, J=7Hz), 2.62(2H, t, J=7.5Hz), 3.66(3H, s), 4.75–4.79(1H, brs), 7.14(2H, d, J=8Hz), 7.25(2H, d, J=8Hz) |
| 103 | Methyl 4-[4-(1-Hydroxyheptyl)phenyl]butyrate colorless oil | 3444, 1740 | 0.87(3H, t, J=7.5Hz), 1.19–1.34(7H, m), 1.37–1.45(1H, m), 1.60–1.72(1H, m), 1.75–1.83(1H, m), 1.77(1H, d, J=3.5Hz), 1.95(2H, qn, J=7.5Hz), 2.33(2H, t, J=7.5Hz), 2.64(2H, t, J=7.5Hz), 3.67(3H, s), 4.63(1H, t, J=6.5Hz)7.15 5(2H, d, J=8Hz), 7.26(2H, d, J=8Hz) |

| Reference Example No. | Compound Appearance | IR ν (liq) cm$^{-1}$ | NMR δ (CDCl$_3$) |
|---|---|---|---|
| 104 | Methyl 4-[4-(1-Hydroxyoctyl)phenyl]butyrate colorless oil | 3542. 1742 | 0.87(3H, t, J=7Hz), 1.19–1.32(9H, m), 1.36–1.44(1H, m), 1.64–1.72(1H, m), 1.75–1.82(1H, m), 1.78(1H, d, J=3Hz), 1.95(2H, t, J=7.5Hz), 2.33(2H, t, J=7.5Hz), 2.64(2H, t, J=7.5Hz), 3.67 |

-continued

| Reference Example No. | Compound Appearance | IR ν (liq) cm⁻¹ | NMR δ (CDCl₃) |
|---|---|---|---|
| | | | (3H, s), 4.63(1H, t, J=6Hz)7.16(2H, d, J=8Hz), 7.26(2H, d, J=8Hz) |
| 105 | 4-[4-(1-Hydroxy-phenyl]butyrate pale brown oil | 3440, 1742 | 0.87(3H, t, J=7Hz), 1.19–1.33(11H, m), 1.36–1.44(1H, m), 1.65–1.72(1H, m), 1.75–1.82(1H, m), 1.78(1H, s), 1.95(2H, qn, J=7.5Hz), 2.33(2H, t, J=7.5Hz), 2.64(2H, t, J=7.5Hz), 3.66(3H, s), 4.63(1H, t, J=6.5Hz)7.15(2H, d, J=8Hz), 7.26(2H, d, J=8Hz) |
| 106 | Methyl 4-[4-(1-Hydroxy-5-methylhexyl)phenyl]-butyrate pale yellow oil | 3448, 1740 | 0.85(3H, d, J=7Hz), 0.85(3H, d, J=7Hz), 1.17–1.21(2H, m), 1.21–1.32(1H, m), 1.38–1.47(1H, m), 1.48–1.58(1H, m), 1.63–1.71(1H, m), 1.74–1.82(1H, m), 1.76(1H, d, J=3Hz), 1.95(2H, qn, J=7.5Hz), 2.33(2H, t, J=7.5Hz), 2.64(2H, t, J=7.5Hz), 3.67(3H, s), 4.64(1H, t, J=6.5Hz), 7.16(2H, d, J=8Hz), 7.26(2H, d, J=8Hz) |
| 107 | Methyl 4-[4-(1-Hydroxy-6-methylheptyl)phenyl]-butyrate colorless oil | 3448, 1738 | 0.85(6H, d, J=6.5Hz), 1.12–1.19(2H, m), 1.19–1.44(4H, m), 1.44–1.55(1H, m), 1.65–1.74(1H, m), 1.76(1H, d, J=3.5Hz), 1.75–1.84(1H, m), 1.95(2H, qn J=7.5Hz), 2.33(2H, t, J=7.5Hz), 2.64(2H, t, J=7.5Hz), 3.67(3H, s), 4.61–4.66(1H, m), 7.16(2H, d, J=8Hz), 7.26(2H, d, J=8Hz) |
| 108 | Methyl 4-[4-(4,4-Dimethyl-1-hydroxypentyl)phenyl]-butyrate colorless oil | 3456, 1738 | 0.86(9H, s), 1.09(1H, td, J=13, 4.5Hz), 1.37(1H, td, J=13, 4.5Hz), 1.63–1.81(2H, m), 1.80(1H, brs), 1.95(2H, qn, J=7.5Hz), 2.33(2H, t, J=7.5Hz), 2.64(2H, t, J=7.5Hz), 3.67(3H, s), 4.57(1H, t, J=7Hz), 7.16(2H, d, J=8Hz), 7.26(2H, d, J=8Hz) |

| Reference Example No. | Compound Appearance | IR ν (liq cm⁻¹) | NMR δ (CDCl₃) |
|---|---|---|---|
| 109 | Methyl 4-[4-(5,5-Dimethyl-1-hydroxyhexyl)phenyl] butyrate colorless oil | 3452, 1740 | 0.85(9H, s), 1.17–1.31(3H, m), 1.36–1.46(1H, m), 1.59–1.69(1H, m), 1.72–1.82(1H, m), 1.77(1H, d, J=3.5Hz), 1.95(2H, qn, J=7.5Hz), 2.33(2H, t, J=7.5Hz), 2.64(2H, t, J=7.5Hz), 3.66(3H, s), 4.63–4.67(1H, m), 7.16(2H, d, J=8Hz), 7.26(2H, d, J=8Hz) |
| 110 | Methyl 4-[4-(6,6-Dimethyl-1-hydroxyheptyl)phenyl]-butyrate colorless oil | 3464, 1742 | 0.84(9H, s), 1.12–1.17(2H, m), 1.20–1.30(3H, m), 1.34–1.43(1H, m), 1.65–1.74(1H, m), 1.76–1.84(1H, m), 1.72(1H, brs), 1.95(2H, qn, J=7.5Hz), 2.33(2H, t, J=7.5Hz), 2.64(2H, t, J=7.5Hz), 3.67(3H, s), 4.63(1H, t, J=5.5Hz)7.16(2H, d, J=8Hz), 7.26(2H, d, J=8Hz) |
| 111 | Methyl 4-8 4-(3-Cyclopentyl-1-hydroxyphenyl)phenyl]-butyrate pale yellow oil | 3448, 1740 | 1.00–1.10(2H, m), 1.20–1.30(1H, m), 1.40–1.60(5H, m), 1.65–1.85(6H, m), 1.95(2H, qn, J=7.5Hz), 2.33(2H, t, J=7.5Hz), 2.64(2H, t, J=7.5Hz), 3.67(3H, s), 4.60–4.65(1H, m), 7.16(2H, d, J=8Hz), 7.26(2H, d, J=8Hz) |
| 112 | Methyl 4-[4-[3-(4-Butoxy phenyl)-1-hydroxypropyl]-phenyl]butyrate pale yellow oil | 3464, 1738 | 0.97(3H, t, J=7.5Hz), 1.48(2H, sex, J=7.5Hz), 1.72–1.78(2H, m), 1.80(1H, d, J=3.5Hz), 1.95(2H, qn, J=7.5Hz), 1.19–2.02(1H, m), 2.04–2.13(1H, m), 2.33(2H, t, J=7.5Hz), 2.56–2.71(2H, m), 2.64(2H, t, J=7.5Hz), 3.66(3H, s), 3.93(2H, t, J=7Hz), 4.62–4.66(1H, m), 6.81(2H, d, J=8.5Hz), 7.09(2H, d, J=8.5Hz), 7.16(2H, d, J=8Hz), 7.25(2H, d, J=8Hz) |
| 113 | Methyl 4-[4-(1-Hydroxy-4-phenylbutyl)phenyl]-butyrate | 3460, 1738 | 1.58–1.66(1H, m), 1.68–1.88(4H, m), 1.94(2H, qn, J=7.5Hz), 2.32(2H, t, J=7.5Hz), 2.60–2.65(4H, m), 3.66(3H, s), |

| Reference Example No. | Compound Appearance | IR ν (liq cm⁻¹) | NMR δ (CDCl₃) |
|---|---|---|---|
| | colorless oil | | 4.63–4.67(1H, m), 7.12–7.18(5H, m), 7.22–7.27(4H, m) |

| Reference Example No. | Compound Appearance | IR ν (liq) cm⁻¹ | NMR δ (CDCl₃) |
|---|---|---|---|
| 114 | Methyl 4-[4-(1-Hydroxy-5-phenylpentyl)phenyl]-butyrate colorless oil | 3448, 1738 | 1.28–1.38(1H, m), 1.43–1.53(1H, m), 1.60–1.87(5H, m), 1.95(2H, qn, J=7.5Hz), 2.33(2H, t, J=7.5Hz), 2.59(2H, t, J=7.5Hz), 2.64(2H, t, J=7.5Hz), 3.66 (3H, s), 4.59–4.65(1H, m), 7.12–7.18 (5H, m), 7.22–7.28(4H, m) |
| 115 | Methyl 4-[4-(1-Hydroxy-6-phenylhexyl)phenyl]-butyrate colorless oil | 3432, 1738 | 1.18–1.50(4H, m), 1.55–1.83(5H, m), 1.95(2H, qn, J=7.5Hz), 2.33(2H, t, J=7.5Hz), 2.58(2H, t, J=7.5Hz), 2.64(2H, t, J=7.5Hz), 3.66(3H, s), 4.58–4.69 (1H, m), 7.12–7.19(5H, m), 7.22–7.28(4H, m) |

Reference Example 116

Methyl 4-[4-[3-(4-Butylphenyl)-1-hydroxypropyl] phenyl]butyrate

To a solution of 4.40 g of methyl 4-[4-(4-butylcinnamoyl)phenyl]butyrate in 44 ml of methanol, 0.24 g of 10% palladium on carbon was added, and hydrogenation was carried out at an ordinary temperature and under ordinary pressure for 3.5 hours. After the catalyst was removed by filtration, 0.27 g of sodium borohydride was added to the filtrate under ice-cooling, and then stirring was continued at room temperature for 2 hours. After the reaction solvent was removed under reduced pressure, the residue was added with water and extracted with ether. The ether layer was washed with water, dried, and then the solvent was removed under reduced pressure to yield 4.34 g of colorless oil.

IR spectrum ν (liq) cm⁻¹: 3432, 1740

Mass spectrum m/z: 368 (M⁺)

NMR spectrum δ (CDCl₃) ppm: 0.92(3H,t,J=7.5 Hz), 1.34(2H,sex,J=7.5 Hz), 1.54–1.62(2H,m), 1.80(1H,brs), 1.95(2H,qn,J=7.5 Hz), 1.97–2.05(1H,m), 2.07–2.15(1H,m), 2.33(2H,t,J=7.5 Hz), 2.57(2H,t,J=7.5 Hz), 2.58–2.75(2H, m), 2.64(2H,t,J=7.5 Hz), 3.66(3H,s), 4.66(1H,brt,J=6.5 Hz), 7.05–7.12(4H,m), 7.16(2H,d,J=8 Hz), 7.27(2H,d,J=8 Hz)

Reference Example 117

Methyl 4-[4-[3-(4-Fluorophenyl)-1-hydroxypropyl] phenyl]butyrate

To a solution of 2.72 g of methyl 4-[4-(4-fluorocinnamoyl)phenyl]butyrate in 28 ml of methanol, 140 mg of 5% palladium on carbon was added, and hydrogenation was carried out at an ordinary temperature and under ordinary pressure for 4 hours. The catalyst was filtered off and then the filtrate was concentrated under reduced pressure. The residue was purified by column chromatography on silica gel (methylene chloride→ethyl acetate) to yield 1.69 g of colorless oil.

IR spectrum ν (liq) cm⁻¹: 3452, 1738

Mass spectrum m/z: 330 (M⁺)

NMR spectrum δ (CDCl₃) ppm: 1.83(1H,brs), 1.91–2.14.(2H,m), 1.95(2H,qn,J=7.5 Hz), 2.33(2H,t,J=7.5 Hz), 2.60–2.75(2H,m), 2.64(2H,t,J=7.5 Hz), 3.66(3H,s), 4.63–4.65(1H,m), 6.95(2H,t,J=8.5 Hz), 7.13(2H,dd,J=8.5, 5.5 Hz), 7.16(2H,d,J=8 Hz), 7.26(2H,d,J=8 Hz)

The compounds of Reference Examples 118 through 120 were obtained in the same manner as described in Reference Examples 116 and 117.

Reference Example 118

Methyl 4-[4-[1-Hydroxy-3-(p-tolyl)propyl]phenyl]butyrate

Appearance colorless oil

IR spectrum ν (liq) cm⁻¹: 3440, 1738

Mass spectrum m/z: 326 (M⁺)

NMR spectrum δ (CDCl₃) ppm: 1.79(1H,brs), 1.95(2H, qn,J=7.5 Hz), 1.94–2.04(1H,m), 2.06–2.16(1H,m), 2.31(3H, s), 2.33(2H,t,J=7.5 Hz), 2.58–2.74(2H,m), 2.64(2H,t,J=7.5 Hz), 3.66(3H,s), 4.65(1H,dd,J=7.5,5 Hz), 7.08(4H,s), 7.16(2H,d,J=8.5 Hz), 7.27(2H,d,J=8.5 Hz)

Reference Example 119

Methyl 4-[4-[3-(3-Fluorophenyl)-1-hydroxypropyl] phenyl]butyrate

Appearance colorless oil

IR spectrum ν (liq) cm⁻¹: 3464, 1738

Mass spectrum m/z: 330 (M⁺)

NMR spectrum δ (CDCl₃) ppm: 1.80(1H,brs), 1.95(2H, qn,J=7.5 Hz), 1.97–2.04(1H,m), 2.07–2.16(1H,m), 2.33(2H, t,J=7.5 Hz), 2.60–2.78(2H,m), 2.65(2H,t,J=7.5 Hz), 3.67(3H,s), 4.62–4.68(1H,m), 6.84–6.91(2H,m), 6.96(1H,d, J=8 Hz), 7.17(2H,d,J=8 Hz), 7.19–7.25(1H,m), 7.26(2H,d, J=8 Hz)

Reference Example 120

Methyl 4-[4-[3-(4-Chlorophenyl)-1-hydroxypropyl]phenyl]butyrate

Appearance colorless oil

IR spectrum ν (liq) cm$^{-1}$: 3464, 1738

Mass spectrum m/z: 346, 348 (M$^+$, 3:1)

NMR spectrum δ (CDCl$_3$) ppm: 1.81(1H,brs), 1.94–2.02(1H,m), 1.95(2H,qn,J=7.5 Hz), 2.05–2.14(1H,m), 2.33(2H,t,J=7.5 Hz), 2.59–2.75(2H,m), 2.64(2H,t,J=7.5 Hz), 3.66(3H,s), 4.64(1H,brt), 7.11(2H,d,J=8.5 Hz), 7.16(2H,d,J=8 Hz), 7.21–7.28(4H,m)

Reference Example 121

Methyl 4-[4-[1-Chloro-2-phenylethyl)phenyl]butyrate

To a solution of 3.49 g of methyl 4-[4-(1-hydroxy-2-Phenylethyl)phenyl]butyrate in 17 ml of benzene, 1.10 ml of thionyl chloride was added dropwise under ice-cooling, and then stirring was continued at room temperature for 1.5 hours. The reaction solvent was removed under reduced pressure, and the residue was dissolved in ether. The ether layer was washed with water and dried, and then the solvent was removed under reduced pressure to yield 3.30 g of pale yellow oil.

IR spectrum ν (liq) cm$^{-1}$: 1738

Mass spectrum m/z: 316, 318 (M$^+$, 3:1)

NMR spectrum δ (CDCl$_3$) ppm: 1.95(2H,qn,J=7.5 Hz), 2.32(2H,t,J=7.5 Hz), 2.64(2H,t,J=7.5 Hz), 3.32(1H,dd,J=14,8 Hz), 3.38(1H,dd,J=14,8 Hz), 3.66(3H,s), 5.03(1H,t,J=8 Hz), 7.08-7.16(4H,m), 7.18–7.27(5H,m)

The compounds of Reference Examples 122 through 173 shown in Tables 27 to 36 were obtained in the same manner as described in Reference Example 121.

TABLE 27

| Reference Example No. | Compound Appearance | IR ν (liq) cm$^{-1}$ | NMR δ (CDCl$_3$) |
|---|---|---|---|
| 122 | Methyl 3-[4-(1-Chloro-2-phenylethyl)phenyl]-propionate<br>pale brown oil | 1738 | 2.62(2H, t, J=7.5Hz), 2.94(2H, t, J=7.5Hz), 3.32(1H, dd, J=14, 7Hz), 3.37 (1H, dd, J=14, 8Hz), 3.67(3H, s), 5.02 (1H, dd, J=8, 7Hz), 7.10–7.17(4H, m), 7.19–7.28(5H, m) |
| 123 | Methyl 4-[4-[1-Chloro-2-(2-fluorophenyl)ethyl]-phenyl]butyrate<br>pale brown oil | 1738 | 1.93(2H, qn, J=7.5Hz), 2.31(2H, t, J=7.5(Hz), 2.64(2H, t, J=7.5Hz), 3.36(1H, dd, J=14, 6.5Hz), 3.40(1H, dd, J=14, 8Hz), 3.66(3H, s), 5.11(1H, dd, J=8, 6.5Hz), 6.97–7.14(4H, m), 7.14(2H, d, J=8Hz), 7.30(2H, d, J=Hz) |
| 124 | Methyl 4-[4-[1-Chloro-2-(3-fluorophenyl)ethyl]-phenyl]butyrate<br>pale brown oil | 1736 | 1.95(2H, qn, J=7.5Hz), 2.32(2H, t, J=7.5Hz), 2.64(2H, t, J=7.5Hz), 3.31(1,H dd, J=14, 6.5Hz), 3.37(1H, dd, J=14, 8Hz), 3.67(3H, s), 5.01(1H, dd, J=8, 6.5Hz), 6.82(1H, d, J=10Hz), 6.88–6.96 (2H, m), 7.14(2H, d, J=8Hz), 7.17–7.26 (1H, m), 7.26(2H, d, J=8Hz) |
| 125 | Methyl 4-[4-[1-Chloro-(4-fluorophenyl)ethyl]-phenyl]butyrate<br>pale brown oil | 1738 | 1.95(2H, qn, J=7.5Hz), 2.32(2H, t, J=7.5Hz), 2.64(2H, t, J=7.5Hz), 3.28(1H, dd, J=14, 7.5Hz), 3.35(1H, dd, J=14, 7.5Hz), 3.67(3H, s), 4.97(1H, t, J=7.5Hz), 6.93(2H, t, J=8.5Hz), 7.05(2H, dd, J=8.5, 5Hz), 7.14(2H, d, J=8Hz), 7.24(2H, d, J=8Hz) |
| 126 | Methyl 4-[4-[1-Chloro-2-(4-chlorophenyl)ethyl]-phenyl]butyrate<br>pale brown oil | 1738 | 1.95(2H, qn, J=7.5Hz), 2.32(2H, t, J=7.5Hz), 2.64(2H, t, J=7.5Hz), 3.28(1H, dd, J=14, 7Hz), 3.34(1H, dd, J=14, 7Hz), 3.67(3H, s), 4.98(1H, t, J=7Hz), 7.02(2H, d, J=8.5Hz), 7.14(2H, d, J=8Hz), 7.21(2H, d, J=8.5Hz), 7.24(2H, d, J=8Hz) |
| 127 | Methyl 4-[4-[1-Chloro-2-(p-tolyl)ethyl]phenyl]-butyrate<br>pale yellow oil | 1738 | 1.95(2H, qn, J=7.5Hz), 2.30(2H, t, J=7.5Hz), 2.32(3H, s), 2.64(2H, t, J=7.5Hz), 3.31(2H, dd, J=8, 6.5Hz), 3.66 (3H, s), 5.01(1H, dd, J=8, 6.5Hz), 7.00 (2H, d, J=8Hz), 7.06(2H, d, J=8Hz), 7.13 (2H, d, J=8.5Hz), 7.23(2H, d, J=8.5Hz) |

TABLE 28

| Reference Example No. | Compound Appearance | IR ν (liq) cm⁻¹ | NMR δ (CDCl₃) |
|---|---|---|---|
| 128 | Methyl 4-[4-(1-Chloro-ethyl)phenyl]butyrate<br>pale brown oil | 1738 | 1.84(3H, d, J=6.5Hz), 1.95(2H, qn, J=7.5Hz), 2.33(2H, t, J=7.5Hz), 2.65(2H, t, J=7.5Hz), 3.66(3H, s), 5.08(1H, q, J=6.5Hz), 7.17(2H, d, J=8.5Hz), 7.35 (2H, d, J=8.5Hz) |
| 129 | Methyl 4-[4-(1-Chloro-propyl)phenyl]butyrate<br>pale brown oil | 1740 | 0.99(3H, t, J=7.5Hz), 1.95(2H, qn, J=7.5Hz), 2.03–2.16(2H, m), 2.33(2H, t, J=7.5Hz), 2.65(2H, t, J=7.5Hz), 3.66(3H, s), 4.77(1H, t, J=7Hz), 7.16(2H, d, J=8Hz), 7.29(2H, d, J=8Hz) |
| 130 | Methyl 5-[4-(1-Chloro-2-phenylethyl)phenyl]-valerate<br>colorless oil | 1736 | 1.60–1.70(4H, m), 2.33(2H, t, J=7Hz), 2.62(2H, t, J=7Hz), 3.33(1H, dd, 14, 7Hz), 3.38(1H, dd, J=14, 8Hz), 3.66 (3H, s), 5.03(1H, dd, J=8, 7Hz), 7.11–7.34(4H, m), 7.22–7.27(5H, m) |
| 131 | Methyl 4[4-(1-Chloro butyl)phenyl]butyrate<br>colorless oil | 1738 | 0.93(3H, t, J=7.5Hz), 1.29–1.40(1H, m), 1.43–1.56(1H, m), 1.91–2.03(1H, m), 1.95(2H, qn, J=7.5Hz), 2.06–2.15 (1H, m), 2.33(2H, t, J=7.5Hz), 2.64(2H, t, J=7.5Hz), 3.66(3H, s), 4.85(1H, t, J=7.5Hz), 7.16(2H, d, J=8.5Hz), 7.29(2H, d, J=8.5Hz) |
| 132 | Methyl 4-[4-(1-Chloro pentyl)9 phenyl]butyrate<br>pale yellow oil | 1740 | 0.89(3H, t, J=7Hz), 1.23–1.40(3H, m), 1.40–1.50(1H, m), 1.95(2H, qn, J=7.5Hz), 1.97–2.06(1H, m), 2.07–2.18(1,H Hm), 2.33(2H, t, J=7.5Hz), 2.64(2H, t, J=7.5Hz), 3.66(3H, s), 4.83(1H, dd, , J=8, 7Hz), 7.16(2H, d, J=8Hz), 7.29 (2H, d, J=8Hz) |
| 133 | Methyl 4-[4-(1-Chloro-hexyl)phenyl]butyrate<br>pale brown oil | 1738 | 0.87(3H, t, J=7Hz), 1.22–1.39(5H, m), 1.40–1.50(1H, m), 1.95(2H, qn, J=7.5Hz), 1.96–2.05(1H, m), 2.06–2.16(1H, m), 2.33(2H, t, J=7.5Hz), 2.64(2H, t, J=7.5Hz), 3.66(3H, s), 4.83(1H, dd, J=8, 7Hz), 7.16(2H, d, J=8Hz), 7.29 (2H, d, J=8Hz) |

TABLE 29

| Reference Example No. | Compound Appearance | IR ν (liq) cm⁻¹ | NMR δ0 (CDCl₃) |
|---|---|---|---|
| 134 | Methyl 4-[4-(1-Chloro-decyl)phenyl]butyrate<br>pale yellow oil | 1740 | 0.88(3H, t, J=7Hz), 1.20–1.35(13H, m), 1.40–1.50(1H, m), 1.95(2H, qn, J=7.5Hz), 1.95–2.04(1H, m), 2.10–2.15 (1H, m), 2.33(2H, t, J=7.5Hz), 2.64(2H, t, J=7.5Hz), 3.66(3H, s), 4.83(1H, dd, J=8, 6.5Hz), 7.16(2H, d, J=8Hz), 7.29 (2H, d, J=8Hz) |
| 135 | Methyl 4-[4-(1-Chloro-2-methylpropyl)phenyl]-butyrate<br>pale yellow oil | 1738 | 0.86(3H, d, J=7Hz), 1.10(3H, d, J=7Hz), 1.95(2H, qn, J=7.5Hz), 2.22(1H, m), 2.33(2H, t, J=7.5Hz), 2.64(2H, t, J=7.5Hz), 3.66(3H, s), 4.61(1H, d, J=7Hz), 7.14(2H, d, J=8Hz), 7.25(2H, d, J=8Hz) |
| 136 | Methyl 4-[4-(1-Chloro-3-methylbutyl)phenyl]-butyrate<br>pale yellow oil | 1740 | 0.93(3H, d, J=7Hz), 0.94(3H, d, J=7Hz), 1.69–1.77(1H, m), 1.83(1H, dt, J=14.5, 7Hz), 1.95(2H, qn, J=7.5Hz), 2.05 (1H, ddd, J=14.5, 8.5, 7Hz), 2.33(2H, t, J=7.5Hz), 2.64(2H, t, J=7.5Hz), 3.67 (3H, s), 4.92(1H, dd, J=14.5, 7Hz), 7.16(2H, d, J=8Hz), 7.30(2H, d, J=8Hz |
| 137 | Methyl 4-[4-(1-Chloro-4-methylpentyl)phenyl]-butyrate<br>pale yellow oil | 1738 | 0.88(6H, d, J=7Hz), 1.13–1.20(1H, m), 1.35–1.42(1H, m), 1.53–1.62(1H, m), 1.96(2H, qn, J=7.5Hz), 2.00–2.15(2H, m), 2.33(2H, t, J=7.5Hz), 2.65(2H, t, J=7.5Hz), 3.66(3H, s), 4.79(1H, dd, J=14, 6Hz), 7.16(2H, d, J=8Hz), 7.29 (2H, d, J=8Hz) |

TABLE 29-continued

| Reference Example No. | Compound Appearance | IR ν (liq) cm⁻¹ | NMR δ (CDCl₃) |
|---|---|---|---|
| 138 | Methyl 4-[4-(1-Chloro-3,3-dimethylbutyl)phenyl]-butyrate pale yellow oil | 1738 | 0.90(9H, s), 1.95(2H, qn, J=7.5Hz), 2.11 (1H, dd, J=14.5, 6.5Hz), 2.19(1H, dd, J=14.5, 6.5Hz), 2.32(2H, t, J=7.5Hz), 2.64(2H, t, J=7.5Hz), 3.67(3H, s), 4.97(1H, t, J=6.5Hz), 7.15(2H, d, J=8Hz), 7.30(2H, d, J=8Hz) |

TABLE 30

| Reference Example No. | Compound Appearance | IR ν (liq) cm⁻¹ | NMR δ (CDCl₃) |
|---|---|---|---|
| 139 | Methyl 4-[4-(Chlorocyclopentylmethyl)phenyl]-butyrate pale brown oil | 1738 | 1.06–1.14(1H, m), 1.41–1.48(1H, m), 1.50–1.71(5H, m), 2.01–2.08(1H, m), 1.95(2H, qn, J=7.5Hz), 2.33(2H, t, J=7.5Hz), 2.56(1H, m), 2.64(2H, t, J=7.5Hz), 3.66(3H, s), 4.64(1H, d, J=9Hz), 7.14(2H, d, J=8Hz), 7.28(2H, d, J=8Hz) |
| 140 | Methyl 4-[4-(Chlorocyclohexylmethyl)phenyl]-butyrate pale yellow oil | 1738 | 0.82–0.94(1H, m), 1.00–1.30(4H, m), 1.38–1.70(4H, m), 1.75–1.99(2H, m), 1.95(2H, qn, J=7.5Hz), 2.33(2H, t, J=7.5Hz), 2.64(2H, t, J=7.5Hz), 3.67(3H, s), 4.58(1H, d, J=8Hz), 7.14(2H, d, J=8Hz), 7.24(2H, d, J=8Hz) |
| 141 | Methyl 4-[4-(Chlorocycloheptylmethyl)phenyl]-butyrate pale brown oil | 1738 | 1.14–1.25(1H, m), 1.32–1.65(9H, m), 1.65–1.74(1H, m), 1.95(2H, qn, J=7.5Hz), 1.96–2.06(1H, m), 2.06–2.15(1H, m), 2.33(2H, qn, J=7.5Hz), 2.64(2H, t, J=7.5Hz), 3.67(3H, s), 4.73(1H, d, J=7.5Hz), 7.14(2H, d, J=8Hz), 7.26(2H, d, J=8Hz) |
| 142 | Methyl 4-[4-(1-Chloro-2-cyclopentylethyl)phenyl]-butyrate pale brown oil | 1738 | 1.06–1.20(2H, m), 1.45–1.54(2H, m), 1.56–1.66(2H, m), 1.74–1.83(2H, m), 1.85(1H, dt, J=15, 7.5Hz), 1.95(2H, qn, J=7.5Hz), 2.02(1H, dt, J=15, 7.5Hz), 2.15–2.21(1H, m), 2.33(2H, t, J=7.5Hz), 2.65(2H, t, J=7.5Hz), 3.67(3H, s), 4.86(1H, t, J=7.5Hz), 7.16(2H, d, J=8Hz), 7.30(2H, d, J=8Hz) |
| 143 | Methyl 4-[4-(1-Chloro-2-cyclohexylethyl)phenyl]-butyrate pale yellow oil | 1740 | 0.86–1.01(2H, m), 1.10–1.27(3H, m), 1.40–1.50(1H, m), 1.62–1.80(5H, m), 1.84(1H, dt, J=14, 7Hz), 1.95(2H, qn, J=7.5Hz), 2.04(1H, ddd, J=14, 8.5, 6Hz), 2.33(2H, t, J=7.5Hz), 2.64(2H, t, J=7.5Hz), 3.66(3H, s), 4.96(1H, dd, J=8.5, 7Hz), 7.16(2H, d, J=8Hz), 7.29(2H, d, J=8Hz) |

TABLE 31

| Reference Example No. | Compound Appearance | IR ν (liq) cm⁻¹ | NMR δ (CDCl₃) |
|---|---|---|---|
| 144 | Methyl 4-[4-(1-Chloro-3-cyclohexylpropyl)phenyl]-butyrate pale brown oil | 1738 | 0.81–0.93(2H, m), 1.07–1.28(5H, m), 1.32–1.42(1H, m), 1.58–1.76(5H, m), 1.95(2H, qn, J=7.5Hz), 1.97–2.17(2H, m), 2.33(2H, t, J=7.5Hz), 2.64(2H, t, J=7.5Hz), 3.66(3H, s), 4.79(1H, t, J=7.5Hz), 7.15(2H, d, J=8Hz), 7.28(2H, d, J=8Hz) |
| 145 | Methyl 4-[4-(1-Chloro-4-cyclohexylbutyl)phenyl]-butyrate pale brown oil | 1740 | 0.80–0.90(2H, m), 1.08–1.33(7H, m), 1.44–1.52(1H, m), 1.59–1.72(5H, m), 1.92–2.03(1H, m), 1.95(2H, qn, J=7.5Hz), 2.05–2.15(1H, m), 2.33(2H, t, J= |

TABLE 31-continued

| Reference Example No. | Compound Appearance | IR ν (liq) cm$^{-1}$ | NMR δ (CDCl$_3$) |
|---|---|---|---|
| 146 | Methyl 4-[4-(1-Chloro-5-cyclohexylpentyl)phenyl]-butyrate<br>pale brown oil | 1740 | 7.5Hz), 2.64(2H, t, J=7.5Hz), 3.66(3H, s), 4.83(1H, dd, J=8.5, 6.5Hz), 7.16 (2H, d, J=8Hz), 7.29(2H, d, J=8Hz) 0.80–0.88(2H, m), 1.08–1.34(9H, m), 1.40–1.48(1H, m), 1.60–1.72(5H, m), 1.95(2H, qn, J=7.5Hz), 1.95–2.05(1H, m), 2.08–2.15(1H, m), 2.33(2H, t, J= 7.5Hz), 2.64(2H, t, J=7.5Hz), 3.67(3H, s), 4.83(1H, t, J=7Hz), 7.16(2H, d, J=8Hz), 7.29(2H, d, J=8Hz) |
| 147 | Methyl 4-[4-(1-Chloro-6-cyclohexylhexyl)phenyl]-butyrate<br>pale yellow oil | 1738 | 0.79–0.90(2H, m), 1.10–1.55(12H, m), 1.59–1.72(5H, m), 1.95(2H, qn, J=7.5Hz), 1.97–2.16(2H, m), 2.33(2H, t, J= 7.5Hz), 2.64(2H, t, J=7.5Hz), 3.66 (3H, s), 4.83(1H, t, J=7.5Hz), 7.15(2H, d, J=8Hz), 7.29(2H, d, J=8Hz) |
| 148 | Methyl trans-4-[4-[Chloro-(4-methylcyclohexyl)methyl]phenyl]-butyrate<br>pale yellow oil | 1740 | 0.79–0.98(3H, m), 0.86(3H, d, J=6.5Hz), 1.02–1.12(1H, m), 1.24–1.33(1H, m), 1.38–1.50(1H, m), 1.60–1.66(1H, m), 1.70–1.85(2H, m), 1.95(2H, qn, J= 7.5Hz), 2.18–2.24(1H, m), 2.33(2H, t, J=7.5Hz), 2.64(2H, t, J=7.5Hz), 3.67 (3H, s), 4.57(1H, d, J=8Hz), 7.14(2H, d, J=8.5Hz), 7.23(2H, d, J=8.5Hz) |

TABLE 32

| Reference Example No. | Compound Appearance | (liq) cm$^{-1}$ | δ (CDCl$_3$) |
|---|---|---|---|
| 149 | Methyl trans-4-[4-[Chloro(4-pentylcyclohexyl)methyl]phenyl]-butyrate<br>pale yellow oil | 1742 | 0.78–1.32(13H, m), 0.87(3H, t, J=7Hz), 1.40–1.47(1H, m), 1.65–1.71(1H, m), 1.77–1.86(2H, m), 1.95(2H, qn, J=7.5Hz), 2.18–2.25(1H, m), 2.33(2H, t, J=7.5Hz), 2.64(2H, t, J=7.5Hz), 3.66 (3H, s), 4.57(1H, d, J=8Hz), 7.14(2H, d, J=8Hz), 7.23(2H, d, J=8Hz) |
| 150 | Methyl 4-[4-[2-(1-Adamantyl)-1-chloroethyl]-phenyl]butyrate<br>pale yellow oil | 1738 | 1.44–1.68(13H, m), 1.93–1.97(5H, m), 1.98(1H, dd, J=14, 6.5Hz), 2.07(1H, dd, J=14, 6.5Hz), 2.32(2H, t, J=7.5Hz), 2.64(2H, t, J=7.5Hz), 3.66(3H, s), 5.04(1H, t, J=6.5Hz), 7.14(2H, d, J=8.5Hz), 7.29(2H, d, J=8.5Hz) |
| 151 | Methyl 4-[4-[1-Chloro-2-(2-norbornyl)ethyl]phenyl]-butyrate<br>pale brown oil | 1738 | 1.01–1.16(4H, m), 1.27–1.29(1H, m), 1.42–1.52(4H, m), 1.72–1.77(1H, m), 1.94(2H, m), 1.94–2.02(2H, m), 2.12–2.20(1H, m), 2.33(2H, t, J=7.5Hz), 2.64 (2H, t, J=7.5Hz), 3.66(3H, s), 4.84 (1H, m), 7.16(2H, d, J=8Hz), 7.28(2H, d, J=8Hz) |
| 152 | Methyl 4-[4-(1-Chloro-3-phenylpropyl)phenyl]-butyrate<br>pale brown oil | 1738 | 1.95(2H, qn, J=7.5Hz), 2.33(2H, t, J= 7.5Hz), 2.28–2.36(1H, m), 2.40–2.49 (1H, m), 2.65(2H, t, J=7.5Hz), 2.68–2.75 (1H, m), 2.80(1H, ddd, J=14, 9, 5.5Hz), 3.66(3H, s), 4.80(1H, dd, J=9, 5.5Hz), 7.17–7.23(5H, m), 7.27–7.31(4H, m) |
| 153 | Methyl 5-[4-(1-Chloropentyl)phenyl]valerate<br>pale yellow oil | 1738 | 0.89(3H, t, J=7Hz), 1.24–1.40(3H, m), 1.40–1.51(1H, m), 1.60–1.73(4H, m), 1.97–2.07(1H, m), 2.07–2.18(1H, m), 2.33(2H, t, J=7Hz), 2.62(2H, t, J=7Hz), 3.66(3H, s), 4.83(1H, brt, J=7Hz), 7.15(2H, d, J=8.5Hz), 7.28(2H, d, J= 8.5Hz) |

TABLE 33

| Reference Example No. | Compound Appearance | IR ν (liq) cm⁻¹ | NMR δ (CDCl₃) |
|---|---|---|---|
| 154 | Methyl 5-[4-(1-Chloro-hexyl)phenyl]valerate<br>pale yellow oil | 1740 | 0.85–0.90(3H, m), 1.22–1.39(5H, m), 1.41–1.55(1H, m), 1.60–1.72(4H, m), 1.97–2.06(1H, m), 2.06–2.17(1H, m), 2.33(2H, t, J=7Hz), 2.62(2H, t, J=7.5 Hz), 3.66(3H, s), 4.83(1H, dd, J=8, 7Hz), 7.15(2H, d, J=8.5Hz), 7.28(2H, d, J=8.5Hz) |
| 155 | Methyl 5-[4-(1-Chloro-2-cyclohexylethyl)phenyl]-valerate<br>pale brown oil | 1740 | 0.85–1.02(2H, m), 1.09–1.28(3H, m), 1.40–1.50(1H, m), 1.60–1.81(9H, m), 1.80–1.88(1H, m), 2.04(1H, ddd, J=14, 9, 6Hz), 2.33(2H, t, J=7Hz), 2.62(2H, t, J=7Hz), 3.66(3H, s), 4.96(1H, dd, J=9, 6Hz), 7.15(2H, d, J=8Hz), 7.28(2H, d, J=8Hz) |
| 156 | Methyl 4-[4-(1-Chloro-heptyl)phenyl]butyrate<br>pale brown oil | 1740 | 0.87(3H, t, J=7Hz), 1.22–1.34(7H, m.) 1.43–1.50(1H, m), 1.95(2H, qn, J=7.5Hz), 1.95–2.05(1H, m), 2.08–2.16(1H, m), 2.33(2H, t, J=7.5Hz), 2.64(2H, t, J=7.5Hz), 3.67(3H, s), 4.83(1H, t, J=7Hz), 7.16(2H, d, J=8Hz), 7.29(2H, d, J=8Hz) |
| 157 | Methyl 4-[4-(1-Chloro-octyl)phenyl]butyrate<br>pale brown oil | 1740 | 0.87(3H, t, J=7Hz), 1.20–1.33(9H, m) 1.42–1.50(1H, m), 1.95(2H, qn, J=7.5Hz), 1.95–2.05(1H, m), 2.08–2.26(1H, m), 2.33(2H, t, J=7.5Hz), 2.64(2H, t, J=7.5Hz), 3.63(3H, s), 4.83(1H, dd, J=8, 7Hz), 7.16(2H, d, J=8Hz), 7.29 2H, d, J=8Hz) |
| 158 | Methyl 4-[4-(1-Chloro-nonyl)phenyl]butyrate<br>pale brown oil | 1740 | 0.87(3H, t, J=7Hz), 1.18–1.34(11H, m), 1.42–1.50(1H, m), 1.95(2H, qn, J=7.5Hz), 1.95–2.05(1H, m), 2.07–2.15 1H, m), 2.33(2H, t, J=7.5Hz), 2.64(2H, t, J=7.5Hz), 3.66(3H, s), 4.83(1H, dd, J=8, 7Hz), 7.16(2H, d, J=8Hz), 7.29 (2H, d, J=8Hz) |

TABLE 34

| Reference Example No. | Compound Appearance | I R ν (liq) cm⁻¹ | NMR δ (CDCl₃) |
|---|---|---|---|
| 159 | Methyl 4-[4-(1-Chloro-5-methylhexyl)phenyl]-butyrate<br>pale brown oil | 1740 | 0.85(3H, d, J=7Hz), 0.86(3H, d, J=7Hz), 1.16–1.25(2H, m), 1.25–1.35(1H, m), 1.44–1.58(2H, m), 1.95(2H, qn, J=7.5Hz), 1.93–2.03(1H, m), 2.06–2.14 (1H, m), 2.33(2H, t, J=7.5Hz), 2.64(2H, t, J=7.5Hz), 3.66(3H, s), 4.84(1H, dd, J=8, 6.5Hz), 7.16(2H, d, J=8Hz), 7.29(2H, d, J=8Hz) |
| 160 | Methyl 4-[4-(1-Chloro-6-methylheptyl)phenyl]-butyrate<br>pale brown oil | 1740 | 0.85(6H, d, J=6.5Hz), 1.12–1.19(2H, m), 1.23–1.35(3H, m), 1.40–1.55(2H, m), 1.95(2H, qn, J=7.5Hz), 1.95–2.06 (1H, m), 2.07–2.16(1H, m), 2.33(2H, t, J=7.5Hz), 2.64(2H, t, J=7.5Hz), 3.66(3H, s), 4.83(1H, t, J=7.5Hz), 7.16(2H, d, J=8Hz), 7.29(2H, d, J=8Hz) |
| 161 | Methyl 4-[4-(1-Chloro-4,4-dimethylpentyl)phenyl]-butyrate<br>pale brown oil | 1742 | 0.88(9H, s), 1.10(1H, td, J=13, 4.5Hz), 1.43(1H, td, J=13, 4.5Hz), 1.96(2H, qn, J=7.5Hz), 1.95–2.13(2H, m), 2.34(2H, t, J=7.5Hz), 2.65(2H, t, J=7.5Hz), 3.67(3H, s), 4.77(1H, t, J=7.5Hz), 7.16(2H, d, J=8.5Hz), 7.29(2H, d, J=8.5Hz) |
| 162 | Methyl 4-[4-(1-Chloro-5,5-dimethylhexyl)phenyl]-butyrate<br>pale brown oil | 1740 | 0.85(9H, s), 1.15–1.23(2H, m), 1.24–1.35(1H, m), 1.40–1.51(1H, m), 1.91–2.00(1H, m), 1.95(2H, qn, J=7.5Hz), 2.04–2.13(1H, m), 2.33(2H, t, J=7.5Hz), 2.65(2H, t, J=7.5Hz), 3.66(3H, s), 4.85(1H, dd, J=8.5, 6Hz), 7.16(2H, d, |

TABLE 34-continued

| Reference Example No. | Compound Appearance | IR ν (liq) cm⁻¹ | NMR δ (CDCl₃) |
|---|---|---|---|
| 163 | Methyl 4-[4-(1-Chloro-6,6-dimethylheptyl)phenyl]-butyrate<br>pale brown oil | 1742 | 0.85(9H, s), 1.11–1.16(2H, m), 1.21–1.30(3H, m), 1.37–1.49(1H, m), 1.94–2.06(1H, m), 1.95(2H, qn, J=7.5Hz), 2.07–2.17(1H, m), 2.33(2H, t, J=7.5Hz), 2.64(2H, t, J=7.5Hz), 3.66(3H, s), 4.83(1H, dd, J=8, 6Hz), 7.16(2H, d, J=8Hz), 7.29(2H, d, J=8Hz), 7.29(2H, d, J=8.5Hz) J=8.5Hz) |

TABLE 35

| Reference Example No. | Compound Appearance | IR ν (liq) cm⁻¹ | NMR δ (CDCl₃) |
|---|---|---|---|
| 164 | Methyl 4-[4-(1-Chloro-3-cyclopentylpropyl)phenyl]-butyrate<br>pale brown oil | 1740 | 1.00–1.10(2H, m), 1.25–1.35(1H, m), 1.45–1.65(5H, m), 1.70–1.80(3H, m), 1.96(2H, qn, J=7.5Hz), 2.00–2.15(2H, m), 2.33(2H, t, J=7.5Hz), 2.65(2H, t, J=7.5Hz), 3.67(3H, s), 4.82(1H, t, J=7.5Hz), 7.16(2H, d, J=8Hz), 7.29(2H, d, J=8Hz) |
| 165 | Methyl 4-[4-[3-(4-Butoxy-phenyl)-1-chloropropyl]-phenyl]butyrate<br>pale violet oil | 1738 | 0.97(3H, t, J=7.5Hz), 1.49(2H, sex, J=7.5Hz), 1.72–1.79(1H, m), 1.95(2H, qn, J=7.5Hz), 2.23–2.35(1H, m), 2.33(2H, t, J=7.5Hz), 2.36–2.45(1H, m), 2.60–2.76(2H, m), 2.64(2H, t, J=7.5Hz), 3.66(3H, s), 3.94(2H, t, J=7Hz), 4.78(1H, dd, J=8.5, 6Hz), 6.82(2H, d, J=8.5Hz), 7.08(2H, d, J=8.5Hz), 7.16(2H, d, J=8Hz), 7.27(2H, d, J=8Hz) |
| 166 | Methyl 4-[4-(1-Chloro-4-phenylbutyl)phenyl]-butyrate<br>pale yellow oil | 1738 | 1.60–1.69(1H, m), 1.78–1.88(1H, m), 1.95(2H, qn, J=7.5Hz), 2.01–2.09(1H, m), 2.11–2.20(1H, m), 2.33(2H, t, J=7.5Hz), 2.64(4H, t, J=7.5Hz), 3.66(3H, s), 4.84(1H, dd, J=8.5, 6.5Hz), 7.13–7.20(5H, m), 7.24–7.29(4H, m) |
| 167 | Methyl 4-[4-(1-Chloro-5-phenylpentyl)phenyl]-butyrate<br>pale yellow oil | 1738 | 1.32–1.42(1H, m), 1.50–1.68(3H, m), 1.95(2H, qn, J=7.5Hz), 2.00–2.08(1H, m), 2.10–2.19(1H, m), 2.33(2H, t, J=7.5Hz), 2.60(2H, t, J=7.5Hz), 2.64(2H, t, J=7.5Hz), 3.67(3H, s), 4.82(1H, t, J=8Hz), 7.13–7.20(5H, m), 7.24–7.29(4H, m) |
| 168 | Methyl 4-[4-(1-Chloro-6-phenylhexyl)phenyl]-butyrate<br>pale yellow oil | 1738 | 1.28–1.65(6H, m), 1.90–2.05(1H, m), 1.95(2H, qn, J=7.5Hz), 2.06–2.15(1H, m), 2.33(2H, t, J=7.5Hz), 2.58(2H, t, J=7.5Hz), 2.64(2H, t, J=7.5Hz), 3.66(3H, s), 4.81(1H, t), 7.12–7.19(3H, m), 7.15(2H, d, J=8Hz), 7.24–7.30(2H, m)7.27(2H, d, J=8Hz) |

TABLE 36

| Reference Example No. | Compound Appearance | IR ν (liq) cm⁻¹ | NMR δ (CDCl₃) |
|---|---|---|---|
| 169 | Methyl 4-(4-[3-(4-Butyl-phenyl)-1-chloropropyl]-phenyl]butyrate<br>pale yellow oil | 1740 | 0.92(3H, t, J=7.5Hz), 1.35(2H, sex, J=7.5Hz), 1.54–1.62(2H, m), 1.95(2H, qn, J=7.5Hz), 2.26–2.36(1H, m), 2.33(2H, t, J=7.5Hz), 2.39–2.47(1H, m), 2.58(2H, t, J=7.5Hz), 2.64(2H, t, J=7.5Hz), 2.63–2.71(1H, m), 2.76(1H, ddd, J=14, 9, 5.5Hz), 3.66(3H, s), 4.80(1H, dd, J=8.5, 6Hz), 7.06–7.12(4H, m), 7.16(2H, d, J=8.5Hz), 7.28(2H, d, J=8.5Hz) |

TABLE 36-continued

| Reference Example No. | Compound Appearance | I R ν (liq) cm⁻¹ | NMR δ (CDCl₃) |
|---|---|---|---|
| 170 | Methyl 4-[4-[1-Chloro-3-(p-tolyl)propyl]phenyl]-butyrate<br>pale green oil | 1738 | 1.95(2H, qn, J=7.5Hz), 2.25–2.35(1H, m), 2.32(3H, s), 2.33(2H, t, J=7.5Hz), 2.36–2.47(1H, m), 2.60–2.79(2H, m), 2.64(2H, t, J=7.5Hz), 4.79(1H, dd, J=8, 6Hz), 7.07(2H, d, J=8Hz), 7.10(2H, d, J=8Hz), 7.15(2H, d, J=8.5Hz), 7.28(2H, d, J=8.5Hz) |
| 171 | Methyl 4-[4-[1-Chloro-3-(4-fluorophenyl)propyl]-phenyl]butyrate<br>colorless oil | 1738 | 1.95(2H, qn, J=7.5Hz), 2.24–2.46(2H, m), 2.33(2H, t, J=7.5Hz), 2.65(2H, t, J=7.5Hz), 2.68–2.72(1H, m), 2.74–2.81(1H, m), 3.66(3H, s), 4.77(1H, dd, J=8.5, 6.5Hz), 6.97(2H, t, J=8.5Hz), 7.13(2H, dd, J=8.5, 5.5Hz), 7.16(2H, d, J=8Hz), 7.27(2H, d, J=8Hz) |
| 172 | Methyl 4-[4-[1-Chloro-3-(3-fluorophenyl)propyl]-phenyl]butyrate<br>colorless oil | 1738 | 1.95(2H, qn, J=7.5Hz), 2.28–2.35(1H, m), 2.33(2H, t, J=7.5Hz), 2.39–2.47(1H, m), 2.65(2H, t, J=7.5Hz), 2.68–2.75(1H, m), 2.77–2.84(1H, m), 3.66(3H, s), 4.78(1H, dd, J=8.5, 5.5Hz), 6.87–6.96(3H, m), 7.17(2H, d, J=8Hz), 7.22–7.27(1H, m), 7.28(2H, d, J=8Hz) |
| 173 | Methyl 4-[4-[3-(4-Chloro-phenyl)-1-chloropropyl]-phenyl]butyrate<br>pale yellow oil | 1738 | 1.95(2H, qn, J=7.5Hz), 2.24–2.34(1H, m), 2.33(2H, t, J=7.5Hz), 2.37–2.46(1H, m), 2.65(2H, t, J=7.5Hz), 2.66–2.72(1H, m), 2.74–2.82(1H, m), 3.66(3H, s), 4.76(1H, dd, J=8.5, 6Hz), 7.11(2H, d, J=8.5Hz), 7.16(2H, d, J=8Hz), 7.23–7.30(4H, m) |

Reference Example 174

Methyl 4-[4-(1-Azido-2-phenylethyl)phenyl]butyrate

A suspension of 3.30 g of methyl 4-[4-(1-chloro-2-phenylethyl]phenyl]butyrate and 1.35 g of sodium azide in 15 ml of N,N-dimethylformamide was stirred at 100° C. for 3.5 hours. The reaction mixture was added with water and then extracted with ether. The ether layer was washed with water and dried, and then the solvent was removed under reduced pressure to yield 3.10 g of pale brown oil.

IR spectrum ν (liq) cm⁻¹: 2104, 1738

NMR spectrum δ (CDCl₃) ppm: 1.96(2H,qn,J=7.5 Hz), 2.33(2H,t,J=7.5 Hz), 2.65(2H,t,J=7.5 Hz), 3.01(1H,dd,J= 13.5,6 Hz), 3.66(1H,dd,J=13.5,8.5 Hz), 3.67(3H,s), 4.63(1H,dd,J=8.5,6 Hz), 7.14–7.29(9H,m)

The compounds of Reference Examples 175 through 226 shown in Tables 37 to 45 were obtained in the same manner as described in Reference Example 174.

TABLE 37

| Reference Example No. | Compound Appearance | I R ν (liq) cm⁻¹ | NMR δ (CDCl₃) |
|---|---|---|---|
| 175 | Methyl 3-[4-(1-Azido-2-phenylethyl)phenyl]-propionate<br>colorless oil | 2104, 1738 | 2.63(2H, t, J=8Hz), 2.95(2H, t, J=8Hz), 3.00(1H, dd, J=14, 6Hz), 3.06(1H, dd, J=14, 8.5Hz), 3.67(3H, s), 4.63(1H, dd, J=8.5, 6Hz), 7.13–7.29(9H, m) |
| 176 | Methyl 4-[4-[1-Azido-2-(2-fluorophenyl)ethyl]-phenyl]butyrate<br>pale brown oil | 2108, 1738 | 1.96(2H, qn, J=7.5Hz), 2.33(2H, t, J=7.5Hz), 2.65(2H, t, J=7.5Hz), 3.07(2H, d, J=7.5Hz), 3.67(3H, s), 4.71(2H, d, J=7.5Hz), 6.99–7.30(4H, m), 7.17(2H, d, J=8.5Hz), 7.23(2H, d, J=8.5Hz) |
| 177 | Methyl 4-[4-[1-Azido-2-(3-fluorophenyl)ethyl]-phenyl]butyrate<br>pale brown oil | 2104, 1738 | 1.96(2H, qn, J=7.5Hz), 2.33(2H, t, J=7.5Hz), 2.66(2H, t, J=7.5Hz), 2.99(1H, dd, J=14, 6Hz), 3.05(1H, dd, J=14, 8.5Hz), 3.67(3H, s), 4.63(1H, dd, J=8.5, 6Hz), 6.84(1H, d, J=9.5Hz), 6.89–6.95(2H, m), 7.16–7.26(5H, m) |
| 178 | Methyl 4-[4-[1-Azido-2-(4-fluorophenyl)ethyl]-phenyl]butyrate<br>pale brown oil | 2108, 1738 | 1.96(2H, qn, J=7.5Hz), 2.33(2H, t, J=7.5Hz), 2.66(2H, t, J=7.5Hz), 2.97(1H, dd, J=14, 6Hz), 3.03(1H, dd, J=14, 8Hz), 3.67(3H, s), 4.59(1H, dd, J=8, 6Hz), 6.95(2H, t, J=8.5Hz), 7.08(2H, dd, J=8.5, 5.5Hz), 7.17(4H, s) |
| 179 | Methyl 4-[4-[1-Azido-2-(4-chlorophenyl)ethyl]- | 2108, 1738 | 1.96(2H, qn, J=7.5Hz), 2.33(2H, t, J=7.5Hz), 2.65(2H, t, J=7.5Hz), 2.96(1H, |

TABLE 37-continued

| Reference Example No. | Compound Appearance | I R ν (liq) cm⁻¹ | NMR δ (CDCl₃) |
|---|---|---|---|
| | phenyl]butyrate pale brown oil | | dd, J=14, 6Hz), 3.02(1H, dd, J=14, 8Hz), 3.67(3H, s), 4.60(1H, dd, J=8, 6Hz), 7.04(2H, d, J=8.5Hz), 7.17(4H, s), 7.23(2H, d, J=8.5Hz) |
| 180 | Methyl 4-[4-[1-Azido-2-(p-tolyl)ethyl]phenyl]-butyrate pale brown oil | 2104, 1740 | 1.96(2H, qn, J=7.5Hz), 2.32(3H, s), 2.33(2H, (2H, t, J=7.5Hz), 2.65(2H, t, J=7.5Hz), 2.97(1H, dd, J=14, 8.5Hz), 3.02(1H, dd, J=14, 8.5Hz), 3.67(3H, s), 4.60, 4.61(1H, dd, J=8.5Hz), 7.03(2H, d, J=8Hz), 7.09(2H, d, J=8Hz), 7.18(2H, d, J=8Hz), 7.21(2H, d, J=8Hz) |

TABLE 38

| Reference Example No. | Compound Appearance | I R ν (liq) cm⁻¹ | NMR δ (CDCl₃) |
|---|---|---|---|
| 181 | Methyl 4-[4-(1-Azidoethyl)-phenyl]butyrate pale brown oil | 2108, 1738 | 1.52(3H, d, J=6.5Hz), 1.96(2H, qn, J=7.5Hz), 2.33(2H, t, J=7.5Hz), 2.65(2H, t, J=7.5Hz), 3.67(3H, s), 4.58(1H, q, J=6.5Hz), 7.19(2H, d, J=8Hz), 7.24(2H, d, J=8Hz) |
| 182 | Methyl 4-[4-(1-Azido-propyl)phenyl]butyrate pale brown oil | 2104, 1738 | 0.93(3H, t, J=7.5Hz), 1.74–1.89(2H, m), 1.96(2H, qn, J=7.5Hz), 2.33(2H, t, J=7.5Hz), 2.65(2H, t, J=7.5Hz), 3.67(3H, s), 4.31(1H, t, J=7.5Hz), 7.18(2H, d, J=8Hz), 7.21(2H, d, J=8Hz) |
| 183 | Methyl 5-[4-(1-Azido-2-phenylethyl)phenyl]-valerate colorless oil | 2104, 1736 | 1.60–1.67(4H, m), 2.34(2H, t, J=7Hz), 2.63(2H, t, J=7Hz), 3.01(1H, dd, J=1.4, 6Hz), 3.06(1H, dd, J=14, 8.5Hz), 3.67(3H, s), 4.63(1H, dd, J=8.5, 6Hz), 7.14–7.33(9H, m) |
| 184 | Methyl 4-[4-(1-Azidobutyl)-phenyl]butyrate pale yellow oil | 2100, 1738 | 0.92(3H, t, J=7.5Hz), 1.24–1.47(2H, m), 1.67–1.75(1H, m), 1.77–1.86(1H, m), 1.96(2H, qn, J=7.5Hz), 2.34(2H, t, J=7.5Hz), 2.65(2H, t, J=7.5Hz), 3.67(3H, s), 4.38(1H, t, J=7.5Hz), 7.18(2H, d, J=8.5Hz), 7.21(2H, d, J=8.5Hz) |
| 185 | Methyl 4-[4-(1-Azido-pentyl)phenyl]butyrate pale brown oil | 2106, 1738 | 0.89(3H, t, J=7Hz), 1.18–1.43(4H, m), 1.67–1.77(1H, m), 1.78–1.88(1H, m), 1.96(2H, qn, J=7.5Hz), 2.34(2H, t, J=7.5Hz), 2.65(2H, t, J=7.5Hz), 3.67(3H, s), 4.36(1H, t, J=7.5Hz), 7.18(2H, d, J=8.5Hz), 7.21(2H, d, J=8.5Hz) |
| 186 | Methyl 4-[4-(1-Azidohexyl)-phenyl]butyrate colorless oil | 2100, 1738 | 0.87(3H, t, J=7Hz), 1.20–1.35(5H, m), 1.33–1.45(1H, m), 1.67–1.77(1H, m), 1.77–1.87(1H, m), 1.96(2H, qn, J=7.5Hz), 2.34(2H, t, J=7.5Hz), 2.65(2H, t, J=7.5Hz), 3.67(3H, s), 4.36(1H, t, J=7.5Hz), 7.18(2H, d, J=8Hz), 7.21(2H, d, J=8Hz) |
| 187 | Methyl 4-[4-(1-Azidodecyl)-phenyl]butyrate pale yellow oil | 2100, 1742 | 0.87(3H, t, J=7Hz), 1.20–1.40(14H, m), 1.68–1.76(1H, m), 1.78–1.85(1H, m), 1.96(2H, qn, J=7.5Hz), 2.34(2H, t, J=7.5Hz), 2.65(2H, t, J=7.5Hz), 3.67(3H, s), 4.34-4.37(1H, m), 7.18(2H, d, J=8Hz), 7.21(2H, d, J=8Hz) |

TABLE 39

| Reference Example No. | Compound Appearance | I R ν (liq) cm⁻¹ | NMR δ (CDCl₃) |
|---|---|---|---|
| 188 | Methyl 4-[4-(1-Azido-2-methylpropyl)phenyl]- | 2104, 1738 | 0.78(3H, d, J=7Hz), 1.01(3H, d, J=7Hz), 1.92–2.01(1H, m), 1.97(2H, qn, J=7.5Hz), |

TABLE 39-continued

| Reference Example No. | Compound Appearance | IR ν (liq) cm$^{-1}$ | NMR δ (CDCl$_3$) |
|---|---|---|---|
| | butyrate pale yellow oil | | 2.34(2H, t, J=7.5Hz), 2.65(2H, t, J=7.5Hz), 3.67(3H, s), 4.10(1H, d, J=8.5Hz), 7.17(4H, s) |
| 189 | Methyl 4-[4-(1-Azido-3-methylbutyl)phenyl]-butyrate colorless oil | 2104, 1740 | 0.93(6H, d, J=6.5Hz), 1.56(1H, dt, J=13.5, 6.5Hz), 1.60–1.68(1H, m), 1.75(1H, ddd, J=13.5, 9, 6.5Hz), 1.96(2H, qn, J=7.5Hz), 2.34(2H, t, J=7.5Hz), 2.65(2H, t, J=7.5Hz), 3.67(3H, s), 4.43(1H, dd, J=9, 6.5Hz), 7.18(2H, d, J=8Hz), 7.22(2H, d, J=8Hz) |
| 190 | Methyl 4-[4-(1-Azido-4-methylpentyl)phenyl]-butyrate pale yellow oil | 2100, 1740 | 0.87(3H, d, J=7Hz), 0.88(3H, d, J=7Hz), 1.10–1.17(1H, m), 1.26–1.33(1H, m), 1.50–1.59(1H, m), 1.70–1.86(2H, m), 1.96(2H, qn, J=7.5Hz), 2.34(2H, t, J=7.5Hz), 2.66(2H, t, J=7.5Hz), 3.67(3H, s), 4.32(1H, t, J=7Hz), 7.18(2H, d, J=8Hz), 7.21(2H, d, J=8Hz) |
| 191 | Methyl 4-[4-(1-Azido-3,3-dimethylbutyl)phenyl]-butyrate colorless oil | 2104, 1738 | 0.95(9H, s), 1.65(1H, dd, J=14.5, 5Hz), 1.81(1H, dd, J=14.5, 8.5Hz), 1.96(2H, qn, J=7.5Hz), 2.33(2H, t, J=7.5Hz), 2.65(2H, t, J=7.5Hz), 3.67(3H, s), 4.42(1H, dd, J=8.5, 5Hz), 7.18(2H, d, J=8.5Hz), 7.22(2H, d, J=8.5Hz) |
| 192 | Methyl 4-[4-(Azidocyclo-pentylmethyl)phenyl]-butyrate pale brown oil | 2100, 1740 | 1.05–1.14(1H, m), 1.48–1.54(3H, m), 1.54–1.69(3H, m), 1.88–1.93(1H, m), 1.96(2H, qn, J=7.5Hz), 2.27(1H, m), 2.34(2H, t, J=7.5Hz), 2.65(2H, t, J=7.5Hz), 3.67(3H, s), 4.12(1H, d, J=9Hz), 7.17(2H, d, J=8Hz), 7.21(2H, d, J=8Hz) |
| 193 | Methyl 4-[4-(Azidocyclo-hexylmethyl)phenyl]-butyrate pale yellow oil | 2100, 1740 | 0.82–0.94(1H, m), 0.96–1.28(4H, m), 1.33–1.40(1H, m), 1.56–1.69(3H, m), 1.72–1.80(1H, m), 1.92–2.02(1H, m), 1.97(2H, qn, J=7.5Hz), 2.34(2H, t, J=7.5Hz), 2.65(2H, t, J=7.5Hz), 3.67(3H, s), 4.11(1H, d, J=7.5Hz), 7.16(2H, s), 7.17(2H, s) |

TABLE 40

| Reference Example No. | Compound Appearance | IR ν (liq) cm$^{-1}$ | NMR δ (CDCl$_3$) |
|---|---|---|---|
| 194 | Methyl 4-[4-(Azidocyclo-heptylmethyl)phenyl]-butyrate pale brown oil | 2104, 1740 | 1.06–1.16(1H, m), 1.24–1.40(2H, m), 1.36–1.64(7H, m), 1.64–1.74(1H, m), 1.81–1.95(2H, m), 1.97(2H, qn, J=7.5Hz), 2.34(2H, t, J=7.5Hz), 2.65(2H, t, J=7.5Hz), 3.67(3H, s), 4.20(1H, d, J=8Hz), 7.17(4H, s) |
| 195 | Methyl 4-[4-(1-Azido-2-cyclopentylethyl)phenyl]-butyrate pale yellow oil | 2100, 1738 | 1.08–1.20(2H, m), 1.46–1.54(2H, m), 1.57–1.65(2H, m), 1.70–1.83(4H, m), 1.84–1.90(1H, m), 1.96(2H, qn, J=7.5Hz), 2.34(2H, t, J=7.5Hz), 2.65(2H, t, J=7.5Hz), 3.67(3H, s), 4.38(1H, t, J=7.5Hz), 7.18(2H, d, J=8Hz), 7.22(2H, d, J=8Hz) |
| 196 | Methyl 4-[4-(1-Azido-2-cyclohexylethyl)phenyl]-butyrate pale yellow oil | 2100, 1740 | 0.85–1.00(2H, m), 1.10–1.27(3H, m), 1.33–1.40(1H, m), 1.56(1H, qn, J=7Hz), 1.61–1.80(6H, m), 1.96(2H, qn, J=7.5Hz), 2.34(2H, t, J=7.5Hz), 2.65(2H, t, J=7.5Hz), 3.67(3H, s), 4.47(1H, dd, J=8.5, 6Hz), 7.18(2H, d, J=8Hz), 7.21(2H, d, J=8Hz) |
| 197 | Methyl 4-[4-(1-Azido-3-cyclohexylpropyl)phenyl]-butyrate pale brown oil | 2100, 1740 | 0.80–0.92(2H, m), 1.06–1.34(6H, m), 1.59–1.72(5H, m), 1.69–1.87(2H, m), 1.96(2H, qn, J=7.5Hz), 2.34(2H, t, J=7.5Hz), 2.65(2H, t, J=7.5Hz), 3.67(3H, s), 4.32(1H, t, J=7.5Hz), 7.18(2H, d, J=8Hz), 7.20(2H, d, J=8Hz) |

TABLE 40-continued

| Reference Example No. | Compound Appearance | IR ν (liq) cm⁻¹ | NMR δ (CDCl₃) |
|---|---|---|---|
| 198 | Methyl 4-[4-(1-Azido-4-cyclohexylbutyl)phenyl]-butyrate<br>pale brown oil | 2100, 1738 | 0.79–0.90(2H, m), 1.09–1.30(7H, m), 1.35–1.44(1H, m), 1.60–1.73(6H, m), 1.76–1.84(1H, m), 1.96(2H, qn, J=7.5Hz), 2.34(2H, t, J=7.5Hz), 2.65(2H, t, J=7.5Hz), 3.67(3H, s), 4.36(1H, t, J=7.5Hz), 7.18(2H, d, J=8.5Hz), 7.21(2H, d, J=8.5Hz) |
| 199 | Methyl 4-[4-(1-Azido-5-cyclohexylpentyl)phenyl]-butyrate<br>pale yellow oil | 2100, 1742 | 0.80–0.88(2H, m), 1.08–1.40(10H, m) 1.60–1.75(6H, m), 1.78–1.86(1H, m), 1.96(2H, qn, J=7.5Hz), 2.34(2H, t, J=7.5Hz), 2.65(2H, t, J=7.5Hz), 3.67(3H, s), 4.36(1H, t, J=7Hz), 7.18(2H, d, J=8.5Hz), 7. 21(2H, d, J=8.15Hz) |

TABLE 41

| Reference Example No. | Compound Appearance | IR ν (liq) cm⁻¹ | NMR δ (CDCl₃) |
|---|---|---|---|
| 200 | Methyl 4-[4-(1-Azido-6-cyclohexylhexyl)phenyl]-butyrate<br>pale brown oil | 2100, 1742 | 0.79–0.92(2H, m), 1.08–1.44(12H, m) 1.60–1.86(7H, m), 1.96(2H, qn, J=7.5Hz), 2.34(2H, t, J=7.5Hz), 2.65(2H, t, J=7.5Hz), 3.67(3H, s), 4.36(1H, t, J=7.5Hz), 7.18(2H, d, J=8Hz), 7.21(2H, d, J=8Hz) |
| 201 | Methyl trans-4-[4-[Azido(4-methylcyclohexyl)-methyl]phenyl]butyrate<br>pale yellow oil | 2100, 1738 | 0.76–1.08(4H, m), 0.85(3H, d, J=6Hz), 1.18–1.38(2H, m), 1.50–1.65(2H, m), 1.70–1.76(1H, m), 1.97(2H, qn, J=7.5Hz), 1.97–2.04(1H, m), 2.34(2H, t, J=7.5Hz), 2.65(2H, t, J=7.5Hz), 3.67(3H, 3H, s), 4.09(1H, d, J=8.5Hz), 7.15(2H, d, J=8.5Hz), 7.17(2H, d, J=8.5Hz) |
| 202 | Methyl trans-4-[4-(Azido(4-pentylcyclohexyl)-methyl]phenyl]butyrate<br>pale yellow viscous oil | 2100, 1742 | 0.74–1.41(14H, m), 0.87(3H, t, J=7.5Hz), 1.52–1.61(1H, m), 1.64–1.70(1H, m), 1.76–1.82(1H, m), 1.97(2H, qn, J=7.5Hz), 1.98–2.04(1H, m), 2.34(2H, t, J=7.5Hz), 2.65(2H, t, J=7.5Hz), 3.67(3H, s), 4.09(1H, d, J=8Hz), 7.16(2H, d, J=6Hz), 7.17(2H, d, J=6Hz) |
| 203 | Methyl 4-[4-[2-(1-Adamantyl)-1-azidoethyl]-phenyl]butyrate<br>pale yellow oil | 2104, 1740 | 1.45–1.74(15H, m), 1.91–1.98(4H, m), 2.33(2H, t, J=7.5Hz), 2.65(2H, t, J=7.5Hz), 3.67(3H, s), 4.47(1H, dd, J=8, 4Hz), 7.17(2H, d, J=8Hz), 7.21(2H, d, J=8Hz) |
| 204 | Methyl 4-[4-[1-Azido-2-(2-norbornyl)ethyl]phenyl]-butyrate<br>pale yellow oil | 2100, 1740 | 1.03–1.16(4H, m), 1.22–1.30(1H, m), 1.43–1.54(5H, m), 1.60–1.71(1H, m), 1.93–1.99(3H, m), 2.20(1H, s), 2.34 2H, t, J=7.5Hz), 2.65(2H, t, J=7.5Hz) 3.67(3H, s), 4.36(1H, m), 7.18(2H, d, J=8Hz), 7.20(2H, d, J=8Hz) |
| 205 | Methyl 4-[4-(1-Azido-3-phenylpropyl)phenyl]-butyrate<br>pale brown oil | 2100, 1738 | 1.96(2H, qn, J=7.5Hz), 2.00–2.08(1H, m), 2.10–2.19(1H, m), 2.34(2H, t, J=7.5Hz), 2.61–2.74(2H, m), 2.66(2H, t, J=7.5Hz), 3.67(3H, s), 4.37(1H, dd, J=8.5, 6Hz), 7.14–7.23(7H, m), 7.29(2H, t, J=7.5Hz) |

TABLE 42

| Reference Example No. | Compound Appearance | IR ν (liq) cm⁻¹ | NMR δ (CDCl₃) |
|---|---|---|---|
| 206 | Methyl 5-[4-(1-Azido-pentyl)phenyl]valerate | 2100, 1740 | 0.88(3H, t, J=7.5Hz), 1.18–1.42(4H, m), 1.60–1.90(6H, m), 2.34(2H, t, J=7Hz), |

TABLE 42-continued

| Reference Example No. | Compound Appearance | IR ν (liq) cm⁻¹ | NMR δ (CDCl₃) |
|---|---|---|---|
| | pale brown oil | | 2.63(2H, t, J=7Hz), 3.66(3H, s), 4.36(1H, brt, J=7.5Hz), 7.17(2H, d, J=8.5Hz), 7.20(2H, d, J=8.5Hz) |
| 207 | Methyl 5-[4-(1-Azidohexyl)-phenyl]valerate pale brown oil | 2100, 1740 | 0.87(3H, t, J=7Hz), 1.21–1.46(6H, m), 1.61–1.88(6H, m), 2.34(2H, t, J=7Hz), 2.63(2H, t, J=7.5Hz), 3.66(3H, s), 4.36(1H, t, J=7Hz), 7.17(2H, d, J=8.5Hz), 7.20(2H, d, J=8.5Hz) |
| 208 | Methyl 5-[4-(1-Azido-2-cyclohexylethyl)phenyl]-valerate pale brown oil | 2100, 1740 | 0.87–1.00(2H, m), 1.09–1.28(3H, m), 1.29–1.41(1H, m), 1.51–1.80(11H, m), 2.34(2H, t, J=7Hz), 2.63(2H, t, J=7.5Hz), 3.67(3H, s), 4.46(1H, dd, J=9, 6Hz), 7.17(2H, d, J=8.5Hz), 7.20(2H, d, J=8.5Hz) |
| 209 | Methyl 4-[4-(1-Azido-heptyl)phenyl]butyrate pale yellow oil | 2100, 1740 | 0.87(3H, t, J=7Hz), 1.20–1.41(8H, m), 1.68–1.77(1H, m), 1.78–1.86(1H, m), 1.96(2H, qn, J=7.5Hz), 2.34(2H, t, J=7.5Hz), 2.65(2H, t, J=7.5Hz), 3.67(3H, s), 4.36(1H, t, J=7Hz), 7.18(2H, d, J=8.5Hz), 7.21(2H, d, J=8.5Hz) |
| 210 | Methyl 4-[4-(1-Azidooctyl)-phenyl]butyrate pale yellow oil | 2100, 1742 | 0.87(3H, t, J=7Hz), 1.20–1.43(10H, m), 1.68–1.76(1H, m), 1.79–1.86(1H, m), 1.96(2H, qn, J=7.5Hz), 2.34(2H, t, J=7.5Hz), 2.65(2H, t, J=7.5Hz), 3.67(3H, s), 4.36(1H, t, J=7Hz), 7.18(2H, d, J=8.5Hz), 7.21(2H, d, J=8.5Hz) |
| 211 | Methyl 4-[4-(1-Azidononyl)-phenyl]butyrate pale yellow oil | 2100, 1740 | 0.87(3H, t, J=7Hz), 1.19–1.42(12H, m), 1.67–1.75(1H, m), 1.78–1.86(1H, m), 1.96(2H, qn, J=7.5Hz), 2.34(2H, t, J=7.5Hz), 2.65(2H, t, J=7.5Hz), 3.67(3H, s), 4.36(1H, t, J=7Hz), 7.18(2H, d, J=8.5Hz), 7.21(2H, d, J=8.5Hz) |

TABLE 43

| Reference Example No. | Compound Appearance | IR ν (liq) cm⁻¹ | NMR δ (CDCl₃) |
|---|---|---|---|
| 212 | Methyl 4-[4-(1-Azido-5-methylhexl)phenyl]-butyrate pale yellow oil | 2100, 1738 | 0.85(3H, d, J=7Hz), 0.85(3H, d, J=7Hz), 1.16–1.20(2H, m), 1.21–1.31(1H, m), 1.34–1.44(1H, m), 1.46–1.55(1H, m), 1.65–1.73(1H, m), 1.76–1.84(1H, m), 1.96(2H, qn, J=7.5Hz), , 2.34(2H, t, J=7.5Hz), 2.65(2H, t, J=7.5Hz), 3.67(3H, s), 4.37(1H, t, J=7.5Hz), 7.18(2H, d, J=8Hz), 7.21(2H, d, J=8Hz) |
| 213 | Methyl 4-[4-(1-Azido-6-methylheptyl)phenyl]-butyrate pale brown oil | 2100, 1742 | 0.85(6H, d, J=7Hz), 1.08–1.20(2H, m), 1.20–1.40(4H, m), 1.42–1.57(1H, m), 1.66–1.77(1H, m), 1.77–1.87(1H, m), 1.96(2H, qn, J=7.5Hz), 2.34(2H, t, J=7.5Hz), 2.65(2H, t, J=7.5Hz), 3.67(3H, s), 4.36(1H, t, J=7.5Hz), 7.18(2H, d, J=8Hz), 7.21(2H, d, J=8Hz) |
| 214 | Methyl 4-[4-(1-Azido-4,4-dimethylpentyl)phenyl]-butyrate pale yellow oil | 2100, 1740 | 0.87(9H, s), 1.10(1H, td, J=13, 5Hz), 1.34(1H, td, J=13, 5Hz), 1.66–1.83(2H, m), 1.97(2H, qn, J=7.5Hz), 2.34(2H, t, J=7.5Hz), 2.66(2H, t, J=7.5Hz), 3.67(3H, s), 4.30(1H, t, J=7Hz), 7.19(2H, d, J=8.5Hz), 7.21(2H, d, J=8.5Hz) |
| 215 | Methyl 4-(4-(1-Azido-5,5-dimethylhexyl)phenyl]-butyrate pale yellow oil | 2104, 1740 | 0.85(9H, s), 1.14–1.28(3H, m), 1.31–1.42(1H, m), 1.64–1.72(1H, m), 1.74–1.84(1H, m), 1.96(2H, qn, J=7.5Hz), 2.33(2H, t, J=7.5Hz), 2.65(2H, t, J=7.5Hz), 3.67(3H, s), 4.38(1H, dd, J=8, 6Hz), 7.18(2H, d, J=8.5Hz), 7.21(2H, d, J=8.5Hz) |
| 216 | Methyl 4-[4-(1-Azido-6,6-dimethylhexyl)phenyl]-butyrate | 2100, 1742 | 0.85(9H, s), 1.10–1.16(2H, m), 1.18–1.39(4H, m), 1.69–1.76(1H, m), 1.79–1.89(1H, m), 1.96(2H, qn, J=7.5Hz), 2.34(2H, |

TABLE 43-continued

| Reference Example No. | Compound Appearance | I R ν (liq) cm$^{-1}$ | NMR δ (CDCl$_3$) |
|---|---|---|---|
| | pale brown oil | | t, J=7.5Hz), 2.65(2H, t, J=7.5Hz), 3.67(3H, s), 4.36(1H, t, J=7Hz), 7.18(2H, d, J=8.5Hz), 7.21(2H, d, J= 8.5Hz) |

TABLE 44

| Reference Example No. | Compound Appearance | I R ν (liq) cm$^{-1}$ | NMR δ (CDCl$_3$) |
|---|---|---|---|
| 217 | Methyl 4-[4-(1-Azido-3-cyclopentylpropyl)phenyl]-butyrate pale yellowish brown oil | 2100, 1738 | 1.00–1.10(2H, m), 1.20–1.30(1H, m), 1.35–1.60(5H, m), 1.70–1.80(4H, m), 1.80–1.90(1H, m), 1.96(2H, qn, J=7.5Hz), 2.34(2H, t, J=7.5Hz), 2.65(2H, t, J=7.5Hz), 3.67(3H, s), 4.35(1H, t, J=7.5Hz), 7.18(2H, d, J=8.5Hz), 7.21(2H, d, J=8.5Hz) |
| 218 | Methyl 4-[4-[1-Azido-3-(4-butoxyphenyl)propyl]-phenyl]butyrate pale yellow oil | 2100, 1738 | 0.97(3H, t, J=7.5Hz), 1.49(2H, sex, J= 7.5Hz), 1.72–1.79(2H, m), 1.96(2H, qn, J=7.5Hz), 1.93–2.04(1H, m), 2.06–2.15(1H, m), 2.34(2H, t, J=7.5Hz), 2.54–2.67(2H, m), 2.66(2H, t, J=7.5Hz), 3.66(3H, s), 3.94(2H, t, J=7Hz), 4.35(1H, dd, J=8, 6Hz), 6.82(2H, d, J=8.5Hz), 7.06(2H, d, J=8.5Hz), 7.19(2H, d, J=8.5Hz), 7.21(2H, d, J=8.5Hz) |
| 219 | Methyl 4-[4-(1-Azido-4-phenylbutyl)phenyl]-butyrate pale yellow oil | 2100, 1740 | 1.55–1.61(1H, m), 1.68–1.90(3H, m), 1.96(2H, qn, J=7.5Hz), 2.33(2H, t, J= 7.5Hz), 2.59–2.67(4H, m), 3.66(3H, s), 7.15(1H, t, J=7.5Hz), 7.12–7.20(7H, m), 7.24–7.28(2H, m) |
| 220 | Methyl 4-[4-(1-Azido-5-phenylpentyl)phenyl]-butyrate pale yellow oil | 2100, 1738 | 1.27–1.38(1H, m), 1.40–1.50(1H, m), 1.63(2H, qn, J=7.5Hz), 1.70–1.90(2H, m), 1.96(2H, qn, J=7.5Hz), 2.34(2H, t, J=7.5Hz), 2.59(2H, t, J=7.5Hz), 2.65(2H, t, J=7.5Hz), 3.67(3H, s), 4.36(1H, t, J=7Hz), 7.12-7.21(7H, m), 7.24–7.28(2H, m) |
| 221 | Methyl 4-[4-(1-Azido-6-phenylhexyl)phenyl]-butyrate pale yellow oil | 2100, 1738 | 1.24–1.46(4H, m), 1.60(2H, qn, J=7.5Hz), 1.67–1.76(1H, m), 1.77–1.86(1H, m), 1.96(2H, qn, J=7.5Hz), 2.33(2H, t, J=7.5Hz), 2.58(2H, t, J=7.5Hz), 2.65(2H, t, J=7.5Hz), 3.66(3H, s), 4.35(1H, t, J=7.5Hz), 7.12–7.21(7H, m), 7.24–7.29(2H, m) |

TABLE 45

| Reference Example No. | Compound Appearance | I R ν (liq) cm$^{-1}$ | NMR δ (CDCl$_3$) |
|---|---|---|---|
| 222 | Methyl 4-[4-[1-Azido-3-(4-butylphenyl)propyl]phenyl]-butyrate pale brown oil | 2100, 1740 | 0.92(3H, t, J=7.5Hz), 1.35(2H, sex, J= 7.5Hz), 1.54–1.62(2H, m), 1.96(2H, qn, J=7.5Hz), 1.98–2.07(1H, m), 2.09–2.18(1H, m), 2.34(2H, t, J=7.5Hz), 2.58(2H, t, J=7.5Hz), 2.56–2.70(2H, m), 2.66(2H, t, J=7.5Hz), 3.67(3H, s), 4.36(1H, dd, J=8.5, 6.5Hz), 7.07(2H, d, J=8Hz), 7.10(2H, d, J=8Hz), 7.19(2H, d, J=8Hz), 7.22(2H, d, J=8Hz) |
| 223 | Methyl 4-[4-[1-Azido-3-(p-tolyl)propyl]phenyl]-butyrate pale yellow oil | 2100, 1738 | 1.95–2.06(1H, m), 1.96(2H, qn, J=7.5Hz), 2.07–2.17(1H, m), 2.32(3H, s), 2.34(2H, t, J=7.5Hz), 2.55–2.70(2H, m), 2.66(2H, t, J=7.5Hz), 3.67(3H, s), |

TABLE 45-continued

| Reference Example No. | Compound Appearance | IR ν (liq) cm$^{-1}$ | NMR δ (CDCl$_3$) |
|---|---|---|---|
| 224 | Methyl 4-(4-[1-Azido-3-(4-fluorophenyl)propyl]-phenyl]butyrate colorless oil | 2100, 1740 | 4.36(1H, dd, J=8, 6Hz), 7.05(2H, d, J=8Hz), 7.10(2H, d, J=8Hz), 7.19(2H, d, J=8.5Hz), 7.21(2H, d, J=8.5Hz), 1.94–2.04(1H, m), 1.96(2H, qn, J=7.5Hz), 2.07–2.16(1H, m), 2.34(2H, t, J=7.5Hz), 2.57–2.72(2H, m), 2.66(2H, t, J=7.5Hz), 3.67(3H, s), 4.35(1H, dd, J=8.5, 6Hz), 6.97(2H, t, J=8.5Hz), 7.11(2H, dd, J=8.5, 5.5Hz), 7.20(4H, s) |
| 225 | Methyl 4-[4-[1-Azido-3-(3-fluorophenyl)propyl]-phenyl]butyrate pale yellow oil | 2100, 1738 | 1.97(2H, qn, J=7.5Hz), 2.00–2.06(1H, m), 2.09–2.17(1H, m), 2.34(2H, t, J=7.5Hz), 2.59–2.74(2H, m), 2.66(2H, t, J=7.5Hz), 3.67(3H, s), 4.37(1H, dd, J=8, 6Hz), 6.84–6.96(3H, m), 7.17–7.29(5H, m) |
| 226 | Methyl 4-[4-[1-Azido-3-(4-chlorophenyl)propyl]-phenyl]butyrate pale brown oil | 2104, 1738 | 1.96(2H, qn, J=7.5Hz), 1.96–2.04(1H, m), 2.06–2.18(1H, m), 2.34(2H, t, J=7.5Hz), 2.57–2.71(2H, m), 2.66(2H, t, J=7.5Hz), 3.67(3H, s), 4.35(1H, dd, J=8, 6Hz), 7.09(2H, d, J=8.5Hz), 7.20(4H, s), 7.25(2H, d, J=8.5Hz) |

Reference Example 227

Methyl 4-[4-(1-Amino-2-phenylethyl)phenyl]butyrate

To a solution of 3.10 g of methyl 4-[4-(1-azido-2-phenylethyl)phenyl]butyrate in 30 ml of methanol, 31 mg of platinum oxide was added, and hydrogenation was carried out at an ordinary temperature and under ordinary pressure for 4.5 hours. After the catalyst was filtered off, the filtrate was concentrated under reduced pressure. The residue was added with dilute hydrochloric acid and washed with ether. The aqueous layer was made alkaline with potassium carbonate and then extracted with ether. The ether layer was washed with water and dried, and then the solvent was removed under reduced pressure to yield 2.16 g of brown oil.

IR spectrum ν (liq) cm$^{-1}$: 3380, 3300, 1738

NMR spectrum δ (CDCl$_3$) ppm: 1.73(2H,brs), 1.95(2H, qn,J=7.5 Hz), 2.32(2H,t,J=7.5 Hz), 2.63(2H,t,J=7.5 Hz), 2.83(1H,dd,J=13.5,9 Hz), 3.01(1H,dd,J=13.5,5 Hz), 3.67(3H,s), 4.17(1H,dd,J=9.5 Hz), 7.08–7.17(4H,m), 7.19–7.22(1H,m), 7.26–7.29(4H,m)

The compounds of Reference Examples 228 through 279 shown in Tables 46 to 54 were obtained in the same manner as described in Reference Example 227.

TABLE 46

| Reference Example No. | Compound Appearance | IR ν (liq) cm$^{-1}$ | NMR δ (CDCl$_3$) |
|---|---|---|---|
| 228 | Methyl 3-[4-(1-Amino-2-phenylethyl)phenyl]-propionate pale brown oil | 3384, 3300, 1738 | 1.83(2H, brs), 2.62(2H, t, J=8Hz), 2.82(1H, dd, J=13.5, 9Hz), 2.94(2H, t, J=8Hz), 3.00(1H, dd, J=13.5, 5Hz), 3.67(3H, s), 4.17(1H, dd, J=9, 5Hz), 7.16(2H, d, J=8Hz), 7.20–7.29(7H, m) |
| 229 | Methyl 4-[4-[1-Amino-2-(2-fluorophenyl)ethyl]phenyl]-butyrate colorless oil | 3384, 3308, 1738 | 1.85(2H, brs), 1.94(2H, qn, J=7.5Hz), 2.32(2H, t, J=7.5Hz), 2.63(2H, t, J=7.5Hz), 2.88(1H, dd, J=13.5, 8.5Hz), 3.03(1H, dd, J=13.5, 5.5Hz), 3.67(3H, s), 4.21(1H, dd, J=8.5, 5.5Hz), 6.99–7.22(4H, m), 7.03(2H, d, J=8Hz), 7.13(2H, d, J=8Hz), 7.27(2H, d, J=8Hz) |
| 230 | Methyl 4-[4-[1-Amino-2-(3-fluorophenyl)ethyl]phenyl]-butyrate colorless oil | 3380, 3310, 1738 | 1.48(2H, brs), 1.95(2H, qn, J=7.5Hz), 2.33(2H, t, J=7.5Hz), 2.64(2H, t, J=7.5Hz), 2.82(1H, dd, J=13.5, 8.5Hz), 2.97(1H, dd, J=13.5, 5Hz), 3.67(3H, s), 4.16(1H, m), 6.84–6.96(3H, m), 7.14(2H, d, J=8Hz), 7.21-7.26(1H, m), 7.25(2H, d, J=8Hz) |
| 231 | Methyl 4-[4-[1-Amino-2-(4-fluorophenyl)ethyl]phenyl]-butyrate pale brown oil | 3384, 3320, 1738 | 1.45(2H, brs), 1.95(2H, qn, J=7.5Hz), 2.33(2H, t, J=7.5Hz), 2.64(2H, t, J=7.5Hz), 2.80(1H, dd, J=13.5, 8.5Hz), 2.94(1H, dd, J=13.5, 5.5Hz), 3.67(3H, s), 4.12(1H, dd, J=8.5, 5.5Hz), 6.95(2H, t, J=8.5Hz), 7.09(2H, dd, J=8.5, 3.5Hz), 7.13(2H, d, J=8Hz), 7.23(2H, d, J=8Hz) |
| 232 | Methyl 4-[4-[1-Amino-2-(4-chlorophenyl)ethyl]phenyl]- | 3384, 3308, | 1.86(2H, brs), 1.95(2H, qn, J=7.5Hz), 2.32(2H, t, J=7.5Hz), 2.63(2H, t, J= |

TABLE 46-continued

| Reference Example No. | Compound Appearance | IR ν (liq) cm⁻¹ | NMR δ (CDCl₃) |
|---|---|---|---|
|  | butyrate colorless oil | 1738 | 7.5Hz), 2.83(1H, dd, J=13.5, 8.5Hz), 2.95(1H, dd, J=13.5, 5.5Hz), 3.67(3H, s), 4.13(1H, dd, J=8.5, 5.5Hz), 7.05(2H, d, J=8.5Hz), 7.13(2H, d, J=8Hz), 7.23(4H, d, J=8.5Hz) |
| 233 | Methyl 4-[4-[1-Amino-2-(p-tolyl)ethyl]phenyl]-butyrate pale brown oil | 3380, 3300, 1738 | 1.95(2H, qn, J=7.5Hz), 2.32(3H, s), 2.33(2H, t, J=7.5Hz), 2.64(2H, t, J=7.5Hz), 2.75(1H, dd, J=14, 9Hz), 2.96(1H, dd, J=14, 5Hz), 3.67(3H, s), 4.14(1H, dd, J=9, 5Hz), 7.07(2H, , d, J=7.5Hz), 7.09(2H, d, J=7.5Hz), 7.14(2H, d, J=7.5Hz), 7.28(2H, d, J=7.5Hz) |

TABLE 47

| Reference Example No. | Compound Appearance | IR ν (liq) cm⁻¹ | NMR δ (CDCl₃) |
|---|---|---|---|
| 234 | Methyl 4-[4-(1-Aminoethyl)-phenyl]butyrate pale brown oil | 3376, 3312, 1738 | 1.39(3H, d, J=6.5Hz), 1.90–1.99(2H, br), 1.95(2H, qn, J=7.5Hz), 2.33(2H, t, J=7.5Hz), 2.63(2H, t, J=7.5Hz), 3.66(3H, s), 4.10(1H, q, J=6.5Hz), 7.14(2H, d, J=8Hz), 7.27(2H, d, J=8Hz) |
| 235 | Methyl 4-[4-(1-Amino-propyl)phenyl]butyrate colorless oil | 3384, 1738 | 0.86(3H, t, J=7.5Hz), 1.70(2H, m), 1.92(2H, brs), 1.95(2H, qn, J=7.5Hz), 2.33(2H, t, J=7.5Hz), 2.63(2H, t, J=7.5Hz), 3.66(3H, s), 3.79(1H, t, J=7Hz), 7.13(2H, d, J=8Hz), 7.23(2H, d, J=8Hz) |
| 236 | Methyl 5-[4-(1-Amino-2-phenylethyl)phenyl]-valerate pale brown oil | 3384, 3310, 1738 | 1.60–1.70(4H, m), 1.91(2H, brs), 2.33(2H, t, J=7.5Hz), 2.61(2H, t, J=7.5Hz), 2.83(1H, dd, J=13.5, 8.5Hz), 3.01(1H, dd, J=13.5, 5Hz), 3.66(3H, s), 4.17(1H, dd, J=8.5, 5Hz), 7.13(2H, d, J=8.5Hz), 7.16–7.29(7H, m) |
| 237 | Methyl 4-[4-(1-Aminobutyl)-phenyl]butyrate pale yellow oil | 3376, 3300, 1738 | 0.90(3H, t, J=7.5Hz), 1.17–1.29(1H, m), 1.30–1.56(3H, m), 1.56–1.70(2H, m), 1.95(2H, qn, J=7.5Hz), 2.33(2H, t, J=7.5Hz), 2.63(2H, t, J=7.5Hz), 3.66(3H, s), 3.86(1H, t, J=7Hz), 7.13(2H, d, J=8.5Hz), 7.22(2H, d, J=8.5Hz) |
| 238 | Methyl 4-[4-(1-Amino-pentyl)phenyl]butyrate colorless oil | 3384, 3300, 1738 | 0.87(3H, t, J=7Hz), 1.12–1.24(1H, m), 1.24–1.37(3H, m), 1.51(2H, brs), 1.57–1.72(2H, m), 1.95(2H, qn, J=7.5Hz), 2.33(2H, t, J=7.5Hz), 2.63(2H, t, J=7.5Hz), 3.67(3H, s), 3.84(1H, t, J=7Hz), 7.13(2H, d, J=8Hz), 7.22(2H, d, J=8Hz) |
| 239 | Methyl 4-[4-(1-Aminohexyl)-phenyl]butyrate colorless oil | 3384, 3305, 1738 | 0.86(3H, t, J=7Hz), 1.15–1.39(6H, m), 1.50(2H, brs), 1.56–1.70(2H, m), 1.95(2H, qn, J=7.5Hz), 2.33(2H, t, J=7.5Hz), 2.63(2H, t, J=7.5Hz), 3.66(3H, s), 3.84(1H, t, J=7Hz), 7.13(2H, d, J=8Hz), 7.22(2H, d, J=8Hz) |

TABLE 48

| Reference Example No. | Compound Appearance | IR ν (liq) cm⁻¹ | NMR δ (CDCl₃) |
|---|---|---|---|
| 240 | Methyl 4-[4-(1-Aminodecyl)-phenyl)butyrate colorless oil | 3384, 3320, 1742 | 0.87(3H, t, J=7Hz), 1.16–1.34(14H, m, 1.49(2H, brs), 1.60–1.66(2H, m), 1.95(2H, qn, J=7.5Hz), 2.33(2H, t, J=7.5Hz), 2.63(2H, t, J=7.5Hz), 3.67(3H, s), 3.83(1H, t, J=7Hz), 7.13(2H, d, J= |

TABLE 48-continued

| Reference Example No. | Compound Appearance | IR ν (liq) cm$^{-1}$ | NMR δ (CDCl$_3$) |
|---|---|---|---|
| 241 | Methyl 4-[4-(1-Amino-2-methylpropyl)phenyl]-butyrate colorless oil | 3384, 3320, 1738 | 8Hz), 7.22(2H, d, J=8Hz) 0.77(3H, d, J=7Hz), 0.98(3H, d, J=7Hz), 1.87(1H, m), 1.95(2H, qn, J=7.5Hz), 1.80–2.20(2H, brs), 2.33(2H, t, J=7.5Hz), 2.63(2H, t, J=7.5Hz), 3.60(1H, d, J=7Hz), 3.67(3H, s), 7.12(2H, d, J=8Hz), 7.20(2H, d, J=8Hz) |
| 242 | Methyl 4-[4-(1-Amino-3-methylbutyl)phenyl]-butyrate colorless oil | 3380, 3315, 1738 | 0.90(3H, d, J=6Hz), 0.92(3H, d, J=6Hz), 1.46–1.59(3H, m), 1.51(2H, s), 1.95(2H, qn, J=7.5Hz), 2.34(2H, t, J=7.5Hz), 2.63(2H, t, J=7.5Hz), 3.66(3H, s), 3.92(1H, t, J=7Hz), 7.13(2H, d, J=8Hz), 7.22(2H, d, J=8Hz) |
| 243 | Methyl 4-[4-(1-Amino-4-methylpentyl)phenyl]-butyrate colorless oil | 3384, 3315, 1738 | 0.85(3H, d, J=7Hz), 0.86(3H, d, J=7Hz), 1.04–1.11(1H, m), 1.20–1.27(1H, m), 1.48–1.56(1H, m), 1.54(2H, s), 1.60–1.68(2H, m), 1.95(2H, qn, J=7.5Hz), 2.33(2H, t, J=7.5Hz), 2.63(2H, t, J=7.5Hz), 3.67(3H, s), 3.81(1H, t, J=7Hz), 7.13(2H, d, J=8Hz), 7.22(2H, d, J=8Hz) |
| 244 | Methyl 4-(4-(1-Amino-3,3-dimethylbutyl)phenyl]-butyrate colorless oil | 3384, 3320, 1738 | 0.90(9H, s), 1.25(2H, brs), 1.60(1H, dd, J=14, 6Hz), 1.69(1H, dd, J=14, 6Hz), 1.94(2H, qn, J=7.5Hz), 2.32(2H, t, J=7.5Hz), 2.63(2H, t, J=7.5Hz), 3.67 (3H, s), 3.99(1H, t, J=6Hz), 7.12(2H, d, J=8Hz), 7.23(2H, d, J=8Hz) |
| 245 | Methyl 4-[4-(Aminocyclopentylmethyl)phenyl]-butyrate pale brown oil | 3384, 3320, 1738 | 1.03–1.11(1H, m), 1.30–1.40(2H, m), 1.40–1.50(1H, m), 1.50–1.61(2H, m), 1.61–1.71(1H, m), 1.90–1.96(1H, m), 1.95(2H, qn, J=7.5Hz), 2.07(1H, m), 2.33 (2H, t, J=7.5Hz), 2.63(2H, t, J=7.5Hz), 3.60(1H, d, J=9Hz), 3.66(3H, s), 7.12(2H, d, J=8.5Hz), 7.23(2H, d, J=8.5Hz) |

TABLE 49

| Reference Example No. | Compound Appearance | IR ν (liq) cm$^{-1}$ | NMR δ (CDCl$_3$) |
|---|---|---|---|
| 246 | Methyl 4-[4-(Aminocyclohexylmethyl)phenyl]-butyrate pale yellow oil | 3384, 3320, 1738 | 0.80–0.90(1H, m), 0.94–1.28(4H, m), 1.33–1.43(1H, m), 1.45–1.55(1H, m), 1.55–1.68(2H, m), 1.68–1.80(1H, m), 1.92–1.98(1H, m), 1.95(2H, qn, J=7.5Hz), 2.10(2H, brs), 2.33(2H, t, J=7.5Hz), 2.63(2H, t, J=7.5Hz), 3.59(1H, d, J=8Hz), 3.67(3H, s), 7.12(2H, d, J=8Hz), 7.18(2H, d, J=8Hz) |
| 247 | Methyl 4-[4-(Aminocycloheptylmethyl)phenyl]-butyrate pale brown oil | 3388, 3320, 1738 | 1.10–1.21(1H, m), 1.24–1.76(13H, m), 1.78–1.88(1H, m), 1.95(2H, qn, J=7.5Hz), 2.33(2H, t, J=7.5Hz), 2.63(2H, t, J=7.5Hz), 3.67(3H, s), 3.71(1H, d, J=7Hz), 7.12(2H, d, J=8Hz), 7.20(2H, d, J=8Hz) |
| 248 | Methyl 4-[4-(1-Amino-2-cyclopentylethyl)phenyl]-butyrate colorless oil | 3383, 3315, 1738 | 1.02–1.18(2H, m), 1.42–1.52(2H, m), 1.50(2H, s), 1.53–1.62(2H, m), 1.63–1.72(4H, m), 1.73–1.82(1H, m), 1.95 (2H, qn, J=7.5Hz), 2.33(2H, t, J=7.5Hz), 2.63(2H, t, J=7.5Hz), 3.67(3H, s), 3.87(1H, t, J=7Hz), 7.13(2H, d, J=8Hz), 7.22(2H, d, J=8Hz) |
| 249 | Methyl 4-[4-(1-Amino-2-cyclohexylethyl)phenyl]-butyrate colorless oil | 3384, 3315, 1738 | 0.87–0.96(2H, m), 1.10–1.30(4H, m), 1.46(2H, brs), 1.47–1.58(2H, m), 1.61–1.75(5H, m), 1.95(2H, qn, J=7.5Hz), 2.33(2H, t, J=7.5Hz), 2.63(2H, t, J=7.5Hz), 3.67(3H, s), 3.96(1H, t, J=7.5Hz), 7.13(2H, d, J=8Hz), 7.21(2H, d, J=8Hz) |

TABLE 49-continued

| Reference Example No. | Compound Appearance | IR ν (liq) cm⁻¹ | NMR δ (CDCl₃) |
|---|---|---|---|
| 250 | Methyl 4-[4-(1-Amino-3-cyclohexylpropyl)phenyl]-butyrate<br>pale brown oil | 3372, 3320, 1740 | 0.78–0.90(2H, m), 1.02–1.29(6H, m), 1.50(2H, brs), 1.57–1.71(7H, m), 1.95 (2H, qn, J=7.5Hz), 2.33(2H, t, J=7.5Hz), 2.63(2H, t, J=7.5Hz), 3.67(3H, s), 3.80(1H, t, J=7Hz), 7.13(2H, d, J=8Hz), 7.21(2H, d, J=8Hz) |
| 251 | Methyl 4-[4-(1-Amino-4-cyclohexylbutyl)phenyl]-butyrate<br>pale brown oil | 3384, 3310, 1740 | 0.78–0.88(2H, m), 1.07–1.23(7H, m), 1.28–1.39(1H, m), 1.55–1.70(7H, m), 1.57(2H, brs), 1.95(2H, qn, J=7.5Hz), 2.33(2H, t, J=7.5Hz), 2.63(2H, t, J=7.5Hz), 3.67(3H, s), 3.84(1H, t, J=7Hz), 7.13(2H, d, J=8Hz), 7.22(2H, d, J=8Hz) |

TABLE 50

| Reference Example No. | Compound Appearance | IR ν (liq) cm⁻¹ | NMR δ (CDCl₃) |
|---|---|---|---|
| 252 | Methyl 4-[4-(1-Amino-5-cyclohexylpentyl)phenyl]-butyrate<br>pale brown oil | 3384, 3325, 1740 | 0.78–0.87(2H, m), 1.08–1.21(6H, m), 1.22–1.39(4H, m), 1.59–1.68(7H, m), 1.63(2H, brs), 1.95(2H, qn, J=7.5Hz), 2.33(2H, t, J=7.5Hz), 2.63(2H, t, J=7.5Hz), 3.66(3H, s), 3.84(1H, t, J=7Hz), 7.13(2H, d, J=8Hz), 7.22(2H, d, J=8Hz) |
| 253 | Methyl 4-[4-(1-Amino-6-cyclohexylhexyl)phenyl]-butyrate<br>colorless oil | 3384, 1740 | 0.77–0.90(2H, m), 1.05–1.40(12H, m), 1.47(2H, brs), 1.58–1.72(7H, m), 1.95 (2H, qn, J=7.5Hz), 2.33(2H, t, J=7.5Hz), 2.63(2H, t, J=7.5Hz), 3.66(3H, s), 3.83(1H, t, J=7Hz), 7.13(2H, d, J=8Hz), 7.21(2H, d, J=8Hz) |
| 254 | Methyl trans-4-[4-[Amino(4-methylcyclohexyl)-methyl]phenyl]butyrate<br>pale yellow viscous oil | 3384, 3310, 1738 | 0.76–1.05(4H, m), 0.84(3H, d, J=6.5Hz), 1.20–1.64(6H, m), 1.70–1.76(1H, m), 1.90–1.99(3H, m), 2.33(2H, t, J=7.5Hz), 2.63(2H, t, J=7.5Hz), 3.55(1H, d, J=7.5Hz), 3.67(3H, s), 7.12(2H, d, J=8Hz), 7.18(2H, d, J=8Hz) |
| 255 | Methyl trans-4-[4-[Amino(4-pentylcyclohexyl)-methyl]phenyl]butyrate<br>colorless viscous oil<br>Hydrochloride<br>colorless needles (AcOEt)<br>mp 212–212.5° C. | 3388, 3320, 1742 | 0.72–1.54(17H, m), 0.86(3H, t, J=7Hz), 1.62–1.70(1H, m), 1.74–1.84(1H, m), 1.93–2.00(1H, m), 1.95(2H, qn, J=7.5Hz), 2.33(2H, t, J=7.5Hz), 2.63(2H, t, J=7.5Hz), 3.55(1H, d, J=7.5Hz), 3.67 (3H, s), 7.11(2H, d, J=8Hz), 7.18 (2H, d, J=8Hz) |
| 256 | Methyl 4-[4-[2-(1-Adamantyl)-1-aminoethyl]-phenyl]butyrate<br>colorless oil | 3384, 3320, 1740 | 1.44–1.69(15H, m), 1.92–1.97(4H, m), 2.31(2H, t, J=7.5Hz), 2.61(2H, t, J=7.5Hz), 3.69(3H, s), 4.04(1H, t, J=6Hz), 7.11(2H, d, J=8Hz), 7.22(2H, d, J=8Hz) |
| 257 | Methyl 4-[4-[1-Amino-2-(2-norbornyl)ethyl]phenyl]-butyrate<br>pale brown oil | 3384, 3320, 1738 | 1.01–1.12(4H, m), 1.26–1.71(7H, m), 2.16–2.19(2H, m), 1.95(2H, qn, J=7.5Hz), 2.33(2H, t, J=7.5Hz), 2.63(2H, t, J=7.5Hz), 3.67(3H, s), 3.84–3.89(1H, m), 7.13(2H, d, J=8Hz), 7.22(2H, d, J=8Hz) |

TABLE 51

| Reference Example No. | Compound Appearance | IR ν (liq) cm⁻¹ | NMR δ (CDCl₃) |
|---|---|---|---|
| 258 | Methyl 4-[4-(1-Amino-3-phenylpropyl)phenyl]- | 3380, 3300, | 1.66(2H, brs), 1.93–2.05(2H, m), 1.96 (2H, qn, J=7.5Hz), 2.33(2H, t, J=7.5Hz), |

TABLE 51-continued

| Reference Example No. | Compound Appearance | IR ν (liq) cm$^{-1}$ | NMR δ (CDCl$_3$) |
|---|---|---|---|
| | butyrate colorless oil | 1738 | 2.53–2.69(2H, m), 2.64(2H, t, J=7.5Hz), 3.67(3H, s), 3.88(1H, t, J=6.5Hz), 7.13–7.19(5H, m), 7.22–7.28(4H, m) |
| 259 | Methyl 5-[4-(1-Amino-pentyl)phenyl]valerate colorless oil | 3384, 3330, 1738 | 0.87(3H, t, J=7Hz), 1.13–1.24(1H, m), 1.25–1.36(3H, m), 1.61(2H, brs)1.60–1.73(6H, m), 2.33(2H, t, J=7.5Hz) 2.61(2H, t, J=7.5Hz), 3.66(3H, s), 3.83 (1H, t, J=6.5Hz), 7.13(2H, d, J=8Hz), 7.21(2H, d, J=8Hz) |
| 260 | Methyl 5-[4-(1-Aminohexyl)-phenyl]valerate colorless oil | 3384, 3320, 1738 | 0.86(3H, t, J=7Hz), 1.15–1.38(6H, m) 1.57(2H, brs), 1.58–1.70(6H, m), 2.33 (2H, t, J=7Hz), 2.61(2H, t, J=7.5Hz), 3.66(3H, s), 3.83(1H, t, J=7Hz), 7.12 (2H, d, J=8Hz), 7.21(2H, d, J=Hz) |
| 261 | Methyl 5-[4-(1-Amino-2-cyclohexylethyl)phenyl]-valerate colorless oil | 3384, 3310, 1738 | 0.85–0.99(2H, m), 1.08–1.32(4H, m), 1.42–1.80(13H, m), 2.33(2H, t, J=7Hz), 2.61(2H, t, J=7.5Hz), 3.66(3H, s), 3.96(1H, t, J=7.5Hz), 7.12(2H, d, J=8 Hz), 7.20(2H, d, J=8Hz) |
| 262 | Methyl 4-[4-(1-Amino-heptyl)phenyl]butyrate pale brown oil | 3380, 3304, 1738 | 0.86(3H, t, J=7Hz), 1.16–1.37(8H, m) 1.55(2H, brs), 1.57–1.70(2H, m), 1.95 (2H, qn, J=7.5Hz), 2.33(2H, t, J=7.5Hz), 2.63(2H, t, J=7.5Hz), 3.67(3H, s), 3.83(1H, t, J=7Hz), 7.13(2H, d, J=8Hz), 7.21(2H, d, J=8Hz) |
| 263 | Methyl 4-(4-(1-Aminooctyl)-phenyl]butyrate pale brown oil | 3380, 3320, 1738 | 0.86(3H, t, J=7Hz), 1.14–1.37(10H, m), 1.52(2H, brs), 1.58–1.69(2H, m), 1.95 (2H, qn, J=7.5Hz), 2.33(2H, t, J=7,5Hz), 2.63(2H, t, J=7.5Hz), 3.67(3H, S), 3.84(1H, t, J=7Hz), 7.13(2H, d, J=8Hz), 7.22(2H, d, J=8Hz) |
| 264 | Methyl 4-[4-(1-Aminononyl)-phenyl]butyrate pale yellow oil | 3390, 3320, 1740 | 0.87(3H, t, J=7Hz), 1.14–1.37(12H, m), 1.57–1.71(2H, m), 1.65(2H, brs), 1.95 (2H, qn, J=7.5Hz), 2.33(2H, t, J=7.5Hz), 2.63(2H, t, J, 7.5Hz), 3.67(3H S), 3.84(1H, t, J=7Hz), 7.13(2H, d, J=Hz), 7.22(2H, d, J=8Hz) |

TABLE 52

| Reference Example No. | Compound Appearance | IR ν (liq) cm$^{-1}$ | NMR δ (CDCl$_3$) |
|---|---|---|---|
| 265 | Methyl 4-[4-(1-Amino-5-methylhexyl)phenyl]-butyrate pale brown oil | 3376, 3310, 1738 | 0.83(3H, d, J=7Hz), 0.84(3H, d, J=7Hz), 1.13–1.23(3H, m), 1.28–1.38(1H, m), 1.45–1.55(1H, m), 1.57–1.66(2H, m), 1.61(2H, brs), 1.95(2H, qn, J=7.5Hz), 2.33(2H, t, J=7.5Hz), 2.63(2H, t, J=7.5Hz), 3.66(3H, s), 3.84(1H, t, J=7Hz), 7.13(2H, d, J=8Hz), 7.22(2H, d, J=8Hz) |
| 266 | Methyl 4-[4-(1-Amino-6-methylheptyl)phenyl]-butyrate pale brown oil | 3384, 3320, 1740 | 0.84(6H, d, J=6Hz), 1.09–1.36(6H, m), 1.44–1.55(1H, m), 1.59(2H, brs),1.60–1.66(2H, m), 1.95(2H, qn, J=7.5Hz), 2.33(2H, t, J=7.5Hz), 2.63(2H, t, J=7.5Hz), 3.67(3H, s), 3.84(1H, t, J=7Hz), 7.13(2H, d, J=8Hz), 7.22(2H, d, J=8Hz) |
| 267 | Methyl 4-(4-(1-Amino-4,4-dimethylpentyl)phenyl]-butyrate pale brown oil | 3384, 3320, 1738 | 0.85(9H, s), 0.99–1.08(1H, m), 1.23–1.32(1H, m), 1.52(2H, brs), 1.57–1.64 (2H, m), 1.96(2H, qn, J=7.5Hz), 2.33 (2H, t, J=7.5Hz), 2.64(2H, t, J=7.5Hz), 3.67(3H, s), 3.77(1H, t, J=7Hz), 7.14 (2H, d, J=8Hz), 7.22(2H, d, J=8Hz) |
| 268 | Methyl 4-(4-(1-Amino-5,5-dimethylhexyl)phenyl]-butyrate pale brown oil | 3384, 3330, 1738 | 0.84(9H, s), 1.12–1.24(3H, m), 1.24–1.37(1H, m), 1.58–1.67(2H, m), 1.60 (2H, brs), 1.95(2H, qn, J=7.5Hz), 2.33 (2H, t, J=7.5Hz), 2.63(2H, t, J=7.5Hz), 3.66(3H, s), 3.86(1H, t, J=7Hz), 7.13 (2H, d, J=8Hz), 7.22(2H, d, J=8Hz) |

TABLE 52-continued

| Reference Example No. | Compound Appearance | IR ν (liq) cm⁻¹ | NMR δ (CDCl₃) |
|---|---|---|---|
| 269 | Methyl 4-[4-(1-Amino-6,6-dimethylheptyl)phenyl]-butyrate<br>pale brown oil | 3380, 3320, 1740 | 0.84(9H, s), 1.10–1.35(6H, m), 1.61 (2H, brs), 1.60–1.71(2H, m), 1.95(2H, qn, J=7.5Hz), 2.33(2H, t, J=7.5Hz), 2.63 (2H, t, J=7.5Hz), 3.67(3H, s), 3.84 (1H, t, J=7Hz), 7.13(2H, d, J=8.5Hz), 7.22(2H, d, J=8.5Hz) |
| 270 | Methyl 4-[4-(-Amino-3-cyclopentyl)phenyl]-butyrate<br>pale yellowish brown oil | 3384, 1738 | 1.00–1.10(2H, m), 1.15–1.25(1H, m), 1.30–1.40(1H, m), 1.40–1.80(11H, m), 1.95(2H, qn, J=7.5Hz), 2.33(2H, t, J=7.5Hz), 2.63(2H, t, J=7.5Hz), 3.67 (3H, s), 3.82(1H, t, J=7.5Hz), 7.13(2H, d, J=Hz), 7.22(2H, , d, J=8Hz) |

TABLE 53

| Reference Example No. | Compound Appearance | IR ν (liq) cm⁻¹ | NMR δ (CDCl₃) |
|---|---|---|---|
| 271 | Methyl 4-[4-[1-Amino-3-(4-butoxyphenyl)propyl]-phenyl]butyrate<br>pale brown oil | 3390, 3330, 1738 | 0.97(3H, t, J=7.5Hz), 1.48(2H, sex, J=7.5Hz), 1.54(2H, brs), 1.71–1.78(2H, m), 1.90–2.00(2H, m), 1.95(2H, qn, J=7.5Hz), 2.33(2H, t, J=7.5Hz), 2.45–2.61(2H, m), 2.64(2H, t, J=7.5Hz), 3.67 (3H, s), 3.86(1H, t, J=7Hz), 3.93 (2H, t, J=7Hz), 6.80(2H, d, J=8.5Hz), 7.05 (2H, d, J=8.5Hz), 7.14(2H, d, J=8.5Hz), 5Hz), 7.23(2H, d, J=8.5Hz) |
| 272 | Methyl 4-[4-(1-Amino-4-phenylbutyl)phenyl]-butyrate<br>pale yellow oil | 3380, 3300, 1738 | 1.44–1.74(6H, m), 1.95(2H, qn, J=7.5Hz), 2.33(2H, t, J=7.5Hz), 2.57–2.65 (4H, m), 3.66(3H, s), 3.86(1H, t, J=7Hz), 7.10–7.27(9H, m) |
| 273 | Methyl 4-[4-(1-Amino-5-phenylpentyl)phenyl]-butyrate<br>pale yellow oil | 3384, 3320, 1738 | 1.20–1.31(1H, m), 1.34–1.72(7H, m), 1.95(2H, qn, J=7.5Hz), 2.33(2H, t, J=7.5Hz), 2.57(2H, t, J=7.5Hz), 2.63(2 H, t, J=7.5Hz), 3.67(3H, s), 3.84(1H, t, J=7.5Hz), 7.11–7.28(9H, m) |
| 274 | Methyl 4-[4-(1-Amino-6-phenylhexyl)phenyl]-butyrate<br>colorless oil | 3380, 3320, 1738 | 1.18–1.68(10H, m), 1.95(2H, qn, J=7.5Hz), 2.33(2H, t, J=7.5Hz), 2.57(2H, t, J=7.5Hz), 2.63(2H, t, J=7.5Hz), 3.66 (3H, s), 3.82(1H, t, J=7.5Hz), 7.11–7.18(3H, m), 7.13(2H, d, J=8Hz), 7.20 (2H, d, J=8Hz), 7.23–7.28(2H, m) |
| 275 | Methyl 4-[4-(1-Amino-3-(4-butylphenyl)propyl]phenyl]-butyrate<br>pale brown oil | 3380, 3310, 1738 | 0.91(3H, t, J=7.5Hz), 1.34(2H, sex, J=7.5Hz), 1.50–1.61(2H, m), 1.53(2H brs), 1.92–2.01(4H, m), 2.33(2H, t, J=7.5Hz), 2.49–2.64(2H, m), 2.56(2H t, J=8Hz), 2.64(2H, t, J=7.5Hz), 3.66 (3H, s), 3.87(1H, t, J=7Hz), 7.06–7.10 (4H, m), 7.14(2H, d, J=8Hz), 7.23(2 H, d, J=8Hz) |
| 276 | Methyl 4-[4-(1-Amino-3-(p-tolyl)propyl]phenyl]-butyrate<br>pale brown oil | 3384, 3320, 1738 | 1.53(2H, brs), 1.90–2.00(2H, m), 1.96 (2H, qn, J=7.5Hz), 2.31(3H, s), 2.33 (2H, t, J=7.5Hz), 2.47–2.65(2H, m), 2.64 (2H, t, J=7.5Hz), 3.67(3H, s), 3.87 (1H, t, J=7Hz), 7.04(2H, d, J=8Hz), 7.07 (2H, d, J=8Hz), 7.14(2H, d, J=8Hz), 7.23(2H, d, J=8Hz) |

TABLE 54

| Reference Example No. | Compound Appearance | IR ν (liq) cm⁻¹ | NMR δ (CDCl₃) |
|---|---|---|---|
| 277 | Methyl 4-[4-[1-Amino-3-(4-fluorophenyl)propyl]- | 3384, 3300, | 1.60(2H, brs), 1.90–2.02(2H, m), 1.96 (2H, qn, J=7.5Hz), 2.33(2H, t, J=7.5Hz, |

TABLE 54-continued

| Reference Example No. | Compound Appearance | IR ν (liq) cm$^{-1}$ | NMR δ (CDCl$_3$) |
|---|---|---|---|
| | phenyl]butyrate colorless oil | 1738 | 2.49–2.66(2H, m), 2.64(2H, t, J=7.5Hz), 3.67(3H, s), 3.86(1H, t, J=7Hz, 6.94(2H, t, J=8.5Hz), 7.09(2H, dd, J=8.5, 5.5Hz), 7.15(2H, d, J=8Hz), 7.22 (2H, d, J=8Hz) |
| 278 | Methyl 4-[4-[1-Amino-3-(3-fluorophenyl)propyl]-phenyl]butyrate pale yellow oil | 3384, 3320, 1738 | 1.55(2H, brs), 1.92–2.01(4H, m), 2.34 (2H, t, J=7.5Hz), 2.52–2.63(2H, m), 2.64(2H, t, J=7.5Hz), 3.67(3H, s), 3.87 (1H, t, J=7.5Hz), 6.83–6.96(3H, m), 7.15(2H, d, J=8Hz), 7.18–7.24(1H, m), 7.23(2H, d, J=8Hz) |
| 279 | Methyl 4-[4-[1-Amino-3-(4-chlorophenyl)propyl]-phenyl]butyrate pale brown oil | 3380 3316 1738 | 1.55(2H, brs), 1.88–2.03(2H, m), 1.96 (2H, qn, J=7.5Hz), 2.33(2H, t, J=7.5Hz, 2.48–2.63(2H, m), 2.64(2H, t, J=7.5Hz), 3.67(3H, s), 3.85(1H, t, J=7Hz), 7.07(2H, d, J=8.5Hz), 7.22(2H, d, J=8Hz), 7.22(2H, d, J=8.5Hz) |

Example 1

Methyl 4-[4-[1-(4-Chlorophenylsulfonylamino)-2-phenylethyl]phenyl]butyrate

To a solution of 2.16 g of methyl 4-[4-(1-amino-2-phenylethyl)phenyl]butyrate and 1.11 ml of triethylamine in 10 ml of methylene chloride, a solution of 1.53 g of 4-chlorobenzenesulfonyl chloride in 10 ml of methylene chloride was added dropwise under ice-cooling.

The reaction mixture was stirred at room temperature for 1.5 hours, and then washed with dilute hydrochloric acid and water successively. The methylene chloride layer was dried and then the solvent was removed under reduced pressure. The residue was purified by column chromatography on silica gel (methylene chloride→methylene chloride:ethyl acetate=5:1) to yield 2.44 g of colorless crystals. Recrystallization from a mixture of isopropyl ether and ethyl acetate gave colorless prisms, mp 93.5°–94° C.

Analysis for C$_{25}$H$_{26}$ClNO$_4$S

Calculated C, 63.62; H, 5.55; N, 2.97 Found C, 63.58; H, 5.60; N, 2.94

The compounds of Examples 2 through 61 were prepared in the same manner as described in Example 1.

Example 2

Methyl 4-[4-[1-(4-Chlorophenylsulfonylamino)ethyl]phenyl]butyrate

Appearance colorless prisms (AcOEt-i-Pr$_2$O)

mp 92°–93° C.

Analysis for C$_{19}$H$_{22}$ClNO$_4$S

Calculated C, 57.64; H, 5.60; N, 3.54 Found C, 57.79; H, 5.57; N, 3.46

Example 3

Methyl 4-[4-[1-(4-Chlorophenylsulfonylamino)propyl]phenyl]butyrate

Appearance colorless columns (i-Pr$_2$O)

mp 76° C.

Analysis for C$_{20}$H$_{24}$ClNO$_4$S

Calculated C, 58.60; H, 5.90; N, 3.42 Found C, 58.54; H, 5.83; N, 3.42

Example 4

Methyl 4-[4-[1-(4-Chlorophenylsulfonylamino)butyl]phenyl]butyrate

Appearance colorless needles (i-Pr$_2$O)

mp 66.5°–67.5° C.

Analysis for C$_{21}$H$_{26}$ClNO$_4$S

Calculated C, 59.49; H, 6.18; N, 3.30 Found C, 59.50; H, 6.45; N, 3.44

Example 5

Methyl 4-[4-[1-(4-Chlorophenylsulfonylamino)pentyl]phenyl]butyrate

Appearance colorless needles (i-Pr$_2$O)

mp 65°–66.5° C.

Analysis for C$_{22}$H$_{28}$ClNO$_4$S

Calculated C, 60.33; H, 6.44; N, 3.20 Found C, 60.12; H, 6.65; N, 3.18

Example 6

Methyl 4-[4-[1-(4-Chlorophenylsulfonylamino)hexyl]phenyl]butyrate

Appearance colorless prisms (i-Pr$_2$O)

mp 79°–80° C.

Analysis for C$_{23}$H$_{30}$ClNO$_4$S

Calculated C, 61.12; H, 6.69; N, 3.10 Found C, 60.92; H, 6.94; N, 3.05

Example 7

Methyl 4-[4-[1-(4-Chlorophenylsulfonylamino) decyl]phenyl]butyrate

Appearance colorless plates (i-Pr$_2$O)
mp 68.5°~69° C.
Analysis for C$_{27}$H$_{38}$ClNO$_4$S
Calculated C, 63.82; H, 7.54; N, 2.76 Found C, 63.54; H, 7.76; N, 2.78

Example 8

Methyl 4-[4-[1-(4-Chlorophenylsulfonylamino)-2-methylpropyl]phenyl]butyrate

Appearance colorless prisms (i-Pr$_2$O)
mp 96°~96.5° C.
Analysis for C$_{21}$H$_{26}$ClNO$_4$S
Calculated C, 59.49; H, 6.18; N, 3.30 Found C, 59.57; H, 6.25; N, 3.41

Example 9

Methyl 4-[4-[1-(4-Chlorophenylsulfonylamino)-3-methylbutyl]phenyl]butyrate

Appearance colorless needles (i-Pr$_2$O—AcOEt)
mp 82°~83° C.
Analysis for C$_{22}$H$_{28}$ClNO$_4$S
Calculated C, 60.33; H, 6.44; N, 3.20 Found C, 60.28; H, 6.64; N, 3.22

Example 10

Methyl 4-[4-[1-(4-Chlorophenylsulfonylamino)-4-methylpentyl]phenyl]butyrate

Appearance colorless plates (i-Pr$_2$O—AcOEt)
mp 89°~90.5° C.
Analysis for C$_{23}$H$_{30}$ClNO$_4$S
Calculated C, 61.12; H, 6.69; N, 3.10 Found C, 61.04; H, 6.85; N, 3.06

Example 11

Methyl 4-[4-[1-(4-Chlorophenylsulfonylamino)-3,3-dimethylbutyl]phenyl]butyrate

Appearance colorless prisms (i-Pr$_2$O)
mp 62.5°~64° C.
Analysis for C$_{23}$H$_{30}$ClNO$_4$S
Calculated C, 61.12; H, 6.69; N, 3.10 Found C, 60.94; H, 6.84; N, 3.01

Example 12

Methyl 4-[4-[(4-Chlorophenylsulfonylamino) cyclopentylmethyl]phenyl]butyrate

Appearance colorless needles (i-Pr$_2$O)
mp 84° C.
Analysis for C$_{23}$H$_{28}$ClNO$_4$S
Calculated C, 61.39; H, 6.27; N, 3.11 Found C, 61.30; H, 6.19; N, 3.11

Example 13

Methyl 4-[4-[(4-Chlorophenylsulfonylamino) cyclohexylmethyl]phenyl]butyrate

Appearance colorless needles (i-PrOH)
mp 97.5°~98° C.
Analysis for C$_{24}$H$_{30}$ClNO$_4$S
Calculated C, 62.12; H, 6.52; N, 3.02 Found C, 61.90; H, 6.47; N, 3.00

Example 14

Methyl 4-[4-[(4-Chlorophenylsulfonylamino) cycloheptylmethyl]phenyl]butyrate

Appearance colorless needles (i-Pr$_2$O)
mp 102°~103.5° C.
Analysis for C$_{25}$H$_{32}$ClNO$_4$S
Calculated C, 62.81; H, 6.75; N, 2.93 Found C, 62.68; H, 6.93; N, 2.88

Example 15

Methyl trans-4-[4-[(4-Chlorophenylsulfonylamino) (4-methylcyclohexyl)methyl]phenyl]butyrate Appearance colorless needles (EtOH)
mp 132°~133° C.
Analysis for C$_{25}$H$_{32}$ClNO$_4$S
Calculated C, 62.81; H, 6.75; N, 2.93 Found C, 62.54; H, 7.02; N, 3.11

Example 16

Methyl trans-4-[4-[(4-Chlorophenylsulfonylamino) (4-pentylcyclohexyl)methyl]phenyl]butyrate Appearance colorless needles (EtOH)
mp 115°~116° C.
Analysis for C$_{29}$H$_{40}$ClNO$_4$S
Calculated C, 65.21; H, 7.55; N, 2.62 Found C, 64.96; H, 7.81; N, 2.71

Example 17

Methyl 4-[4-[1-(4-Chlorophenylsulfonylamino)-2-cyclopentylethyl]phenyl]butyrate

Appearance colorless prisms (i-Pr$_2$O—AcOEt)
mp 102.5°~104° C.
Analysis for C$_{24}$H$_{30}$ClNO$_4$S
Calculated C, 62.12; H, 6.52; N, 3.02 Found C, 62.04; H, 6.70; N, 3.02

Example 18

Methyl 4-[4-[1-(4-Chlorophenylsulfonylamino)-2-cyclohexylethyl]phenyl]butyrate

Appearance colorless prisms (i-Pr$_2$O—AcOEt)
mp 115°~116° C.
Analysis for C$_{25}$H$_{32}$ClNO$_4$S
Calculated C, 62.81; H, 6.75; N, 2.93 Found C, 62.56; H, 6.92; N, 2.89

Example 19

Methyl 4-[4-[1-(4-Chlorophenylsulfonylamino)-3-cyclohexylpropyl]phenyl]butyrate

Appearance colorless prisms (AcOEt-i-P$_2$O)
mp 104°~105° C.
Analysis for C$_{26}$H$_{34}$ClNO$_4$S
Calculated C, 63.46; H, 6.96; N, 2.85 Found C, 63.46; H, 7.21; N, 2.82

Example 20

Methyl 4-[4-[1-(4-Chlorophenylsulfonylamino)-4-cyclohexylbutyl]phenyl]butyrate

Appearance colorless needles (i-Pr$_2$O)
mp 81°~82° C.
Analysis for C$_{27}$H$_{36}$ClNO$_4$S
Calculated C, 64.08; H, 7.17; N, 2.77 Found C, 64.11; H, 7.43; N, 2.72

Example 21

Methyl 4-[4-[1-(4-Chlorophenylsulfonylamino)-5-cyclohexylpentyl]phenyl]butyrate

Appearance colorless plates (i-Pr$_2$O)
mp 87.5°~89.5° C.
Analysis for C$_{28}$H$_{38}$ClNO$_4$S
Calculated C, 64.66; H, 7.36; N, 2.69 Found C, 64.42; H, 7.64; N, 2.68

Example 22

Methyl 4-[4-[1-(4-Chlorophenylsulfonylamino)-6-cyclohexylhexyl]phenyl]butyrate

Appearance colorless prisms (i-Pr$_2$O)
mp 82°~83.5° C.
Analysis for C$_{29}$H$_{40}$ClNO$_4$S
Calculated C, 65.21; H, 7.55; N, 2.62 Found C, 65.10; H, 7.75; N, 2.57

Example 23

Methyl 4-[4-[2-(1-Adamantyl)-1-(4-chlorophenylsulfonylamino)ethyl]phenyl]butyrate Appearance colorless prisms (AcOEt-i-Pr$_2$O)
mp 127.5°~128° C.
Analysis for C$_{29}$H$_{36}$ClNO$_4$S
Calculated C, 65.70; H, 6.84; N, 2.64 Found C, 65.54; H, 7.01; N, 2.68

Example 24

Methyl 4-[4-[1-(4-Chlorophenylsulfonylamino)-2-(2-norbornyl)ethyl]phenyl]butyrate Appearance colorless needles (AcOEt-i-Pr$_2$O)
mp 112.5°~113.5° C.
Analysis for C$_{26}$H$_{33}$ClNO$_4$S
Calculated C, 63.59; H, 6.77; N, 2.85 Found C, 63.52; H, 6.63; N, 2.76

Example 25

Methyl 3-[4-[1-(4-Chlorophenylsulfonylamino)-2-phenylethyl]phenyl]propionate

Appearance colorless plates (AcOEt-i-Pr$_2$O)
mp 114°~115° C.
Analysis for C$_{24}$H$_{24}$ClNO$_4$S
Calculated C, 62.94; H, 5.28; N, 3.06 Found C, 63.02; H, 5.50; N, 3.01

Example 26

Methyl 4-[4-[2-Phenyl-1-(phenylsulfonylamino)ethyl]phenyl]butyrate

Appearance colorless plates (AcOEt-i-Pr$_2$O)
mp 93°~94.5° C.
Analysis for C$_{25}$H$_{27}$NO$_4$S
Calculated C, 68.62; H, 6.22; N, 3.20 Found C, 68.42; H, 6.08; N, 3.16

Example 27

Methyl 4-[4-[1-(4-Fluorophenylsulfonylamino)-2-phenylethyl]phenyl]butyrate

Appearance colorless prisms (AcOEt-i-Pr$_2$O)
mp 108.5°~110° C.
Analysis for C$_{25}$H$_{26}$FNO$_4$S
Calculated C, 65.91; H, 5.75; N, 3.07 Found C, 65.71; H, 5.80; N, 3.01

Example 28

Methyl 4-[4-[1-(4-Bromophenylsulfonylamino)-2-phenylethyl]phenyl]butyrate

Appearance colorless prisms (AcOEt-i-Pr$_2$O)
mp 101°~102° C.
Analysis for C$_{25}$H$_{26}$BrNO$_4$S
Calculated C, 58.14; H, 5.07; N, 2.71 Found C, 58.09; H, 5.04; N, 2.95

Example 29

Methyl 4-[4-[1-(p-Tolylsulfonylamino)-2-phenylethyl]phenyl]butyrate

Appearance colorless prisms (AcOEt-i-Pr$_2$O)
mp 103.5°~104.5° C.
Analysis for C$_{26}$H$_{29}$NO$_4$S
Calculated C, 69.15; H, 6.47; N, 3.10 Found C, 69.14; H, 6.56; N, 3.03

Example 30

Methyl 4-[4-[1-(4-Methoxysulfonylamino)-2-phenylethyl]phenyl]butyrate

Appearance colorless columns (AcOEt-i-Pr$_2$O)
mp 114.5°~115.5° C.
Analysis for C$_{26}$H$_{29}$NO$_5$S Calculated C, 66.79; H, 6.25; N, 3.00 Found C, 66.74; H, 6.28; N, 2.95

Example 31

Methyl 5-[4-[1-(4-Chlorophenylsulfonylamino)-2-phenylethyl]phenyl]valerate

Appearance colorless prisms (AcOEt-i-Pr$_2$O)
mp 107.5°~109° C.
Analysis for C$_{26}$H$_{28}$ClNO$_4$S
Calculated C, 64.25; H, 5.81; N, 2.88 Found C, 64.25; H, 6.05; N, 2.79

Example 32

Methyl 4-[4-[1-(4-Chlorophenylsulfonylamino)-2-(2-fluorophenyl)ethyl]phenyl]butyrate Appearance colorless prisms (AcOEt-i-Pr$_2$O)
mp 97°~98° C.
Analysis for C$_{25}$H$_{25}$ClFNO$_4$S
Calculated C, 61.28; H, 5.14; N, 2.86 Found C, 61.25; H, 5.11; N, 2.90

Example 33

Methyl 4-[4-[1-(4-Chlorophenylsulfonylamino)-2-(3-fluorophenyl)ethyl]phenyl]butyrate Appearance colorless prisms (AcOEt-i-Pr$_2$O)
mp 88°~90° C.
Analysis for C$_{25}$H$_{25}$ClFNO$_4$S
Calculated C, 61.28; H, 5.14; N, 2.86 Found C, 61.15; H, 5.08; N, 2.83

Example 34

Methyl 4-[4-[1-(4-Chlorophenylsulfonylamino)-2-(4-fluorophenyl)ethyl]phenyl]butyrate Appearance pale brown prisms (AcOEt-i-Pr$_2$O)
mp 104.5°~106° C.
Analysis for C$_{25}$H$_{25}$ClFNO$_4$S
Calculated C, 61.28; H, 5.14; N, 2.86 Found C, 61.24; H, 5.10; N, 2.92

Example 35

Methyl 4-[4-[2-(4-Chlorophenyl)-1-(4-chlorophenylsulfonylamino)ethyl]phenyl]butyrate Appearance colorless needles (AcOEt-i-Pr$_2$O)
mp 108°~109.5° C.
Analysis for C$_{25}$H$_{25}$Cl$_2$NO$_4$S
Calculated C, 59.29; H, 4.98; N, 2.77 Found C, 59.33; H, 4.98; N, 2.80

Example 36

Methyl 4-[4-[1-(4-Chlorophenylsulfonylamino)-2-(p-tolyl)ethyl]phenyl]butyrate

Appearance colorless prisms (AcOEt-i-Pr$_2$O)
mp 109.5°~110.5° C.
Analysis for C$_{26}$H$_{28}$ClNO$_4$S
Calculated C, 64.25; H, 5.81; N, 2.88 Found C, 64.05; H, 5.89; N, 2.90

Example 37

Methyl 4-[4-[1-(4-Chlorophenylsulfonylamino)-3-phenylpropyl]phenyl]butyrate

Appearance colorless needles (AcOEt-i-Pr$_2$O)
mp 112°~114° C.
Analysis for C$_{26}$H$_{28}$ClNO$_4$S
Calculated C, 64.25; H, 5.81; N, 2.88 Found C, 64.19; H, 5.95; N, 2.89

Example 38

Methyl 4-[4-[1-(4-Chlorophenylsulfonylamino)heptyl]phenyl]butyrate

Appearance colorless prisms (i-Pr$_2$O)
mp 86°~88° C.
Analysis for C$_{24}$H$_{32}$ClNO$_4$S
Calculated C, 61.85; H, 6.92; N, 3.01 Found C, 61.69; H, 7.13; N, 3.20

Example 39

Methyl 4-[4-[1-(4-Chlorophenylsulfonylamino)octyl]phenyl]butyrate

Appearance colorless prisms (i-Pr$_2$O)
mp 72°~74.5° C.
Analysis for C$_{25}$H$_{34}$ClNO$_4$S
Calculated C, 62.55; H, 7.14; N, 2.92 Found C, 62.59; H, 7.39; N, 3.11

Example 40

Methyl 4-[4-[1-(4-Chlorophenylsulfonylamino)nonyl]phenyl]butyrate

Appearance colorless flakes (i-Pr$_2$O)
mp 81°~83° C.
Analysis for C$_{26}$H$_{26}$ClNO$_4$S
Calculated C, 63.20; H, 7.34; N, 2.83 Found C, 63.20; H, 7.38; N, 2.82

Example 41

Methyl 5-[4-[1-(4-Chlorophenylsulfonylamino)pentyl]phenyl]valerate

Appearance colorless needles (i-Pr$_2$O)
mp 78.5°~79.5° C.
Analysis for C$_{23}$H$_{30}$ClNO$_4$S
Calculated C, 61.12; H, 6.69; N, 3.10 Found C, 61.04; H, 6.95; N, 2.95

Example 42

Methyl 4-[4-[1-(phenylsulfonylamino)hexyl]phenyl]butyrate

Appearance colorless viscous oil
IR spectrum ν (liq) cm$^{-1}$: 3288, 1738
NMR spectrum δ (CDCl$_3$) ppm: 0.81(3H,t,J=6.5 Hz), 1.04–1.30(6H,m),1.60–1.70(1H,m),1.70–1.80(1H,m), 1.88(2H,qn,J=7.5 Hz),2.28(2H,t,J=7.5 Hz),2.54(2H,t,J=7.5 Hz),3.68(3H,s ),4.27(1H,q,J=7.5 Hz),4.91–4.96(1H,m), 6.90(2H,d,J=8 Hz),6.93(2H,d,J=8 Hz),7.29(2H,t,J=7.5 Hz), 7.41(1H,t,J=7.5 Hz),7.63(2H,d,J=7.5 Hz)

Example 43

Methyl 4-[4-[1-(4-Bromophenylsulfonylamino)hexyl]phenyl]butyrate

Appearance colorless needles (i-Pr$_2$O)
mp 82°~83° C.
Analysis for C$_{23}$H$_{30}$BrNO$_4$S
Calculated C, 55.64; H, 6.09; N, 2.82 Found C, 55.47; H, 6.06; N, 2.80

Example 44

Methyl 4-[4-[1-(4-Fluorophenylsulfonylamino)hexyl]phenyl]butyrate

Appearance colorless viscous oil
IR spectrum ν (liq) cm$^{-1}$: 3288, 1738
NMR spectrum δ (CDCl$_3$) ppm: 0.82(3H,t,J=7 Hz), 1.05–1.33(6H,m),1.60–1.70(1H,m),1.70–1.80(1H,m), 1.88(2H,qn,J=7.5 Hz),2.29(2H,t,J=7.5 Hz),2.55(2H,t,J=7.5 Hz),3.68(3H,s),4.27(1H,q,J=7.5 Hz),4.85(1H,d,J=7.5 Hz), 6.88(2H,d,J=8 Hz),6.94(2H,t,J=8.5 Hz),6.95(2H,d,J=8 Hz), 7.59(2H,dd,J=8.5,5 Hz)

Example 45

Methyl 5-[4-[1-(4-Chlorophenylsulfonylamino)hexyl]phenyl]valerate

Appearance colorless needles (i-Pr$_2$O)
mp 82°~83.5° C.
Analysis for C$_{24}$H$_{32}$ClNO$_4$S
Calculated C, 61.85; H, 6.92; N, 3.01 Found C, 61.66; H, 7.20; N, 2.73

Example 46

Methyl 4-[4-[1-(4-Chlorophenylsulfonylamino)-5-methylhexyl]phenyl]butyrate

Appearance colorless prisms (i-Pr$_2$O)
mp 53°~55° C.
Analysis for C$_{24}$H$_{32}$ClNO$_4$S
Calculated C, 61.85; H, 6.92; N, 3.01 Found C, 61.89; H, 7.02; N, 2.98

Example 47

Methyl 4-[4-[1-(4-Chlorophenylsulfonylamino)-6-methylheptyl]phenyl]butyrate

Appearance colorless prisms (n-Hexane)
mp 61.5°~62.5° C.
Analysis for C$_{25}$H$_{34}$ClNO$_4$S
Calculated C, 62.55; H, 7.14; N, 2.92 Found C, 62.50; H, 7.21; N, 2.92

Example 48

Methyl 4-[4-[1-(4-Chlorophenylsulfonylamino)-4,4-dimethylpentyl]phenyl]butyrate

Appearance colorless prisms (i-Pr$_2$O—AcOEt)
mp 104.5°~106° C.
Analysis for C$_{24}$H$_{32}$ClNO$_4$S
Calculated C, 61.85; H, 6.92; N, 3.01 Found C, 61.71; H, 7.14; N, 3.03

Example 49

Methyl 4-[4-[1-(4-Chlorophenylsulfonylamino)-5,5-dimethylhexyl]phenyl]butyrate

Appearance colorless prisms (i-Pr$_2$O-n-Hexane)
mp 73.5°~74.5° C.
Analysis for C$_{25}$H$_{34}$ClNO$_4$S
Calculated C, 62.55; H, 7.14; N, 2.92 Found C, 62.52; H, 7.18; N, 2.71

Example 50

Methyl 4-[4-[1-(4-Chlorophenylsulfonylamino)-6,6-dimethylheptyl]phenyl]butyrate

Appearance colorless prisms (i-Pr$_2$O-n-Hexane)
mp 67.5°~69° C.
Analysis for C$_{26}$H$_{36}$ClNO$_4$S
Calculated C, 63.20; H, 7.34; N, 2.83 Found C, 63.09; H, 7.35; N, 2.70

Example 51

Methyl 4-[4-[1-(4-Chlorophenylsulfonylamino)-3-cyclopentylpropyl]phenyl]butyrate Appearance colorless needles (MeOH)
mp 104°~105° C.
Analysis for C$_{25}$H$_{32}$ClNO$_4$S
Calculated C, 62.81; H, 6.75; N, 2.93 Found C, 62.64; H, 6.85; N, 2.69

Example 52

Methyl 5-[4-[1-(4-Chlorophenylsulfonylamino)-2-cyclohexylethyl]phenyl]valerate

Appearance colorless crystals (AcOEt-i-Pr$_2$O)
mp 102.5°~104.5° C.
Analysis for C$_{26}$H$_{34}$ClNO$_4$S
Calculated C, 63.46; H, 6.96; N, 2.85 Found C, 63.42; H, 7.01; N, 2.83

Example 53

Methyl 4-[4-[1-(4-Chlorophenylsulfonylamino)-3-phenylbutyl]phenyl]butyrate

Appearance colorless needles (i-Pr$_2$O)

mp 73.5°~74.5° C.

Analysis for C$_{27}$H$_{30}$ClNO$_4$S

Calculated C, 64.85; H, 6.05; N, 2.80 Found C, 64.93; H, 5.99; N, 2.78

Example 54

Methyl 4-[4-[1-(4-Chlorophenylsulfonylamino)-5-phenylpentyl]phenyl]butyrate

Appearance colorless prisms (EtOH)

mp 94°~95.5° C.

Analysis for C$_{28}$H$_{32}$ClNO$_4$S

Calculated C, 65.42; H, 6.27; N, 2.72 Found C, 65.24; H, 6.14; N, 2.75

Example 55

Methyl 4-[4-[1-(4-Chlorophenylsulfonylamino)-6-phenylhexyl]phenyl]butyrate

Appearance colorless prisms (i-Pr$_2$O)

mp 67°~68° C.

Analysis for C$_{29}$H$_{34}$ClNO$_4$S

Calculated C, 65.96; H, 6.49; N, 2.65 Found C, 65.83; H, 6.35; N, 2.69

Example 56

Methyl 4-[4-[3-(4-Butylphenyl)-1-(4-chlorophenylsulfonylamino)propyl]phenyl]butyrate Appearance colorless viscous oil IR spectrum ν (liq) cm$^{-1}$: 3288, 1738

NMR spectrum δ (CDCl$_3$) ppm: 0.92(3H,t,J=7.5 Hz),1.35(2H,sex,J=7.5 Hz),1.54–1.61(2H,m),1.89(2H,qn,J=7.5 Hz),1.94–2.03(1H,m),2.05–2.14(1H,m),2.31(2H,t,J=7.5 Hz),2.44–2.55(2H,m),2.57(4H,t,J=8 Hz),3.68(3H,s),4.28(1H,q,J=7.5 Hz),5.07(1H,d,J=7.5 Hz),6.88(2H,d,J=8 Hz),6.95(2H,d,J=8 Hz),6.97(2H,d,J=8 Hz),7.06(2H,d,J=8 Hz),7.21(2H,d,J=8.5 Hz),7.48(2H,d,J=8.5 Hz)

Example 57

Methyl 4-[4-[3-(4-Butoxyphenyl)-1-(4-chlorophenylsulfonylamino)propyl]phenyl]butyrate Appearance colorless prisms (i-Pr$_2$O)

mp 70.5°~72.5° C.

Analysis for C$_{30}$H$_{36}$ClNO$_5$S

Calculated C, 64.56; H, 6.50; N, 2.51 Found C, 64.61; H, 6.59; N, 2.47

Example 58

Methyl 4-[4-[1-(4-Chlorophenylsulfonylamino)-3-(p-tolyl)propyl]phenyl]butyrate

Appearance colorless prisms (i-Pr$_2$O—AcOEt)

mp 83°~84.5° C.

Analysis for C$_{27}$H$_{30}$ClNO$_4$S

Calculated C, 64.85; H, 6.05; N, 2.80 Found C, 64.87; H, 6.10; N, 2.78

Example 59

Methyl 4-[4-[3-(4-Chlorophenyl)-1-(4-chlorophenylsulfonylamino)propyl]phenyl]butyrate Appearance colorless prisms (i-Pr$_2$O)

mp 71°~72.5° C.

Analysis for C$_{26}$H$_{27}$Cl$_2$NO$_4$S

Calculated C, 60.00; H, 5.23, N, 2.69 Found C, 60.29; H, 5.13; N, 2.79

Example 60

Methyl 4-[4-[1-(4-Chlorophenylsulfonylamino)-3-(4-fluorophenyl)propyl]phenyl]butyrate Appearance colorless oil IR spectrum ν (liq) cm$^{-1}$: 3284, 1738

NMR spectrum δ (CDCl$_3$) ppm: 1.89(2H,qn,J=7.5 Hz),1.93–2.02(1H,m),2.05–1.03(1H,m),2.31(2H,t,J=7.5 Hz),2.47–2.59(2H,m),2.56(2H,t,J=7.5 Hz),3.68(3H,s),4.25(1H,q,J=7.5 Hz),5.00(1H,d,J=7.5 Hz),6.85(2H,d,J=8.5 Hz),6.95(4H,d,J=8.5 Hz),7.03(2H,dd,J=8.5,5.5 Hz),7.22(2H,d,J=8.5 Hz),7.48(2H,d,J=8.5 Hz)

Example 61

Methyl 4-[4-[1-(4-Chlorophenylsulfonylamino)-3-(3-fluorophenyl)propyl]phenyl]butyrate Appearance colorless needles (i-Pr$_2$O—MeOH)

mp 75.5°~76° C.

Analysis for C$_{26}$H$_{27}$ClFNO$_4$S

Calculated C, 61.96; H, 5.40; N, 2.78 Found C, 61.89; H, 5.41; N, 2.77

Example 62

4-[4-[1-(4-Chlorophenylsulfonylamino)-2-phenylethyl]phenyl]butyric Acid

To a suspension of 2.00 g of methyl 4-[4-[1-(4-chlorophenylsulfonylamino)-2-phenylethyl]phenyl]butyrate in 17 ml of methanol, 7.7 ml of 2N aqueous sodium hydroxide was added and stirring was continued at room temperature for 2 hours. The solvent was removed under reduced pressure. The residue was added with water, acidified with dilute hydrochloric acid, and then extracted with methylene chloride. After the methylene chloride layer was washed with water and dried, the solvent was removed under reduced pressure to yield 1.87 g of colorless crystals. Recrystallization from a mixture of isopropyl ether and ethyl acetate gave colorless needles, mp 152°~153° C.

Analysis for C$_{24}$H$_{24}$ClNO$_4$S

Calculated C, 62.94; H, 5.28; N, 3.06 Found C, 62.76; H, 5.43; N, 3.03

The compounds of Examples 63 through 122 were obtained in the same manner as described in Example 62.

Example 63

4-[4-[1-(4-Chlorophenylsulfonylamino)ethyl]phenyl]butyric Acid

Appearance colorless needles (AcOEt-i-$Pr_2O$)
mp 98°~98.5° C.
Analysis for $C_{18}H_{20}ClNO_4S$
Calculated C, 56.61; H, 5.28; N, 3.67 Found C, 56.59; H, 5.24; N, 3.61

Example 64

4-[4-[1-(4-Chlorophenylsulfonylamino)propyl]phenyl]butyric Acid

Appearance colorless columns (AcOEt-i-$Pr_2O$)
mp 120°~121° C.
Analysis for $C_{19}H_{22}ClNO_4S$
Calculated C, 57.64; H, 5.60; N, 3.54 Found C, 57.63; H, 5.63; N, 3.49

Example 65

4-[4-[1-(4-Chlorophenylsulfonylamino)butyl]phenyl]butyric Acid

Appearance colorless needles (90% aq. MeOH)
mp 111.5°~112.5° C.
Analysis for $C_{20}H_{24}ClNO_4S$
Calculated C, 58.60; H, 5.90; N, 3.42 Found C, 58.57; H, 6.09; N, 3.46

Example 66

4-[4-[1-(4-Chlorophenylsulfonylamino)pentyl]phenyl]butyric Acid

Appearance colorless prisms (90% aq. MeOH)
mp 119°~120.5° C.
Analysis for $C_{21}H_{26}ClNO_4S$
Calculated C, 59.49; H, 6.18; N, 3.30 Found C, 59.40; H, 6.31; N, 3.32

Example 67

4-[4-[1-(4-Chlorophenylsulfonylamino)hexyl]phenyl]butyric Acid

Appearance colorless prisms (80% aq. MeOH)
mp 117°~118° C.
Analysis for $C_{22}H_{28}ClNO_4S$
Calculated C, 60.33; H, 6.44; N, 3.20 Found C, 60.26; H, 6.70; N, 3.23

Example 68

4-[4-[1-(4-Chlorophenylsulfonylamino)decyl]phenyl]butyric Acid

Appearance colorless prisms (i-$Pr_2O$)
mp 99.5°~100.5° C.
Analysis for $C_{26}H_{36}ClNO_4S$
Calculated C, 63.20; H, 7.34; N, 2.83 Found C, 63.11; H, 7.63; N, 2.80

Example 69

4-[4-[1-(4-Chlorophenylsulfonylamino)-2-methylpropyl]phenyl]butyric Acid

Appearance colorless needles (AcOEt-i-$Pr_2O$)
mp 121.5°~122.5° C.
Analysis for $C_{20}H_{24}ClNO_4S$
Calculated C, 58.60; H, 5.90; N, 3.42 Found C, 58.56; H, 5.84; N, 3.56

Example 70

4-[4-[1-(4-Chlorophenylsulfonylamino)-3-methylbutyl]phenyl]butyric Acid

Appearance colorless needles (80% aq.MeOH)
mp 139.5°~141.5° C.
Analysis for $C_{21}H_{26}ClNO_4S$
Calculated C, 59.49; H, 6.18; N, 3.30 Found C, 59.45; H, 6.38; N, 3.33

Example 71

4-[4-[1-(4-Chlorophenylsulfonylamino)-4-methylpentyl]phenyl]butyric Acid

Appearance colorless needles (80% aq. MeOH)
mp 139°~140.5° C.
Analysis for $C_{22}H_{28}ClNO_4S$
Calculated C, 60.33; H, 6.44; N, 3.20 Found C, 60.18; H, 6.67; N, 3.24

Example 72

4-[4-[1-(4-Chlorophenylsulfonylamino)-3,3-dimethylbutyl]phenyl]butyric Acid

Appearance colorless needles (80% aq. MeOH)
mp 150°~151° C.
Analysis for $C_{22}H_{28}ClNO_4S$
Calculated C, 60.33; H, 6.44; N, 3.20 Found C, 60.30; H, 6.66; N, 3.26

Example 73

4-[4-[(4-Chlorophenylsulfonylamino)cyclopentylmethyl]phenyl]butyric Acid

Appearance colorless needles (AcOEt-i-$Pr_2O$)
mp 139.5°~140° C.
Analysis for $C_{22}H_{26}ClNO_4S$
Calculated C, 60.61; H, 6.01; N, 3.21 Found C, 60.52; H, 5.98; N, 3.36

Example 74

4-[4-[(4-Chlorophenylsulfonylamino)cyclohexylmethyl]phenyl]butyric Acid

Appearance colorless needles (i-PrOH-i-$Pr_2O$)
mp 151°~152.5° C.
Analysis for $C_{23}H_{28}ClNO_4S$
Calculated C, 61.39; H, 6.27; N, 3.11 Found C, 61.13; H, 6.20; N, 3.21

Example 75

4-[4-[(4-Chlorophenylsulfonylamino)cycloheptylmethyl]phenyl]butyric Acid

Appearance colorless prisms (80% aq. MeOH)
mp 132.5°~133.5° C.
Analysis for $C_{24}H_{30}ClNO_4S$
Calculated C, 62.12; H, 6.52; N, 3.02 Found C, 61.99; H, 6.72; N, 2.99

Example 76 trans-4-[4-[(4-Chlorophenylsulfonylamino)(4-methylcyclohexyl)methyl]phenyl]butyric Acid Appearance colorless plates (90% aq. MeOH)
mp 167.5°~168.5° C.
Analysis for $C_{24}H_{30}ClNO_4S$
Calculated C, 62.12; H, 6.52; N, 3.02 Found C, 61.89; H, 6.78; N, 3.23

Example 77 trans-4-[4-[(4-Chlorophenylsulfonylamino)(4-pentylcyclohexyl)methyl]phenyl]butyric Acid Appearance colorless needles (95% aq. MeOH)
mp 157.5°~159.5° C.
Analysis for $C_{28}H_{38}ClNO_4S$
Calculated C, 64.66; H, 7.36; N, 2.69 Found C, 64.79; H, 7.63; N, 2.65

Example 78

4-[4-[1-(4-Chlorophenylsulfonylamino)-2-cyclopentylethyl]phenyl]butyric Acid

Appearance colorless needles (AcOEt-i-$Pr_2$O)
mp 163°~164° C.
Analysis for $C_{23}H_{28}ClNO_4S$
Calculated C, 61.39; H, 6.27; N, 3.11 Found C, 61.26; H, 6.49; N, 3.12

Example 79

4-[4-[1-(4-Chlorophenylsulfonylamino)-2-cyclohexylethyl]phenyl]butyric Acid

Appearance colorless needles (AcOEt-i-$Pr_2$O)
mp 146°~148° C.
Analysis for $C_{24}H_{30}ClNO_4S$
Calculated C, 62.12; H, 6.52; N, 3.02 Found C, 62.00; H, 6.77; N, 3.08

Example 80

4-[4-[1-(4-Chlorophenylsulfonylamino)-3-cyclohexylpropyl]phenyl]butyric Acid

Appearance colorless prisms (85% aq. MeOH)
mp 141.5°~143° C.
Analysis for $C_{25}H_{32}ClNO_4S$
Calculated C, 62.81; H, 6.75; N, 2.93 Found C, 62.67; H, 6.84; N, 2.93

Example 81

4-[4-[1-(4-Chlorophenylsulfonylamino)-4-cyclohexylbutyl]phenyl]butyric Acid

Appearance colorless needles (90% aq. MeOH)
mp 123.5°~125° C.
Analysis for $C_{26}H_{34}ClNO_4S$
Calculated C, 63.46; H, 6.96; N, 2.85 Found C, 63.33; H, 7.10; N, 2.93

Example 82

4-[4-[1-(4-Chlorophenylsulfonylamino)-5-cyclohexylpentyl]phenyl]butyric Acid

Appearance colorless crystals (90% aq. MeOH)
mp 119°~121° C.
Analysis for $C_{27}H_{36}ClNO_4S$
Calculated C, 64.08; H, 7.17; N, 2.77 Found C, 64.02; H, 7.25; N, 2.71

Example 83

4-[4-[1-(4-Chlorophenylsulfonylamino)-6-cyclohexylhexyl]phenyl]butyric Acid

Appearance colorless crystals (90% aq.MeOH)
mp 130°~131° C.
Analysis for $C_{28}H_{38}ClNO_4S$
Calculated C, 64.66; H, 7.36; N, 2.69 Found C, 64.60; H, 7.49; N, 2.64

Example 84

4-[4-[2-(1-Adamantyl)-1-(4-chlorophenylsulfonylamino)ethyl]phenyl]butyric Acid

Appearance colorless needles (85% aq.MeOH)
mp 154.5°~155° C.
Analysis for $C_{28}H_{34}ClNO_4S$
Calculated C, 65.16; H, 6.64; N, 2.71 Found C, 64.98; H, 6.81; N, 2.64

Example 85

4-[4-[1-(4-Chlorophenylsulfonylamino)-2-(2-norbornyl)ethyl]phenyl]butyric Acid

Appearance colorless needles (AcOEt-i-$Pr_2$O)
mp 147°~148.5° c.
Analysis for $C_{25}H_{31}ClNO_4S$
Calculated C, 62.94; H, 6.55; N, 2.94 Found C, 63.02; H, 6.51; N, 2.90

Example 86

3-[4-[1-(4-Chlorophenylsulfonylamino)-2-phenylethyl]phenyl]propionic Acid

Appearance colorless plates (EtOH)
mp 141.5°~142.5° C.
Analysis for $C_{23}H_{22}ClNO_4S$
Calculated C, 62.23; H, 4.99; N, 3.16 Found C, 62.25; H, 5.14; N, 3.10

Example 87

4-[4-[2-phenyl-1-(phenylsulfonylamino)ethyl]phenyl]butyric Acid

Appearance colorless needles (AcOEt-i-$Pr_2O$)
mp 121.5°~123° C.
Analysis for $C_{24}H_{25}NO_4S$
Calculated C, 68.06; H, 5.95; N, 3.31 Found C, 68.09; H, 6.09; N, 3.25

Example 88

4-[4-[1-(4-Fluorophenylsulfonylamino)-2-phenylethyl]phenyl]butyric Acid

Appearance colorless prisms (AcOEt-i-$Pr_2O$)
mp 134.5°~136° C.
Analysis for $C_{24}H_{24}FNO_4S$
Calculated C, 65.29; H, 5.48; N, 3.17 Found C, 65.23; H, 5.52; N, 3.11

Example 89

4-[4-[1-(4-Bromophenylsulfonylamino)-2-phenylethyl]phenyl]butyric Acid

Appearance colorless prisms (AcOEt-i-$Pr_2O$)
mp 154.5°~155.5° C.
Analysis for $C_{24}H_{24}BrNO_4S$
Calculated C, 57.37; H, 4.81; N, 2.79 Found C, 57.35; H, 4.81; N, 2.77

Example 90

4-[4-[1-(p-Tolylsulfonylamino)-2-phenylethyl]phenyl]butyric Acid

Appearance colorless prisms (AcOEt-i-$Pr_2O$)
mp 161.5°~162.5° C.
Analysis for $C_{25}H_{27}NO_4S$
Calculated C, 68.62; H, 6.22; N, 3.20 Found C, 68.44; H, 6.36; N, 3.12

Example 91

4-[4-[1-(4-Methoxyphenylsulfonylamino)-2-phenylethyl]phenyl]butyric Acid

Appearance colorless needles (AcOEt-i-$Pr_2O$)
mp 141.5°~142.5° C.
Analysis for $C_{25}H_{27}NO_5S$
Calculated C, 66.20; H, 6.00; N, 3.09 Found C, 66.28; H, 6.11; N, 3.04

Example 92

5-[4-[1-(4-Chlorophenylsulfonylamino)-2-phenylethyl]phenyl]valeric Acid

Appearance colorless prisms (MeOH)
mp 186°~187.5° C.
Analysis for $C_{25}H_{26}ClNO_4S$
Calculated C, 63.62; H, 5.35; N, 2.97 Found C, 63.44; H, 5.76; N, 2.97

Example 93

4-[4-[1-(4-Chlorophenylsulfonylamino)-2-(2-fluorophenyl)ethyl]phenyl]butyric Acid Appearance colorless needles (90% aq.MeOH)
mp 149.5°~150.5° C.
Analysis for $C_{24}H_{23}ClFNO_4S$
Calculated C, 60.56; H, 4.87; N, 2.94 Found C, 60.60; H, 4.79; N, 2.92

Example 94

4-[4-[1-(4-Chlorophenylsulfonylamino)-2-(3-fluorophenyl)ethyl]phenyl]butyric Acid Appearance colorless prisms (90% aq. MeOH)
mp 157°~159° C.
Analysis for $C_{24}H_{23}ClFNO_4S$
Calculated C, 60.56; H, 4.87; N, 2.94 Found C, 60.64; H, 4.85; N, 2.88

Example 95

4-[4-[1-(4-Chlorophenylsulfonylamino)-2-(4-fluorophenyl)ethyl]phenyl]butyric Acid Appearance colorless prisms (90% aq. MeOH)
mp 166°~167.5° C.
Analysis for $C_{24}H_{23}ClFNO_4S$
Calculated C, 60.56; H, 4.87; N, 2.94 Found C, 60.59; H, 4.88; N, 2.92

Example 96

4-[4-[2-(4-Chlorophenyl)-1-(4-chlorophenylsulfonylamino)ethyl]phenyl]butyric Acid Appearance colorless prisms (MeOH)
mp 169.5°~171° C.
Analysis for $C_{24}H_{23}Cl_2NO_4S$
Calculated C, 58.54; H, 4.71; N, 2.84 Found C, 58.60; H, 4.65; N, 2.85

Example 97

4-[4-[1-(4-Chlorophenylsulfonylamino)-2-(p-tolyl)ethyl]phenyl]butyric Acid

Appearance colorless columns (AcOEt-i-$Pr_2O$)
mp 148°–148.5° C.
Analysis for $C_{25}H_{28}ClNO_4S$
Calculated C, 63.62; H, 5.55; N, 2.97 Found C, 63.53; H, 5.63; N, 2.96

Example 98

4-[4-[1-(4-Chlorophenylsulfonylamino)-3-phenylpropyl]phenyl]butyric Acid

Appearance colorless needles (80% aq. MeOH)
mp 114.5°~116° C.
Analysis for $C_{25}H_{26}ClNO_4S$
Calculated C, 63.62; H, 5.55; N, 2.97 Found C, 63.42; H, 5.53; N, 3.01

Example 99

4-[4-[1-(4-Chlorophenylsulfonylamino) heptyl]phenyl]butyric Acid

Appearance colorless prisms (80% aq.MeOH)
mp 106°~108.5° C.
Analysis for $C_{23}H_{30}ClNO_4S$
Calculated C, 61.12; H, 6.69; N, 3.10 Found C, 61.00; H, 6.84; N, 3.20

Example 100

4-[4-[1-(4-Chlorophenylsulfonylamino) octyl]phenyl]butyric Acid

Appearance colorless needles (80% aq. MeOH)
mp 88°–89° C.
Analysis for $C_{24}H_{32}ClNO_4S$
Calculated C, 61.85; H, 6.92; N, 3.01 Found C, 61.75; H, 7.08; N, 3.10

Example 101

4-[4-[1-(4-Chlorophenylsulfonylamino) nonyl]phenyl]butyric Acid

Appearance colorless plates (80% aq. MeOH)
mp 101.5°~103° C.
Analysis for $C_{25}H_{34}ClNO_4S$
Calculated C, 62.55; H, 7.14; N, 2.92 Found C, 62.31; H, 7.34; N, 3.07

Example 102

5-[4-[1-(4-Chlorophenylsulfonylamino) pentyl]phenyl]valeric Acid

Appearance colorless prisms (80% aq. MeOH)
mp 106°~107.5° C.
Analysis for $C_{22}H_{28}ClNO_4S$
Calculated C, 60.33; H, 6.44; N, 3.20 Found C, 60.28; H, 6.64; N, 3.07

Example 103

4-[4-[1-(Phenylsulfonylamino)hexyl]phenyl]butyric Acid

Appearance colorless prisms (75% aq.MeOH)
mp 125°~126.5° C.
Analysis for $C_{22}H_{29}NO_4S$
Calculated C, 65.48; H, 7.24; N, 3.47 Found C, 65.39; H, 7.42; N, 3.41

Example 104

4-[4-[1-(4-Bromophenylsulfonylamino) hexyl]phenyl]butyric Acid

Appearance colorless needles (75% aq. MeOH)
mp 123°~124.5° C.
Analysis for $C_{22}H_{28}BrNO_4S$
Calculated C, 54.77; H, 5.85; N, 2.90 Found C, 54.53; H, 5.98; N, 2.89

Example 105

4-[4-[1-(4-Fluorophenylsulfonylamino)hexyl] phenyl]butyric Acid

Appearance colorless prisms (75% aq. MeOH)
mp 114°~116° C.
Analysis for $C_{22}H_{28}FNO_4S$
Calculated C, 62.69; H, 6.70; N, 3.32 Found C, 62.48; H, 6.81; N, 3.27

Example 106

5-[4-[1-(4-Chlorophenylsulfonylamino)hexyl] phenyl]valeric Acid

Appearance colorless prisms (80% aq. MeOH)
mp 85°~86.5° C.
Analysis for $C_{23}H_{30}ClNO_4S$
Calculated C, 61.12; H, 6.69; N, 3.10 Found C, 61.08; H, 6.93; N, 3.06

Example 107

4-[4-[1-(4-Chlorophenylsulfonylamino)-5-methylhexyl]phenyl]butyric Acid

Appearance colorless needles (80% aq. MeOH)
mp 124°~126° C.
Analysis for $C_{23}H_{30}ClNO_4S$
Calculated C, 61.12; H, 6.69; N, 3.10 Found C, 61.04; H, 6.86; N, 3.13

Example 108

4-[4-[1-(4-Chlorophenylsulfonylamino)-6-methylheptyl]phenyl]-butyric Acid

Appearance colorless prisms (80% aq. MeOH)
mp 113°~114° C.
Analysis for $C_{24}H_{32}ClNO_4S$
Calculated C, 61.85; H, 6.92; N, 3.01 Found C, 61.64; H, 7.12; N, 2.99

Example 109

4-[4-[1-(4-Chlorophenylsulfonylamino)-4,4-dimethylpentyl]phenyl]butyric Acid

Appearance colorless prisms (MeOH)
mp 141.5°~144.5° C.
Analysis for $C_{23}H_{30}ClNO_4S$
Calculated C, 61.12; H, 6.69; N, 3.10
Found C, 61.11; H, 6.99; N, 2.83

Example 110

4-[4-[1-(4-Chlorophenylsulfonylamino)-5,5-dimethylhexyl]phenyl]butyric Acid

Appearance colorless needles (80% aq. MeOH)
mp 114.5°~115.5° C.
Analysis for $C_{24}H_{32}ClNO_4S$
Calculated C, 61.85; H, 6.92; N, 3.01 Found C, 61.80; H, 6.80; N, 2.87

Example 111

4-[4-[1-(4-Chlorophenylsulfonylamino)-6,6-dimethylheptyl]phenyl]butyric Acid

Appearance colorless needles (80% aq. MeOH)
mp 132.5°~134.5° C.
Analysis for $C_{25}H_{34}ClNO_4S$
Calculated C, 62.55; H, 7.14; N, 2.92 Found C, 62.45; H, 7.04; N, 2.74

Example 112

4-[4-[1-(4-Chlorophenylsulfonylamino)-3-cyclopentylpropyl]phenyl]butyric Acid

Appearance colorless needles (90% aq. MeOH)
mp 135°~136° c.
Analysis for $C_{24}H_{30}ClNO_4S$
Calculated C, 62.12; H, 6.52; N, 3.02 Found C, 62.01; H, 6.58; N, 2.99

Example 113

5-[4-[1-(4-Chlorophenylsulfonylamino)-2-cyclohexylethyl]phenyl]valeric Acid

Appearance colorless prisms (MeOH)
mp 156.5°~158.5° C.
Analysis for $C_{25}H_{32}ClNO_4S$
Calculated C, 62.81; H, 6.75; N, 2.93 Found C, 62.79; H, 7.03; N, 2.80

Example 114

4-[4-[1-(4-Chlorophenylsulfonylamino)-4-phenylbutyl]phenyl]butyric Acid

Appearance colorless plates (80% aq.MeOH)
mp 130.5°~132.5° C.
Analysis for $C_{26}H_{28}ClNO_4S$
Calculated C, 64.25; H, 5.81; N, 2.88 Found C, 64.11; H, 5.63; N, 2.89

Example 115

4-[4-[1-(4-Chlorophenylsulfonylamino)-5-phenylpentyl]phenyl]-butyric Acid

Appearance colorless needles (90% aq. MeOH)
mp 102.5°~103.5° C.
Analysis for $C_{27}H_{30}ClNO_4S$
Calculated C, 64.85; H, 6.05; N, 2.80 Found C, 64.66; H, 5.96; N, 2.85

Example 116

4-[4-[1-(4-Chlorophenylsulfonylamino)-6-phenylhexyl]phenyl]butyric Acid

Appearance colorless needles (90% aq. MeOH)
mp 120.5°~122.5° C.

Example 117

4-[4-[3-(4-Butylphenyl)-1-(4-chlorophenylsulfonylamino)propyl]phenyl]butyric Acid Appearance colorless needles (80% aq. MeOH)
mp 113°~114° C.
Analysis for $C_{29}H_{34}ClNO_4S$
Calculated C, 65.96; H, 6.49; N, 2.65 Found C, 65.93; H, 6.58; N, 2.64

Example 118

4-[4-[3-(4-Butoxyphenyl)-1-(4-chlorophenylsulfonylamino)propyl]phenyl]butyric Acid Appearance colorless plates (90% aq. MeOH)
mp 115°~117.5° C.
Analysis for $C_{29}H_{34}ClNO_5S$
Calculated C, 64.02; H, 6.30; N, 2.57 Found C, 63.99; H, 6.56; N, 2.53

Example 119

4-[4-[1-(4-Chlorophenylsulfonylamino)-3-(p-tolyl)propyl]phenyl]butyric Acid

Appearance colorless needles (90% aq. MeOH)
mp 139°~141° C.
Analysis for $C_{26}H_{28}ClNO_4S$
Calculated C, 64.25; H, 5.81; N, 2.88 Found C, 64.19; H, 5.54; N, 3.02

Example 120

4-[4-[3-(4-Chlorophenyl)-1-(4-chlorophenylsulfonylamino)propyl]phenyl]butyric Acid Appearance colorless needles (80% aq.MeOH)
mp 123.5°~124.5° C.
Analysis for $C_{25}H_{25}Cl_2NO_4S$
Calculated C, 59.29; H, 4.98; N, 2.77 Found C, 59.42; H, 4.78; N, 2.80

Example 121

4-[4-[1-(4-Chlorophenylsulfonylamino)-3-(4-fluorophenyl)propyl]phenyl]butyric Acid Appearance colorless prisms (80% aq.MeOH)
mp 126°~127.5° C.
Analysis for $C_{25}H_{25}ClFNO_4S$
Calculated C, 61.28; H, 5.14; N, 2.86 Found C, 61.35; H, 5.19; N, 2.80

Example 122

4-[4-[1-(4-Chlorophenylsulfonylamino)-3-(3-fulorophenyl)propyl]phenyl]butyric Acid Appearance colorless plates (80% aq.MeOH)
mp 139°-140.5° C.
Analysis for $C_{25}H_{25}ClFNO_4S$ Calculated C, 61.28; H, 5.14; N, 2.86 Found C, 61.16; H, 5.03; N, 2.76

Example 123

(+)-4-[4-[1-(4-Chlorophenylsulfonylamino)-2-methylpropyl]phenyl]butyric Acid 10.00 g of (±)-4-[4-[1-(4-chlorophenylsulfonylamino)-2-methylpropyl]phenyl]butyric acid and 7.91 g of quinidine were dissolved in 60 ml of ethyl acetate by heating. After cooling, crystals precipitated were collected by filtration to give 8.65 g of colorless crystals. The results were recrystallized twice from ethanol to give 7.11 g of quinidine salt of the title compound as colorless prisms, mp 185°~186° C.

Analysis for $C_{20}H_{24}ClNO_4S \cdot C_{20}H_{24}N_2O_2$

Calculated C, 65.42; H, 6.59; N, 5.72 Found C, 65.24; H, 6.61; N, 6.00 Specific rotation $[\alpha]^{20}_D +126.8°$ (c=1,MeOH)

The quinidine salt obtained above was added to dilute hydrochloric acid and extraction was carried out using ethyl acetate. The ethyl acetate layer was washed with water and dried, and then the solvent was removed. The resulting residue was recrystallized from a mixture of isopropyl ether and ethyl acetate to give 3.24 g of the title compound as colorless needles, mp 117°~119° C.

Analysis for $C_{20}H_{24}ClNO_4S$

Calculated C, 58.60; H, 5.90; N, 3.42 Found C, 58.49; H, 5.91; N, 3.60 Specific rotation $[\alpha]^{20}_D +9.1°$ (c=1,MeOH)

Example 124

(−)-4-[4-[1-(4-Chlorophenylsulfonylamino)-2-methylpropyl]phenyl]butyric Acid 4.65 g of free acid, recovered in an ordinary manner from the residue obtained from the filtrate that was recovered after the salt formation between 10.00 g of (±)-4-[4-[1-(4-chlorophenylsulfonylamino)-2-methylpropyl]phenyl]butyric acid and 7.91 g of quinidine, and 4.08 g of quinine were dissolved in 30 ml of ethyl acetate. After cooling, crystals precipitated were collected by filtration to give 7.60 g of colorless crystals. The results were recrystallized successively once from ethanol and once from methanol to give 6.41 g of quinine salt of the title compound as colorless needles, mp 185°~186° C.

Analysis for $C_{20}H_{24}ClNO_4S \cdot C_{20}H_{24}N_2O_2$

Calculated C, 65.42; H, 6.59; N, 5.72 Found C, 65.19; H, 6.54; N, 5.89 Specific rotation $[\alpha]^{20}_D -101.6°$ (c=1,MeOH)

The quinine salt obtained above was added to dilute hydrochloric acid, and extraction was carried out using ethyl acetate. The ethyl acetate layer was washed with water and dried, and then the solvent was removed. The resulting residue was recrystallized from a mixture of isopropyl ether and ethyl acetate to give 2.89 g of the title compound as colorless needles, mp 116.5°~119° C.

Analysis for $C_{20}H_{24}ClNO_4S$

Calculated C, 58.60; H, 5.90; N, 3.42 Found C, 58.49; H, 5.84; N, 3.63 Specific rotation $[\alpha]^{20}_D -9.1°$ (c=1,MeOH)

Example 125

(−)-4-[4-[(4-Chlorophenylsulfonylamino) cyclopentylmethyl]phenyl]butyric Acid 7.00 g of (±)-4-[4-[(4-chlorophenylsulfonylamino)cyclopentylmethyl]phenyl]butyric acid and 5.21 g of quinidine were dissolved in 45 ml of ethyl acetate by heating. After cooling, crystals precipitated were collected by filtration to give 6.78 g of colorless crystals. The results were recrystallized twice from isopropanol and once from ethanol to give 4.83 g of quinidine salt of the title compound as colorless needles, mp 178.5°~180.5° C.

Analysis for $C_{22}H_{26}ClNO_4S \cdot C_{20}H_{24}N_2O_2$

Calculated C, 66.34; H, 6.63; N, 5.53 Found C, 66.21; H, 6.64; N, 5.48 Specific rotation $[\alpha]^{20}_D +115.0°$ (c=1,MeOH)

The quinidine salt obtained above was added to dilute hydrochloric acid and extraction was carried out using ethyl acetate. The ethyl acetate layer was washed with water and dried, and then the solvent was removed. The resulting residue was recrystallized from 90% aqueous methanol to give 2.15 g of the title compound as colorless needles, mp 160°~162° C.

Analysis for $C_{22}H_{26}ClNO_4S$

Calculated C, 60.61; H, 6.01; N, 3.21 Found C, 60.80; H, 6.01; N, 3.20 Specific rotation $[\alpha]^{20}_D -6.2°$ (c=1,MeOH)

Example 126

(+)-4-[4-[(4-Chlorophenylsulfonylamino) cyclopentylmethyl]phenyl]butyric Acid 3.54 g of free acid, recovered in an ordinary manner from the residue obtained from the filtrate that was recovered after the salt formation between 7.00 g of (±)-4-[4-[(4-chlorophenylsulfonylamino)cyclopentylmethyl]phenyl]butyric acid and 5.21 g of quinidine, and 2.92 g of quinine were dissolved in 15 ml of ethyl acetate. After cooling, crystals precipitated were collected by filtration to give 4.57 g of colorless crystals. The results were recrystallized successively once from isopropanol and once from ethanol to give 4.90 g of quinine salt of the title compound as colorless prisms, mp 177°~179° C.

Analysis for $C_{22}H_{26}ClNO_4S \cdot C_{20}H_{24}N_2O_2$

Calculated C, 66.34; H, 6.63; N, 5.53 Found C, 66.17; H, 6.61; N, 5.47 Specific rotation $[\alpha]^{20}_D -84.4°$ (c=1,MeOH)

The quinine salt obtained above was added to dilute hydrochloric acid and extraction was carried out using ethyl acetate. The ethyl acetate layer was washed with water and dried, and then the solvent was removed. The resulting residue was recrystallized from 90% aqueous methanol to give 2.13 g of the title compound as colorless needles, mp 160°~162° C.

Analysis for $C_{22}H_{26}ClNO_4S$

Calculated C, 60.61; H, 6.01; N, 3.21 Found C, 60.63; H, 5.99; N, 3.14 Specific rotation $[\alpha]^{20}_D +5.8°$ (c=1,MeOH)

Example 127

(+)-4-[4-[(4-Chlorophenylsulfonylamino) cyclohexylmethyl]phenyl]butyric Acid 10.00 g of (±)-4-[4-[(4-chlorophenylsulfonylamino)cyclohexylmethyl]phenyl]butyric acid and 7.21 g of quinidine were dissolved in 40 ml of ethyl acetate by heating. After cooling, crystals precipitated were collected by filtration to give 8.38 g of colorless crystals. Recrystallization from isopropanol gave 6.61 g quinidine salt of the title compound as colorless prisms, mp 173°~174° C.

Analysis for $C_{23}H_{28}ClNO_4S \cdot C_{20}H_{24}N_2O_2$

Calculated C, 66.69; H, 6.77; N, 5.43 Found C, 66.55; H, 6.85; N, 5.30 Specific rotation $[\alpha]^{20}_D +115.3°$ (c=1,MeOH)

The quinidine salt obtained above was added to dilute hydrochloric acid, and extraction was carried out using ethyl acetate. The ethyl acetate layer was washed with water and dried, and then the solvent was removed. The resulting residue was recrystallized from 80% aqueous methanol to give 3.24 g of the title compound as colorless needles, mp 165°~166° C.

Analysis for $C_{23}H_{28}ClNO_4S$

Calculated C, 61.39; H, 6.27; N, 3.11 Found C, 61.46; H, 6.20; N, 3.06 Specific rotation $[\alpha]^{20}_D$+3.1° (c=1,MeOH)

Example 128

(−)-4-[4-[(4-Chlorophenylsulfonylamino)cyclohexylmethyl]phenyl]butyric Acid 4.70 g of free acid, recovered in an ordinary manner from the residue obtained from the filtrate that was recovered after the salt formation between 10.00 g of (±)-4-[4-[(4-chlorophenylsulfonylamino)cyclohexylmethyl]phenyl]butyric acid and 7.21 g of quinidine, and 3.78 g of quinine were dissolved in 20 ml of ethyl acetate. After cooling, crystals precipitated were collected by filtration to give 6.80 g of colorless crystals. The results were recrystallized from isopropanol to give 6.26 g of quinine salt of the title compound as colorless prisms, mp 176°~177° C.

Analysis for $C_{23}H_{28}ClNO_4S \cdot C_{20}H_{24}N_2O_2$

Calculated C, 66.69; H, 6.77; N, 5.43 Found C, 66.41; H, 6.91; N, 5.22 Specific rotation $[\alpha]^{20}_D$−86.2° (c=1,MeOH)

The quinine salt obtained above was added to dilute hydrochloric acid, and extraction was carried out using ethyl acetate. The ethyl acetate layer was washed with water and dried, and then the solvent was removed. The resulting residue was recrystallized from 80% aqueous methanol to give 3.03 g of the title compound as colorless needles, mp 165°~166° C.

Analysis for $C_{23}H_{28}ClNO_4S$

Calculated C, 61.39; H, 6.27; N, 3.11 Found C, 61.47; H, 6.20; N, 3.12 Specific rotation $[\alpha]^{20}_D$−3.3° (c=1,MeOH)

Example 129

(−)-4-[4-[1-(4-Chlorophenylsulfonylamino)-2-phenylethyl]phenyl]butyric Acid 10.00 g of (±)-4-[4-[1-(4-chlorophenylsulfonylamino)-2-phenylethyl]phenyl]butyric acid and 7.08 g of quinidine were dissolved in 70 ml of ethyl acetate by heating. After cooling, crystals precipitated were collected by filtration to give 8.02 g of colorless crystals. The results were recrystallized from methanol to give 6.37 g of quinidine salt of the title compound as colorless prisms, mp 181.5°~183.5° C.

Analysis for $C_{24}H_{24}ClNO_4S \cdot C_{20}H_{24}N_2O_2$

Calculated C, 67.55; H, 6.18; N, 5.37 Found C, 67.48; H, 6.17; N, 5.50 Specific rotation $[\alpha]^{20}_D$+93.6° (c=1,MeOH)

The quinidine salt obtained above was added to dilute hydrochloric acid, and extraction was carried out using ethyl acetate. The ethyl acetate layer was washed with water and dried, and then the solvent was removed. The resulting residue was recrystallized from 90% aqueous ethanol to give 3.14 g of the title compound as colorless needles, mp 173.5°~174° C.

Analysis for $C_{24}H_{24}ClNO_4S$

Calculated C, 62.94; H, 5.28; N, 3.06 Found C, 62.94; H, 5.19; N, 3.17 Specific rotation $[\alpha]^{20}_D$−40.3° (c=1,MeOH)

Example 130

(+)-4-[4-[1-(4-Chlorophenylsulfonylamino)-2-phenylethyl]phenyl]butyric Acid 5.00 g of free acid, recovered in an ordinary manner from the residue obtained from the filtrate that was recovered after the salt formation between 10.00 g of (±)-4-[4-[1-(4-chlorophenylsulfonylamino)-2-phenylethyl]phenyl]butyric acid and 7.08 g of quinidine, and 3.92 g of quinine were dissolved in 40 ml of ethyl acetate. After cooling, crystals precipitated were collected by filtration to give 7.50 g of colorless crystals. The results were recrystallized from ethanol to give 6.50 g of quinine salt of the title compound as colorless prisms, mp 174°~176° C.

Analysis for $C_{24}H_{24}ClNO_4S \cdot C_{20}H_{24}N_2O_2$

Calculated C, 67.55; H, 6.18; N, 5.37 Found C, 67.42; H, 6.16; N, 5.43 Specific rotation $[\alpha]^{20}_D$−63.7° (c=1,MeOH)

The quinine salt obtained above was added to dilute hydrochloric acid, and extraction was carried out using ethyl acetate. The ethyl acetate layer was washed with water and dried, and the solvent was removed. The resulting residue was recrystallized from 90% aqueous ethanol to give 3.06 g of the title compound as colorless needles, mp 173°~174° C.

Analysis for $C_{24}H_{24}ClNO_4S$

Calculated C, 62.94; H, 5.28; N, 3.06 Found C, 62.89; H, 5.30; N, 3.26 Specific rotation $[\alpha]^{20}_D$+40.2° (c=1,MeOH)

Example 131

(−)-4-[4-[1-(4-Chlorophenylsulfonylamino)hexyl]phenyl]butyric Acid 8.00 g of (±)-4-[4-[1-(4-chlorophenylsulfonylamino)hexyl]phenyl]butyric acid and 6.58 g of quinine were dissolved in 45 ml of ethyl acetate by heating. After cooling, crystals precipitated were collected by filtration to give 6.53 g of colorless crystals. The results were recrystallized twice from 90% aqueous ethanol to give 4.71 g of quinine salt of the title compound as colorless prisms, mp 166.5°~170° C.

Analysis for $C_{22}H_{28}ClNO_4S \cdot C_{20}H_{24}N_2O_2$

Calculated C, 66.17; H, 6.87; N, 5.51 Found C, 66.08; H, 6.97; N, 5.39 Specific rotation $[\alpha]^{20}_D$−95.0° (c=1,MeOH)

The quinine salt obtained above was added to dilute hydrochloric acid, and extraction was carried out using ethyl acetate. The ethyl acetate layer was washed with water and dried, and the solvent was removed. The resulting residue was recrystallized from 80% aqueous methanol to give 2.35 g of the title compound as colorless needles, mp 134.5°~137° C.

Analysis for $C_{22}H_{28}ClNO_4S$

Calculated C, 60.33; H, 6.44; N, 3.20 Found C, 60.40; H, 6.65; N, 3.34 Specific rotation $[\alpha]^{20}_D$−10.7° (c=1,MeOH)

Example 132

(+)-4-[4-[1-(4-Chlorophenylsulfonylamino)hexyl]phenyl]butyric Acid 4.60 g of free acid, recovered in an ordinary manner from the residue obtained from the filtrate that was recovered after the salt formation between 8.00 g of (±)-4-[4-[1-(4-chlorophenylsulfonylamino)hexyl]phenyl]butyric acid and 6.58 g of quinine, and 3.41 g of quinidine were dissolved in 20 ml of ethyl acetate by heating. After cooling, crystals precipitated were collected by filtration to give 6.00 g of colorless crystals. The results were recrystallized twice from 80% aqueous ethanol to give 4.61 g of quinidine salt of the title compound as colorless prisms, mp 157°~160° C.

Analysis for $C_{22}H_{28}ClNO_4S \cdot C_{20}H_{24}N_2O_2$

Calculated C, 66.17; H, 6.87; N, 5.51 Found C, 66.09; H, 6.74; N, 5.41 Specific rotation $[\alpha]^{20}_D+124.6°$ (c=1,MeOH)

The quinidine salt obtained above was added to dilute hydrochloric acid, and extraction was carried out using ethyl acetate. The ethyl acetate layer was washed with water and dried, and then the solvent was removed. The resulting residue was recrystallized from 80% aqueous methanol to give 2.27 g of the title compound as colorless needles; mp 133.5°~136° C.

Analysis for $C_{22}H_{28}ClNO_4S$

Calculated C, 60.33; H, 6.44; N, 3.20 Found C, 60.41; H, 6.66; N, 3.34 Specific rotation $[\alpha]^{20}_D+11.2°$ (c=1,MeOH)

Example 133

A tablet is prepared according to the following formulation:

| | |
|---|---|
| Compound of Example 67 | 50 mg |
| Lactose | q.s. |
| Corn starch | 34 mg |
| Magnesium stearate | 2 mg |
| Hydroxypropylmethylcellulose | 8 mg |
| Polyethyleneglycol 6000 | 0.5 mg |
| Titanium oxide | 0.5 mg |
| | 160 mg |

Example 134

A capsule is prepared according to the following formulation:

| | |
|---|---|
| Compound of Example 67 | 50 mg |
| Lactose | q.s. |
| Calcium carboxymethylcellulose | 15 mg |
| Hydroxypropylcellulose | 2 mg |
| Magnesium stearate | 2 mg |
| | 140 mg |

The above ingredients are mixed in an ordinary manner and filled into a hard capsule.

Example 135

Powder is prepared according to the following formulation:

| | |
|---|---|
| Compound of Example 67 | 50 mg |
| Lactose | q.s. |
| D-Mannitol | 500 mg |
| Hydroxypropylcellulose | 5 mg |
| Talc | 2 mg |
| | 1000 mg |

Example 136

Injection is prepared according to the following formulation:

| | |
|---|---|
| Compound of Example 67 | 10 mg |
| Glucose | 100 mg |
| Sodium hydroxide | q.s. |
| Distilled water for injection | q.s. |
| | 2 ml |

INDUSTRIAL APPLICABILITY

The novel benzenesulfonamide derivatives of the present invention represented by the above Formula (I) and pharmacologically acceptable salts thereof are highly useful as platelet aggregation inhibitors, antithrombotic agents, antiasthmatic agents, antiallergic agents and the like.

What is claimed is:

1. A benzenesulfonamide derivative represented by the following general formula:

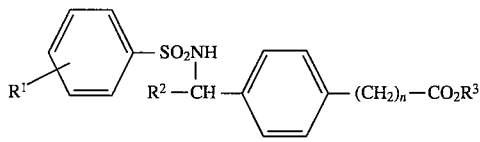

wherein $R^1$ represents a hydrogen atom, a lower alkyl group, a lower alkoxy group or a halogen atom; $R^2$ represents a $C_2$–$C_{10}$ straight- or branched-chain alkyl group, a $C_3$–$C_8$ cycloalkyl group which may be substituted with one or more $C_1$–$C_6$ alkyl groups on its ring, a $C_1$–$C_6$ alkyl group substituted with one or more $C_3$–$C_8$ cycloalkyl groups, 1-adamantylmethyl group, 2-norbornylmethyl group, or a $C_1$–$C_6$ alkyl group substituted with one or more phenyl groups whose benzene ring may have one or more substituents; $R^3$ represents a hydrogen atom or a lower alkyl group; and n is an integer of from 2 to 4, and a pharmacologically acceptable salt thereof.

2. The compound and pharmacologically acceptable salt thereof according to claim 1, wherein $R^1$ represents a halogen atom; $R^2$ represents a $C_4$–$C_8$ straight- or branched-chain alkyl group or a $C_1$–$C_2$ alkyl group substituted with one or more phenyl groups whose benzene ring may have one or more substituents; $R^3$ represents a hydrogen atom or a lower alkyl group; and n is 3.

3. The compound and pharmacologically acceptable salt thereof according to claim 2, wherein $R^1$ represents a halogen atom; $R^2$ represents a $C_4$–$C_8$ straight- or branched-chain alkyl group, or benzyl group or phenethyl group which may be substituted with one or more halogen atoms or lower alkyl groups; $R^3$ represents a hydrogen atom or a lower alkyl group; and n is 3.

4. The compound and pharmacologically acceptable salt thereof according to claim 3 which is selected from the group consisting of:
4-[4-[1-(4-chlorophenylsulfonylamino)pentyl]phenyl]butyric acid;
4-[4-[1-(4-chlorophenylsulfonylamino)hexyl]phenyl]butyric acid;
4-[4-[1-(4-fluorophenylsulfonylamino)hexyl]phenyl]butyric acid;

4-[4-[1-(4-bromophenylsulfonylamino)hexyl]phenyl]butyric acid;

4-[4-[1-(4-chlorophenylsulfonylamino)-6-methylheptyl]phenyl]butyric acid;

4-[4-[1-(4-chlorophenylsulfonylamino)-5-methylhexyl]phenyl]butyric acid;

4-[4-[1-(4-chlorophenylsulfonylamino)-2-phenylethyl]phenyl]butyric acid;

4-[4-[1-(4-bromophenylsulfonylamino)-2-phenylethyl]phenyl]butyric acid;

4-[4-[1-(4-chlorophenylsulfonylamino)-2-(3-fluorophenyl)ethyl]phenyl]butyric acid;

4-[4-[2-(4-chlorophenyl)-1-(4-chlorophenylsulfonylamino)ethyl]phenyl]butyric acid;

4-[4-[1-(4-chlorophenyl)-2-(p-tolyl)ethyl]-phenyl]butyric acid; and mixtures thereof.

5. A pharmaceutical composition for the treatment of an ailment due to elevated levels of Thromboxane $A_2$ or Leucotriene comprising a pharmaceutically effective amount of a benzenesulfonamide derivative of claim 1 in a pharmaceutically acceptable carrier.

6. A unit dosage form for the treatment of an ailment due to elevated levels of thromboxane $A_2$ or leucotriene comprising a pharmaceutically effective amount of a benzenesulfonamide derivative of claim 1 in a pharmaceutically acceptable carrier.

7. A unit dosage form according to claim 6, wherein the unit dosage is for oral or parenteral administration.

8. A unit dosage form according to claim 6, for oral administration in the form of a tablet, capsule or powder.

9. A method of treating thrombosis or excessive platelet aggregation by administering to a subject a pharmaceutically effective amount of a benzenesulfonamide derivative of claim 1 in a pharmaceutically effective carrier.

10. A method of treating asthma by administering to a subject a pharmaceutically effective amount of a benzenesulfonamide derivative of claim 1 in a pharmaceutically effective carrier.

11. A method of treating an allergy by administering to a subject a pharmaceutically effective amount of a benzenesulfonamide derivative of claim 1 in a pharmaceutically effective carrier.

* * * * *